(12) United States Patent
Montelaro et al.

(10) Patent No.: US 8,071,540 B2
(45) Date of Patent: Dec. 6, 2011

(54) VIRUS DERIVED ANTIMICROBIAL PEPTIDES

(75) Inventors: Ronald C. Montelaro, Wexford, PA (US); Timothy A. Mietzner, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 390 days.

(21) Appl. No.: 12/171,806

(22) Filed: Jul. 11, 2008

(65) Prior Publication Data

US 2009/0099533 A1 Apr. 16, 2009

Related U.S. Application Data

(60) Provisional application No. 60/959,453, filed on Jul. 13, 2007.

(51) Int. Cl.
*A61K 38/10* (2006.01)
*A61K 38/16* (2006.01)
*C07K 7/08* (2006.01)
*C07K 14/00* (2006.01)

(52) U.S. Cl. ............ 514/2.4; 514/3.3; 514/3.4; 514/3.7; 514/3.8; 514/21.4; 514/21.5; 530/325; 530/326; 530/327

(58) Field of Classification Search .................. None
See application file for complete search history.

(56) References Cited

U.S. PATENT DOCUMENTS

| | | | |
|---|---|---|---|
| 5,504,190 | A | 4/1996 | Houghten et al. |
| 5,714,577 | A | 2/1998 | Montelaro et al. |
| 5,945,507 | A | 8/1999 | Montelaro et al. |
| 5,981,698 | A | 11/1999 | Brittain |
| 6,835,713 | B2 | 12/2004 | Mietzner et al. |
| 6,887,847 | B2 | 5/2005 | Montelaro et al. |
| 2003/0036627 | A1* | 2/2003 | Montelaro et al. ............ 530/324 |
| 2004/0043041 | A1 | 3/2004 | Baker et al. |
| 2005/0025761 | A1 | 2/2005 | Thorpe et al. |
| 2005/0282239 | A1 | 12/2005 | Allbritton et al. |
| 2007/0225213 | A1* | 9/2007 | Kosak .............................. 514/7 |

(Continued)

FOREIGN PATENT DOCUMENTS

EP   0273716 B1   8/1993

(Continued)

OTHER PUBLICATIONS

Arroyo et al., "Membrane Permeabilization by Different Regions of the Human Immunodeficiency Virus Type 1 Transmembrane Glycoprotein gp41", J. Virol. 69: 4095-4102, 1995.

(Continued)

*Primary Examiner* — Jeffrey E Russel
(74) *Attorney, Agent, or Firm* — The Web Law Firm

(57) ABSTRACT

Described herein are peptides having antimicrobial activity (antimicrobial peptides). The antimicrobial peptides, designated LBU, WLBU and WR, are analogs of the Lentivirus Lytic Peptide 1 (LLP1) amino acid sequence. The antimicrobial peptides are monomers or multimers of peptides referred to as the Lytic Base Unit (LBU) peptides, derived from the LLP1 analogs and also having antimicrobial activity. Also described herein are using the peptides in a variety of contexts, including the treatment or prevention of infectious diseases. Methods of killing fungi, such as *Candida* and *Cryptococcus* species, and bacteria, such as *B. anthracis*, are provided herein. Methods of neutralizing enveloped viruses, such as poxvirus, herpesvirus, rhabdovirus, hepadnavirus, baculovirus, orthomyxovirus, paramyxovirus, retrovirus, togavirus, bunyavirus and flavivirus, including influenza virus and HIV-1 also are provided herein. Solid phase substrates and peptide-cargo complexes comprising the peptides also are provided.

26 Claims, 26 Drawing Sheets

U.S. PATENT DOCUMENTS

2009/0053278 A1* 2/2009 Fatora et al. .................. 424/423

FOREIGN PATENT DOCUMENTS

WO       WO 03103718 A2 * 12/2003
WO     WO 2008070083 A2 * 6/2008

OTHER PUBLICATIONS

Beary et al., "Interruption of T-Cell signal transduction by lentivirus lytic peptides from HIV-1 transmembrane protein", Journal of Peptide Research, 51: 75-79, 1998.
Blondelie et al., "Design of Model Amphipathic Peptides Having Potent Anitmicrobial Activities", Biochemistry, 31:12688-12694, 1992.
Burton, E. et al. Antibiofilm activity of GlmU enzyme inhibitors against catheter-associated uropathogens. Antimicrob Agents Chemother 50, 1835-1840 (2006).
Caron, N. J., Torrente, Y., Camirand, G., Bujold, M., Chapdelaine, P., Leriche, K., Bresolin, N., and Tremblay, J. P. Intracellular delivery of a Tat-eGFP fusion protein into muscle cells, Mol Ther. 3: 310-8, 2001.
Chernomordik, A. et al., An Amphipathic Peptide from the C-Terminal Region of the HIV Envelope Glycoprotein Causes Pore Formation in Membranes, J. Virol. 68, 7115-7123 (1994).
Chou et al., "Prediction of the Secondary Structure of Proteins From Their Amino Acid Sequence", Adv Enz Relat Areas Mol Bio, 47: 45-146, 1978.
Chou et al., Prediction of Protein Conformation, Biochemistry 13:222, 1974.
Cirioni, O. et al. Pre-treatment of central venous catheters with the cathelicidin BMAP-28 enhances the efficacy of antistaphylococcal agents in the treatment of experimental catheter-related infection. Peptides 27, 2104-2110 (2006).
Comardelle et al., "A Synthetic Peptide Corresponding to the Carboxy Terminus of Human Immunodeficiency Virus Type 1 Transmembrane Glycoprotein Induces Alterations in the Ionic Permeability of *Xenopus laevis* Oocytes", AIDS Research & Human Retroviruses, 13: No. 17, pp. 1525-1532, 1997.
Deslouches et al., Activity of the de novo engineered antimicrobial peptide WLBU-2 against *P. aeruginosa* in human serum and whole blood: implications for systemic applications, Antimicrob Agents Chemother Aug. 2005;49(8):3208-16.
Deslouches, B. et al. De novo generation of cationic antimicrobial peptides: influence of length and tryptophan substitution on antimicrobial activity. Antimicrob Agents Chemother 49, 316-322 (2005).
Deslouches, B. et al. De novo-derived cationic antimicrobial peptide activity in a murine model of *P. aeruginosa* bacteraemia. J Antimicrob Chemother 60, 669-672 (2007).
Dietz, G. P. and Bahr, M. Delivery of bioactive molecules into the cell: the Trojan horse approach, Mol Cell Neurosci. 27: 85-131, 2004.
Eisenberg and Wesson, "The Most Highly Amphiphilic .A-inverted.-Helics Include Two Amino Acid Segments in Human Immunodeficiency Virus Glycoprotein 41", Biopolymers, 29: 171-177, 1990.
Eisenberg et al., "The hydrophobic moment detects periodicity in protein hydrophocity", Proc. Natl. Acad. Sci. U.S.A., 81:140-144, 1984.
Eisenberg et al., "Analysis of Membrane and Surface Protein Sequences with the Hydrophobic Moment Plot," J. Mol. Biol. 179:125, 1984.
El-Ghannam, A, K Ahmed, and M Omran, Nanoporous Delivery System to Treat Osteomyelitis and Regenerate Bone: Gentamicin Release Kinetics and Bactericidal Effect, J Biomed Mater Res B Appl Biomater May 2005;73(2):277-84).
Ellman, G. L., "Tissue Sulfhydryl Groups," Arch. Biochem. 82: 70-77, 1959.
Falagas, M.E., Fragoulis, K., Bliziotis, I.A. & Chatzinikolaou, I. Rifampicin-impregnated central venous catheters: a meta-analysis of randomized controlled trials. J Antimicrob Chemother 59, 359-369 (2007).
File,TM. "Overview of Resistance in the 1990s", Chest. 115:3S-8S. Mar. 1999 Supplement.

Fontenot et al., "A Survey of Potential Problems and Quality Control in Peptide Synthesis by the Fluorenylmethoxycarbonyl Procedure", Peptide Research, 4:19-25, 1991.
Friedrich et al., "Salt-Resistance Alpha-Helical Cationic Antimicrobial Peptides", Antimicrobial Agents and Chemotherapy, 43: 1542-1548, 1999.
Fujii et al., A molecular model for membrane fusion based on solution studies of an amphiphilic peptide from HIV gp41 Protein Sci. 1:1454, 1992.
Ganz and Lehrer, "Antimicrobial peptides of leukocytes", Current Opinion in Hematology, 4: 53-58, 1997.
Garnier et al., "Analysis of the Accuracy and Implications of Simple Methods for Predicting the Secondary Structure of Globular Proteins", J. Mol. Biol., 120: 97-120, 1978.
Gawrisch et al., Interaction of Peptide Fragment 828-848 of the Envlope Glycoprotein of HIV with Lipid Bilayers, Biochemistry 32, 3112-3118 (1993).
Guelen, L., Paterson, H., Gaken, J., Meyers, M., Farzaneh, F., and Tavassoli, M. TAT-apoptin is efficiently delivered and induces apoptosis in cancer cells, Oncogene. 23: 1153-65, 2004.
Habermann et al., Bee and wasp venoms, Science 177:314, 1972.
Hancock. R.E., "Host Defence (Cationic) Peptides: What Is Their Future Clinical Potential?", Drugs, 57: 469-473, Adis International Limited, 1999.
Ho et al., (2001) Cancer Research 61:474-477; Mai, et al. (2002), Efficiency of Protein Transduction is Cell Type-dependent and is enhanced by Dextran Sulfate, J. Biol. Chem. 277(33):30208-218.
Honig, B. (1999) Protein folding: from the levinthal paradox to structure prediction. J. Mol. Biol. vol. 293, pp. 283-293. Review.
Hwang and Vogel, "Structure-function relationships of antimicrobial peptides", Biochem. Cell Biol., 76: 235-246, 1998.
Isaacs, C.E. et al. Inactivation of herpes simplex virus clinical isolates by using a combination microbicide. Antimicrob Agents Chemother 50, 1063-1066 (2006).
Kalia, V. et al (2003) Rational site-directed mutations of the LLP1 and LLP-2 lentivirus lytic peptide domains in the intracytoplasmic tail of human immunodeficiency virus type 1 gp41 ., J. Virol. vol. 77, pp. 3634-3646.
Koenig, B. et al., Effect of the conformation of a peptide from gp41 on binding and domain formation in model membranes, Mol. Membrane Biol. 12, 77-82 (1995).
Lehrer, R. I., M. E. Selsted, D. Szklarek, and F. J. 1983. Antibacterial Activity of Microbicidal Cationic Proteins 1 and 2, Natural Peptide Antibiotics of Rabbit Lung Macrophages Infect. Immun. 42: 10-4, 1983.
Mai, et al. (2002) "Efficiency of Protein Transduction Is Cell Type-dependent and Is Enhanced by Dextran Sulfate," J. . Biol. Chem. 277(33):30208-218.
Merrifield et al., "Design and synthesis of antimicrobial peptides", Antimicrobial Peptides, Ciba Foundation Symposium, , 5-26, 1994.
Mi, Z., Mai, J., Lu, X., and Robbins, P. D. Characterization of a class of cationic peptides able to facilitate efficient protein transduction in vitro and in vivo, Mol Ther. 2: 339-47, 2000.
Miller et al., "A Structural Correlation Between Lentivirus Transmembrane Proteins and Natural Cytolytic Peptides", AIDS Research & Human Retroviruses, 7:511-519, 1991.
Miller et al., "Alterations in Cell Membrane Permeability by the Lentivirus Lytic Peptide (LLP-1) of HIV-1 Transmembrane Protein", Virology, 196: 89-100, 1993.
Miller et al., "Identification of a Calmodulin-Binding and Inhibitory Peptide Domain in the HIV-1 Transmembrane Glycoprotein", 1993, AIDS Research and Human Retroviruses, 9: 1057-1066.
Moore et al., "Preliminary Experimental Anticancer Activity of Cecropins", Peptide Research, 7:265-269, 1994.
Morris, M. C., Depollier, J., Mery, J., Heitz, F., and Divita, G. A peptide carrier for the delivery of biologically active proteins into mammalian cells, Nat Biotechnol. 19: 1173-6, 2001.
Palace, G.P., Fitzpatrick, R., Tran, K.V., Phoebe, C.H., Jr. & Norton, K. Determination of amino acids in diverse polymeric matrices using HPLC, with emphasis on agars and agaroses. Biochim Biophys Acta 1472, 509-518 (1999).

Pearson et al., "Method for Reliable Determination of Minimal Lethal Antibiotic Concentrations," Antimicrob. Agents Chemother. 18:699, 1980.

Phadke, S.M. et al. Selective toxicity of engineered lentivirus lytic peptides in a CF airway cell model. Peptides 24, 1099-1107 (2003).

Ribeiro, M. M., Klein, D., Pileggi, A., Molano, R. D., Fraker, C., Ricordi, C., Inverardi, L., and Pastori, R. L. Heme oxygenase-1 fused to a TAT peptide transduces and protects pancreatic beta-cells, Biochem Biophys Res Commun. 305: 876-81, 2003.

International Search Report and Written Opinion for PCT/US08169776, Montelaro et al., Jan. 12, 2009.

Robinson, W.E, Jr., B. McDougall, D. Tran and M.E. Selsted (1998) Journal of Leukocyte Biology 63:94-100.

Rushlow et al., Lentivirus genomic organization: the complete nucleotide sequence of the env gene region of equine infectious anemia virus. Virology 155:309, 1986.

Sarin et al., "Quantitative Monitoring of Solid-Phase Peptide Synthesis by the Ninhydrin Reaction'," Analytical Biochemistry 117:147-157, (1981).

Scott, Yan, and Hancock, "Biological Properties of Structurally Related .alpha.-Helical Cationic Antimicrobial Peptides", Infection & Immunity, 67: 2005-2009, Apr. 1999.

Shen, H., Mai, J. C., Qiu, L., Cao, S., Robbins, P. D., and Cheng, T. Evaluation of peptide-mediated transduction in human CD34+ cells, Hum Gene Ther. 15: 415-9, 2004.

Srinivas et al., "Membrane Interactions of Synthetic Peptides Corresponding to Amphipathic Helical Segments of the Human Immunodeficiency Virus Type-1 Envelope Glycoprotein", Journal of Biological Chemistry, 267:7121-7127, 1992.

Srinivas et al., "Calmodulin Antagonists Inhibit Human Immunodeficiency Virus-Induced Cell Fusion but Not Virus Replication,"AIDS Res. Hum. Retroviruses 10:1489, 1994.

Srinivas et al., J. Biol. Chem. Cytosolic domain of the human immunodeficiency virus envelope glycoproteins binds to calmodulin and inhibits calmodulin-regulated proteins, 268:22895, 1993.

Tam et al., "Disulfide Bond Formation in Peptides by Dimethyl Sulfoxide. Scope and Applications," J. Am. Chem. Soc. 113: 6657-6662, 1991.

Tencza et al., "Calmodulin-Binding Function of LLP Segments from the HIV Type 1 Transmembrane Protein Is Conserved among Natural Sequence Variants", AIDS Research & Human Retroviruses, 13: No. 3, 263-269, 1997.

Tencza et al., "Effect of Amino Acid Substitutions on Calmodulin Binding and Cytolytic Properties of the LLP-1 Peptide Segment of Human Immunodeficiency Virus Type 1 Transmembrane Protein", Journal of Virology, 69: 5199-5202, 1995.

Tencza et al., "Lentivirus-derived antimicrobial peptides: increased potency by sequence engineering and dimerization", Journal of Antimicrobial Chemotherapy, 44: 33-41, 1999.

Tencza et al., "Novel Antimicrobial Peptides Derived from Human Immunodeficiency Virus Type 1 and Other Lentivirus Transmembrane Proteins", Antimicrobial Agents & Chemotherapy, 41: 2394-2398, 1997.

Venable et al., "Theoretically Determined Three-Dimensional Structures for Amphipathic Segments of the HIV-1 gp41 Envelope Protein,"AIDS Res. Hum. Retroviruses 5:7, 1989.

von Eiff, C., Jansen, B., Kohnen, W. & Becker, K. Infections associated with medical devices: pathogenesis, management and prophylaxis. Drugs 65, 179-214 (2005).

Wachinger, M., et al., "Antimicrobial peptides melittin and cecropin inhibit replication of human immunodeficiency virus 1 by suppressing viral gene expression," (1998) Journal of General Virology 79: 731-40.

Wachinger, M., T. Saermark and V. Erfle, "Influence of amphipathic peptides on the HIV4 production in persistently infected T lymphoma cells," (1992) FEBS Letters 309:235-41.

Ward, N. et al., Inhibition of protein kinase C by a synthetic peptide, Cancer Lett. 88, 37-40 (1995).

Wheeler, D. S., Dunsmore, K. E., and Wong, H. R. Intracellular delivery of HSP70 using HIV-1 Tat protein transduction domain, Biochem Biophys Res Commun. 301: 54-9, 2003.

Wild et al., "A synthetic peptide inhibitor of human immunodeficiency virus replication: Correlation between solution structure and viral inhibition", Proc. Natl. Acad. Sci USA, 89: 10537-10541, 1992.

Yasin, B. et al. "Evaluation of the Inactivation of Infectious Herpes Simplex Virus by Host-Defense Peptides," (2000) European Journal of Clinical Microbiology &Infectious Diseases 19:187-94).

Yuan et al., "Characterization of the Calmodulin Binding Domain of SIV Transmembrane Glycoprotein by NMR and CD Spectroscopy", Biochemistry, 34: 10690-10696, 1995.

Zabner, J. et al., 1996, Adenovirus-mediated gene transfer to ciliated airway epithelia requires prolonged incubation time J. Virol. 70:6994-7003.

Zanetti, Gennaro and Romeo, "Cathelicidins: a novel protein family with a common propregion and a variable C-terminal antimicrobial domain", FEBS Letters, 374:1-5, 1995.

Zhang et al., Interactions of bacterial cationic peptide antibiotics with outer and cytoplasmic membranes of *Pseudomonas aeruginosa*. Antimicrob Agents Chemother. Dec. 2000;44(12):3317-21.

Zhang et al., Amphipathic domains in the C terminus of the transmembrane protein (gp41) permeabilize HIV-1 virions: a molecular mechanism underlying natural endogenous reverse transcription, Proc. Natl. Acad. Sci. USA 93:12519, 1996.

Zhibao et al. "Characterization of a Class of Cationic Peptides Able to Facilitate Efficient Protein Transduction in Vitro and in Vivo," Molecular Therapy vol. 2, No. 4, Oct. 2000, pp. 339-347.

Zhong et al. "Design and Synthesis of Amphipathic Antimicrobial Peptides, " Int. J. Pept. Prot. Res., 45:337, 1995.

Ziegler, A., Nervi, P., Durrenberger, M., and Seelig, J. The cationic cell-penetrating peptide CPP(TAT) derived from the HIV-1 protein TAT is rapidly transported into living fibroblasts: optical, biophysical, and metabolic evidence, Biochemistry. 44: 138-48, 2005.

* cited by examiner

LLP1:    RVIEVVQGACRAIRHIPRRIRQGLERIL
SA5:     RVIRVVQRACRAIRHIVRRIRQGLRRIL
LSA5:    RVIRVVQRACRAIRHIVRRIRQGLRRILRVV
WLSA5:   RWIRVVQRWCRAIRHIWRRIRQGLRRWLRVV

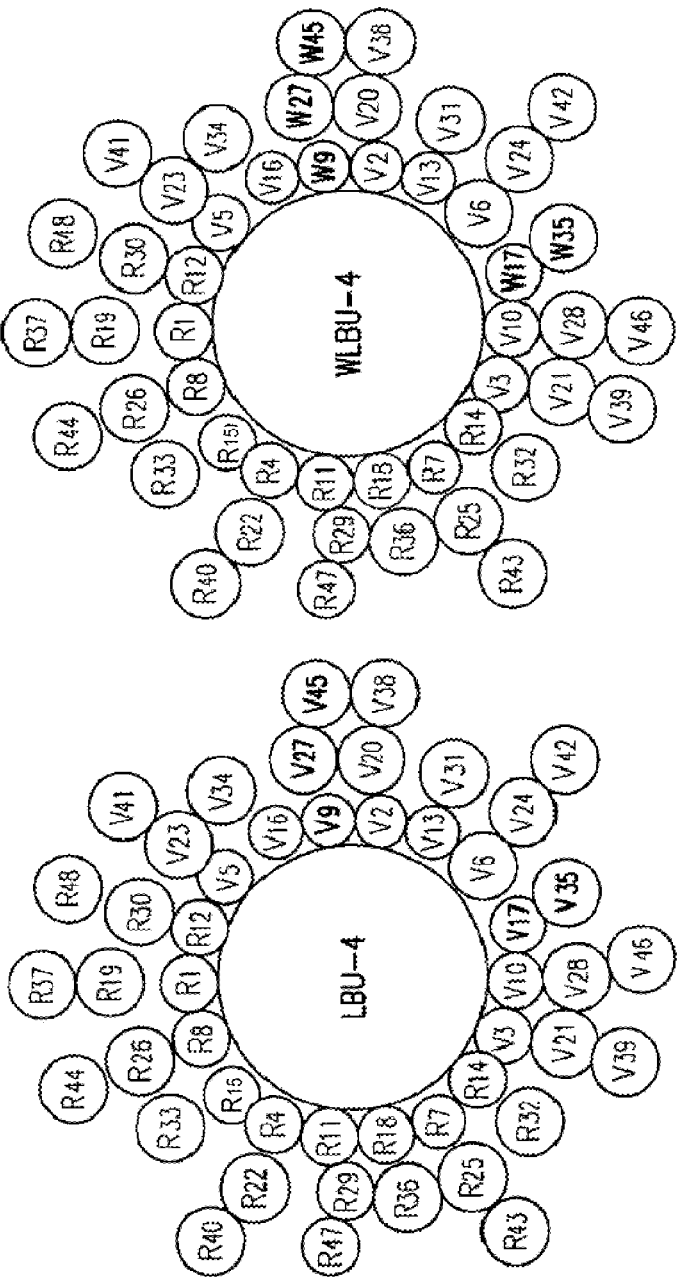

| | | |
|---|---|---|
| LBU-1 | RVVRVRRVVRRVVRRVVRR | (SEQ ID NO:4) |
| LBU-2 | RRVVRRVVRRVVRRVVRRVVRR | (SEQ ID NO:5) |
| LBU-3 | VRRVVRRVVRRVVRRVVRRVVRRVVRR | (SEQ ID NO:6) |
| LBU-3.5 | RRVVRRVVRRVVRRVVRRVVRRVVRRVVRR | (SEQ ID NO:7) |
| LBU-4 | RVVRVVRRVVRRVVRRVVRRVVRRVVRRVVRRVVRR | (SEQ ID NO:8) |
| WLBU-1 | RVWVRRVVRRWVRR | (SEQ ID NO:9) |
| WLBU-2 | RRWVRRWVRRWVRRWVRRWVRR | (SEQ ID NO:10) |
| WLBU-3 | VRRWVRRWVRRWVRRWVRRWVRRWVRR | (SEQ ID NO:11) |
| WLBU-4 | RVVRVVRRWVRRVVRRWVRRVVRRWVRRVVRR | (SEQ ID NO:12) |

Fig. 2

| Peptide | IC$_{50}$ (μM) | Toxicity (μM) |
|---|---|---|
| LBU1 | 30 | >50 |
| LBU2 | 0.78 | 1.6 |
| LBU3 | 0.38 | 1.6 |
| LBU4 | 1.56 | 0.78 |

Fig. 16

| Peptide | IC$_{50}$ (μM) | Toxicity (μM) |
|---|---|---|
| WLBU1 | 3.13 | >50 |
| WLBU2 | 0.38 | 1.6 |
| WLBU3 | 3.13 | 12.5 |
| WLBU4 | 3.13 | 6.25 |

Fig. 18

| Peptide | IC$_{50}$ (µM) | Toxicity (µM) |
|---|---|---|
| WR6 | 30 | >50 |
| WR18 | 3.13 | 12.5 |
| WR24 | 0.78 | 3.12 |

*Fig. 20*

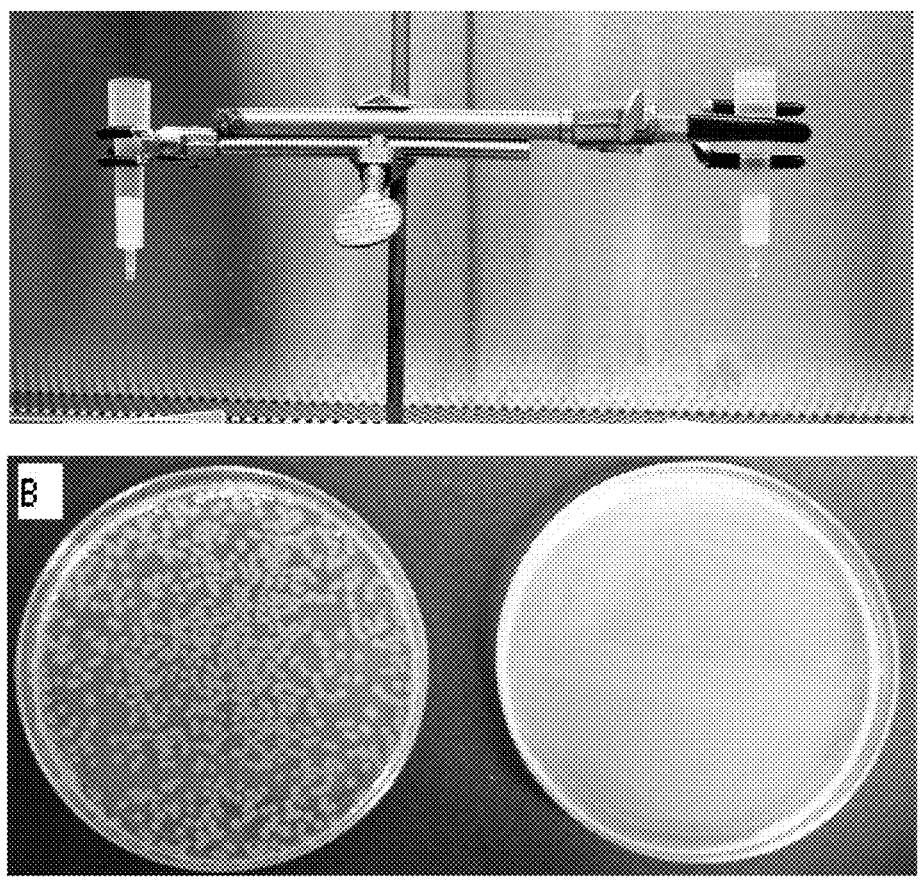
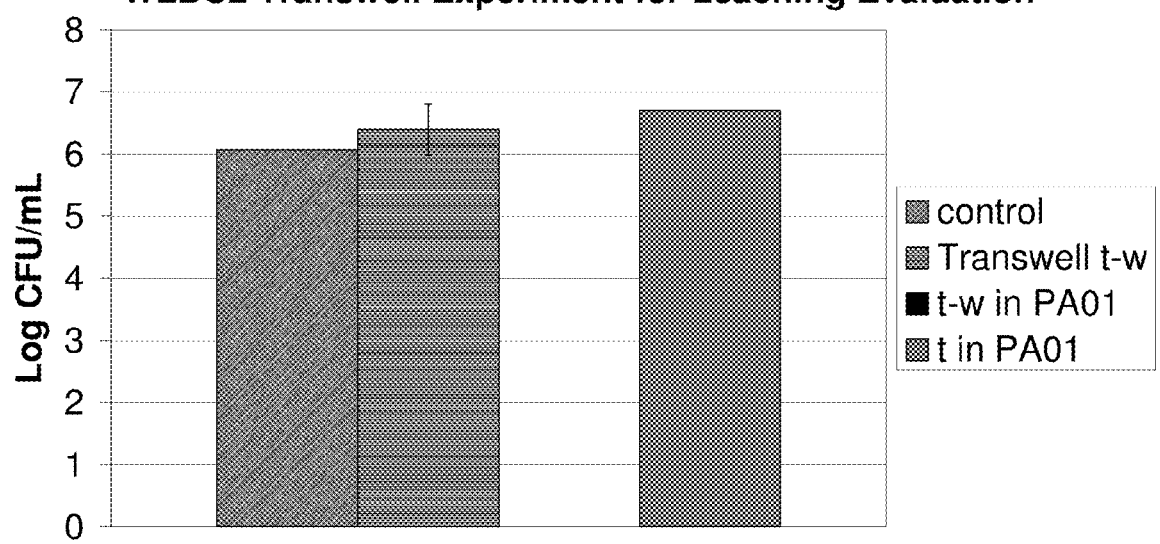
Fig. 22

Fig. 23

Effect of Peptide WLBU-2 on A/PR Plaque Formation

Fig. 24

VIRUS DERIVED ANTIMICROBIAL PEPTIDES

CROSS REFERENCE TO RELATED APPLICATIONS

This application claims the benefit under 35 U.S.C. §119(e) to U.S. Provisional Patent Application No. 60/959,453, filed Jul. 13, 2007, which is incorporated herein by reference in its entirety.

STATEMENT REGARDING FEDERAL FUNDING

The U.S. Government has a paid-up license in this invention and the right in limited circumstances to require the patent owner to license others on reasonable terms as provided for by the terms of Grant No. AI 39061-10, awarded by the National Institutes of Health.

The Sequence Listing associated with this application is filed in electronic format via EFS-Web and is hereby incorporated by reference into the specification in its entirety. The name of the text file containing the Sequence Listing is SEQLIST_144_ST25.txt. The size of the text file is 6927 KB, and the text file was created on Jul. 14, 2011.

The development of antimicrobial agents has led to a significant decrease in morbidity and mortality from infectious diseases in this century. This important public health contribution has been largely due to the widespread use of antibiotics that target specific nutrient, cell wall, DNA, RNA and protein biosynthetic pathways that are unique to pathogenic bacteria. However, in recent years the capacity to manage infectious diseases has been threatened by the emergence of bacterial strains that are no longer susceptible to currently available antimicrobial agents (see Files, 1999, *Chest.* 115: 3S-8S). Maintenance of the public health mandates that new antimicrobial agents need to be developed to counter these emerging resistant bacteria in order for effective infectious disease management procedures to remain in place.

A heterogeneous group of host-derived antimicrobial peptides have drawn attention as possible new therapeutic agents (see Hancock, R. E., 1999, *Drugs* 57:469-473). These peptides play an important role in innate vertebrate immunity against infection. For example, cationic antimicrobial peptides constitute as much as 18% by weight of total neutrophil protein. They are also found in high concentrations on damaged mucosal surfaces. In general these host-derived cationic peptides fit into one of four structural categories: (i) β-sheet structures that are stabilized by multiple disulfide bonds (e.g., human defensin-1), (ii) covalently stabilized loop structures (e.g., bactenecin), (iii) tryptophan (Trp)-rich, extended helical peptides (e.g., indolicidin), and (iv) amphipathic ∀-helices (e.g., the magainins and cecropins) (see Hwang and Vogel, 1998, *Biochemistry & Cell Biology* 76:235-246). Recently a new class of antimicrobial peptides, cathelicidins, which utilize all of these structural motifs and are clearly important in host defense against infection has been described (Ganz and Lehrer, 1997, *Current Opinion in Hematology* 4:53-58).

The cathelicidins are a remarkably diverse collection of peptides that derive from prepropeptides sharing a highly conserved N-terminal propeptide segment that have been described in humans, cattle, sheep, rabbits, mice, and pigs (see Hwang and Vogel, 1998, *Biochemistry & Cell Biology* 76:235-246). The conserved propeptide segment of approximately 100 amino acids shares sequence similarity with the porcine protein cathelin, a putative cysteine protease inhibitor, hence the family name. The C-terminal domain encodes an antimicrobial peptide motif similar to one of those described above, depending upon the host and tissue that it is associated with. Cathelicidins are stored in neutrophil granules as propeptides (lacking antimicrobial activity in this form), with neutrophil activation leading to elastase-mediated endoproteolytic cleavage and generation of the C-terminal antimicrobial peptide. The human cathelicidin, referred to alternatively as FALL-39, hCAPI8, LL-37, or CAMP, in its processed (active) form is a 37-amino acid amphiphilic a-helical cationic peptide (see Zanetti, Gennaro and Romeo, 1995, *FEBS Letters* 374:1-5). Expression of LL-37 has been detected in human neutrophils, testicular cells, respiratory epithelia, and in keratinocytes at sites of inflammation.

The amphipathic cationic peptides of the α-helical class demonstrate minimal bactericidal concentrations (MBCs) in the μg/mL range (levels equivalent to other antimicrobial agents) and are able to kill a broad range of gram-negative and gram-positive bacterial pathogens, including those that are highly resistant to multiple antibiotics (see Hancock, R. E., 1999, *Drugs* 57:469-473). The mechanism by which these peptides kill bacteria proceeds in a two step process, first binding to the negatively charged bacterial surface and second by driving these bound peptides into the bacterial membrane. The culmination of these processes ultimately results in the disruption of the bacterial membranes structural integrity. For gram-negative organisms, cationic antimicrobial peptides have the added advantage of binding lipopolysaccharide (LPS), thereby detoxifying its endotoxic activity (see Scott, Yan, and Hancock, 1999, *Infection & Immunity* 67:2005-2009). The hallmark of cationic α-helical antimicrobial peptides is their capacity to fold into an amphipathic secondary structure that presents a hydrophilic face with a net positive charge of at least +2. A number of different amino acid sequence combinations allow a peptide to achieve this characteristic structure. Consequently, hundreds of host-derived amphipathic cationic α-helical peptides have been described to date all showing limited sequence homology at the level of primary sequence comparison (see Hwang and Vogel, 1998, *Biochemistry & Cell Biology* 76:235-246). We hypothesize that the diversity of these peptides each have evolved to work in a specific environment and against a specific subset of microbial pathogens.

In contrast to host derived antimicrobial peptides, which have evolved with the express purpose of killing bacteria, a novel class of antimicrobial peptides derived from discrete segments of the lentiviral transmembrane (TM) protein cytoplasmic tail has been described that have not evolved for the same purpose as host-derived peptides (see Beary et al., 1998, *Journal of Peptide Research* 51:75-79; Comardelle et al., 1997, *AIDS Research & Human Retroviruses* 13:1525-1532; Miller et al., 1993, *AIDS Research & Human Retroviruses* 9:1057-1066; Miller et al., 1993, *Virology* 196:89-1000; Tencza et al., 1995, *Virology* 69:5199-5202; Tencza et al., 1997, *Antimicrobial Agents & Chemotherapy* 41:2394-2398; Tencza et al., 1997, *AIDS Research & Human Retroviruses* 13:263-269; Yuan et al., 1995, *Biochemistry* 34:10690-10696). These peptides are referred to as lentiviral lytic peptides (LLPs) with the prototypical LLP being LLP1 (amino acids 828-856 of the HIV-1 viral isolate HXB2R Env). LLP1 is derived from the 28-residues encoded by the C-terminal portion of the HIV-1 TM protein that, when modeled as an α-helix, demonstrates amphipathic character with clearly delineated cationic and hydrophobic faces. Among the many antimicrobial peptides currently described in the literature, LLP1 is most homologous structurally to the magainins and the human cathelicidin, LL37.

LLP 1 has been studied for its calmodulin-binding and antibacterial properties. LLP1 binds to host cell $Ca^{2+}$ saturated calmodulin with near nanomolar affinity and this property has been correlated with the inhibition of T-cell activation, suggesting that these peptides may dampen an inflammatory response (see Beary et al., 1998, *Journal of Peptide Research* 51:75-79; Miller et al., 1993, *AIDS Research & Human Retroviruses* 9:1057-1066; Tencza et al., 1995, *Virology* 69:5199-5202; Tencza et al., 1997, *AIDS Research & Human Retroviruses* 13:263-269; Yuan et al., 1995, *Biochemistry* 34:10690-10696). LLPI antibacterial activity has been investigated by surveying diverse gram-negative and -positive bacterial isolates. This analysis demonstrates that LLP1 has antibacterial activity which is equal to, or more potent than magainin-2. These isolates included methicillin and Vancomycin-resistant strains as well as other strains that were highly resistant to multiple antibiotics (see Tencza et al., 1997, *Antimicrobial Agents & Chemotherapy* 41:2394-2398). The lysis of bacteria by LLPI is rapid, nearly sterilizing a suspension of $1 \times 10^5$ colony-forming units of *Pseudomonas aeruginosa* or *Staphylococcus aureus* within 60 seconds of exposure (see Tencza et al., 1997, *Antimicrobial Agents & Chemotherapy* 41:2394-2398). The mechanism of LLP1 action is thought to perturb negatively charged bacterial membranes (Phalke, et al., Selective toxicity of engineered lentivirus lytic peptides in a CF airway cell model, *Peptides* (2003 August) 24(8): 1099-107), and to a lesser extent, neutral mammalian cell membranes. The predilection of the peptide for bacterial cells over mammalian cell membranes forms the basis for its selective toxicity.

Single amino acid changes in the LLP1 profoundly affect its calmodulin binding and antibacterial activity (see Tencza et al., 1995, *Virology* 69:5199-5202; Tencza et al., 1999, *Journal of Antimicrobial Chemotherapy* 44:33-41). In general, amino acid substitutions in the parent LLP1 sequence of basic residues to acidic residues decrease both calmodulin binding and bactericidal activities. Similarly, altering single hydrophobic residues to hydrophilic residues also decreased both of these activities. Furthermore, dimerization through disulfide bond formation of a single Cys found within the LLP1 parent sequence significantly increased its activity for *S. aureus* (see Tencza et al., 1999, *Journal of Antimicrobial Chemotherapy* 44:33-41). Finally, decreasing the length of the LLP1 dimer to 21 residues (peptide bis-TL1) reduced its red blood cell lysis activity without significantly reducing its antibacterial activity (see Tencza et al., 1999, *Journal of Antimicrobial Chemotherapy* 44:33-41). These data suggest that the LLP1 parent sequence can be engineered for increased potency and selectivity. The potential for this engineering forms the basis for compounds, compositions and methods described herein.

SUMMARY

Described herein are peptides having antimicrobial activity ("antimicrobial peptides"), compositions comprising the peptides and methods of making and using the peptides. In one embodiment, three antimicrobial peptides which are derived from, and are analogs of, the LLP1 peptide parent sequence corresponding to amino acids 828-856 of the HIV-1 viral isolate HXB2R Env have been described and include SA-5 (SEQ ID NO: 1), LSA-5 (SEQ ID NO: 2) and WLSA-5 (SEQ ID NO: 3) (see Table 1 below). The antimicrobial activity of other LLP1 peptide analogues has been previously described (see Tencza et al., 1999, *Journal of Antimicrobial Chemotherapy* 44:33-41, U.S. Pat. No. 5,714,577 of Montelaro et al. and U.S. Pat. No. 5,945,507 of Montelaro et al.).

In another embodiment, the antimicrobial peptides are LLP1 analogs having modifications based on the following principles: (i) optimizing amphipathicity, (ii) substituting arginine (Arg) on the charged face and/or valine (Val) or tryptophan (Trp) on the hydrophobic face with another amino acid, and (iii) increasing peptide length (referred to collectively herein as LBU peptides, e.g. LBU-1 (SEQ ID NO: 4); LBU-2 (SEQ ID NO: 5); LBU-3 (SEQ ID NO: 6); LBU-3.5 (SEQ ID NO: 7); LBU-4 (SEQ ID NO: 8); WLBU-1 (SEQ ID NO: 9); WLBU-2 (SEQ ID NO: 10); WLBU-3 (SEQ ID NO: 11); and WLBU-4 (SEQ ID NO: 12); see Table 1). The LBU peptides deviate greatly from the parent LLPI, for example, LBU-2 and LBU-3 deviate from the parent LLP1 sequence by greater than 90%.

TABLE 1

| | |
|---|---|
| SA-5: | RVIRV VQRAC RAIRH IVRRI RQGLR RIL<br>(SEQ ID NO: 1) |
| LSA-5: | RVIRV VQRAC RAIRH IVRRI RQGLR RILRV V<br>(SEQ ID NO: 2) |
| WLSA-5: | RWIRV VQRWC RAIRH IWRRI RQGLR RWLRV V<br>(SEQ ID NO: 3) |
| LBU-1: | RVVRV VRRVV RR<br>(SEQ ID NO: 4) |
| LBU-2: | RRVVR RVRRV VRRVV RVVRR VVRR<br>(SEQ ID NO: 5) |
| LBU-3: | VRRVV RRVVR VVRRV VRRVR RVVRR VVRVV RRVVRR<br>(SEQ ID NO: 6) |
| LBU-3.5: | RRVVR RVRRV VRRVV RVVRR VVRRV RRVVR RVVRV VRRVV RR<br>(SEQ ID NO: 7) |
| LBU-4: | RVVRV VRRVV RRVRR VVRRV VRVVR RVVRR VRRVV RRVVR VVRRV VRR<br>(SEQ ID NO: 8) |
| WLBU-1 | RVVRV VRRWV RR<br>(SEQ ID NO: 9) |
| WLBU-2 | RRWVR RVRRV WRRVV RVVRR WVRR<br>(SEQ ID NO: 10) |
| WLBU-3 | VRRVW RRVVR VVRRW VRRVR RVWRR VVRVV RRWVRR<br>(SEQ ID NO: 11) |
| WLBU-4 | RVVRV VRRWV RRVRR VWRRV VRVVR RWVRR VRRVW RRVVR VVRRW RVV<br>(SEQ ID NO: 12) |

Amino acid sequences provided herein are provided, left-to-right, from their N-terminus to their C-terminus. The LLP1 analogue peptides and the LBU peptides have a broader spectrum of activity (e.g., the ability to kill highly resistant bacteria) and increased potency (e.g., acting at lower molar concentrations to kill bacteria) when compared with previously described LLP1 analogs. The antimicrobial peptides described herein are highly inhibitory to microorganisms under physiologic salt concentrations, function in the presence of synovial fluid, and demonstrate only minimal toxicity in animal models. As a result, the antimicrobial agents may be defined as selective antimicrobial agents. The peptides are believed to function by disrupting bacterial membranes and are active when bound to a solid phase. The ability of these peptides to maintain activity when bound to a solid phase is a significant advantage over conventional antibiotics in that these peptides may be useful as coatings on, for example, sterile devices such as prostheses or catheters where it would be advantageous to prevent bacterial biofilm nucleation.

In another embodiment, several additional engineered cationic antimicrobial peptides (eCAP) are presented. These arginine/tryptophan-rich peptides are presented in Table 2 below. Several of these eCAP peptides showed significant activity in reducing HIV-1 infectivity of cells.

TABLE 2

| Peptide | Sequence | Comments |
|---|---|---|
| WR6 | RRWWRR | SEQ ID NO: 13 |
| WR12 | RWWRWWRRWWRR | SEQ ID NO: 14 |
| WR18 | WRRWWRRWWRWWRRWWRR | SEQ ID NO: 15 |
| WR24 | RRWWRRWRRWWRRWWRWWRRWWRR | SEQ ID NO: 16 |

Therefore, according to one non-limiting embodiment of the compounds, compositions and methods provided herein, a peptide is provided having an amino acid sequence selected from the group consisting of: RRWWRR (SEQ ID NO: 13); RWWRWWRRWWRR (SEQ ID NO: 14); WRRWWRRW-WRWWRRWWRR (SEQ ID NO: 15); and RRWWRRWR-RWWRRWWRWWRRWWRR (SEQ ID NO: 16). Compositions comprising the peptides also are provided, including compositions comprising any useful pharmaceutically acceptable excipient(s) or carrier(s).

In another embodiment, a method of neutralizing an enveloped virus is provided, the method comprises contacting the virus with one or more antimicrobial peptides chosen from SA-5 (SEQ ID NO: 1); WLSA-5 (SEQ ID NO: 3); LBU1 (SEQ ID NO: 4) LBU-2 (SEQ ID NO: 5); LBU-3 (SEQ ID NO: 6); LBU-3.5 (SEQ ID NO: 7); LBU-4, (SEQ ID NO: 8); WLBU-1 (SEQ ID NO: 9); WLBU-2 (SEQ ID NO: 10); WLBU-3 (SEQ ID NO: 11); and WLBU-4, (SEQ ID NO: 12), WR6 (SEQ ID NO: 13); WR12 (SEQ ID NO: 14); WR18 (SEQ ID NO: 15); and WR24 (SEQ ID NO: 16) in an amount effective to neutralize the enveloped virus. Specific, non-limiting examples of enveloped viruses include: poxvirus, herpesvirus, hepadnavirus, rhabdovirus, baculovirus, orthomyxovirus, paramyxovirus, retrovirus, togavirus, bunyavirus and flavivirus. In one embodiment, the enveloped virus is a lentivirus, such as a Human Immunodeficiency Virus, such as HIV-1. In one embodiment, the one or more antimicrobial peptides are chosen from WR6 (SEQ ID NO: 13); WR12 (SEQ ID NO: 14); WR18 (SEQ ID NO: 15); and WR24 (SEQ ID NO: 16). The antimicrobial peptide may be administered to a subject in an amount effective to prevent or treat an enveloped virus infection, thereby preventing or treating an enveloped virus infection in the subject.

In a related embodiment, a method of neutralizing an orthomyxovirus, such as an influenza virus, is provided. The method comprising contacting the virus with one or more antimicrobial peptides chosen from SA-5 (SEQ ID NO: 1); LSA-5 (SEQ ID NO: 2); WLSA-5 (SEQ ID NO: 3); LBU1 (SEQ ID NO: 4); LBU-2 (SEQ ID NO: 5); LBU-3 (SEQ ID NO: 6); LBU-3.5 (SEQ ID NO: 7); LBU-4, (SEQ ID NO: 8); WLBU-1 (SEQ ID NO: 9); WLBU-2 (SEQ ID NO: 10); WLBU-3 (SEQ ID NO: 11); and WLBU-4, (SEQ ID NO: 12), WR6 (SEQ ID NO: 13); WR12 (SEQ ID NO: 14); WR18 (SEQ ID NO: 15); and WR24 (SEQ ID NO: 16) in an amount effective to neutralize the orthomyxovirus. In one embodiment, the antimicrobial peptide is WLBU-2 (SEQ ID NO: 10). The antimicrobial peptide may be administered to a subject in an amount effective to prevent or treat an infection by an orthomyxovirus, thereby preventing or treating an infection by an orthomyxovirus. In one embodiment, the one or more antimicrobial peptides is chosen from WR6 (SEQ ID NO: 13); WR12 (SEQ ID NO: 14); WR18 (SEQ ID NO: 15); and WR24 (SEQ ID NO: 16).

In yet another embodiment, a method of killing a Bacillus anthracis bacterium, vegetative form is provided. The method comprising contacting the bacterium with one or more antimicrobial peptides chosen from SA-5 (SEQ ID NO: 1); LSA-5 (SEQ ID NO: 2); WLSA-5 (SEQ ID NO: 3); LBU1 (SEQ ID NO: 4); LBU-2 (SEQ ID NO: 5); LBU-3 (SEQ ID NO: 6); LBU-3.5 (SEQ ID NO: 7); LBU-4, (SEQ ID NO: 8); WLBU-1 (SEQ ID NO: 9); WLBU-2 (SEQ ID NO: 10); WLBU-3 (SEQ ID NO: 11); and WLBU-4, (SEQ ID NO: 12), WR6 (SEQ ID NO: 13); WR12 (SEQ ID NO: 14); WR18 (SEQ ID NO: 15); and WR24 (SEQ ID NO: 16) in an amount effective to kill the bacterium. In one embodiment, the antimicrobial peptide is one or both of WLBU-1 (SEQ ID NO: 9) and WLBU-2 (SEQ ID NO: 10). The antimicrobial peptide may be administered to a subject in an amount effective to prevent or treat a B. anthracis infection, thereby preventing or treating a B. anthracis infection. In one embodiment, the one or more antimicrobial peptides is chosen from WR6 (SEQ ID NO: 13); WR12 (SEQ ID NO: 14); WR18 (SEQ ID NO: 15); and WR24 (SEQ ID NO: 16).

In another embodiment, a method of killing a fungus of the Genera Candida or Cryptococcus, is provided. The method comprising contacting the fungus with one or more antimicrobial peptides chosen from SA-5 (SEQ ID NO: 1); LSA-5 (SEQ ID NO: 2); WLSA-5 (SEQ ID NO: 3); LBU1 (SEQ ID NO: 4); LBU-2 (SEQ ID NO: 5); LBU-3 (SEQ ID NO: 6); LBU-3.5 (SEQ ID NO: 7); LBU-4, (SEQ ID NO: 8); WLBU-1 (SEQ ID NO: 9); WLBU-2 (SEQ ID NO: 10); WLBU-3 (SEQ ID NO: 11); and WLBU-4, (SEQ ID NO: 12), WR6 (SEQ ID NO: 13); WR12 (SEQ ID NO: 14); WR18 (SEQ ID NO: 15); and WR24 (SEQ ID NO: 16) in an amount effective to kill the fungus. In one embodiment, the antimicrobial peptide is one or both of WLBU-1 (SEQ ID NO: 9) and WLBU-2 (SEQ ID NO: 10). In another embodiment, the antimicrobial peptides are chosen from WR6 (SEQ ID NO: 13); WR12 (SEQ ID NO: 14); WR18 (SEQ ID NO: 15); and WR24 (SEQ ID NO: 16). The antimicrobial peptide may be administered to a subject in an amount effective to prevent or treat a Candida or Cryptococcus infection, thereby preventing or treating a Candida or Cryptococcus infection. In one embodiment, the fungus is one or more of C. albicans, C. krusei, C. parapsilosis, C. tropicalis, C. galbrata, and C. lusitaniae.

In another embodiment, the antimicrobial peptides are attached (typically covalently and typically by a peptide bond) to a membrane translocation element, such as a peptide transduction domain. Therefore, according to this embodiment, a compound is provided comprising an antimicrobial peptide chosen from SA-5 (SEQ ID NO: 1); LSA-5 (SEQ ID NO: 2); WLSA-5 (SEQ ID NO: 3); LBU1 (SEQ ID NO: 4); LBU-2 (SEQ ID NO: 5); LBU-3 (SEQ ID NO: 6); LBU-3.5 (SEQ ID NO: 7); LBU-4, (SEQ ID NO: 8); WLBU-1 (SEQ ID NO: 9); WLBU-2 (SEQ ID NO: 10); WLBU-3 (SEQ ID NO: 11); and WLBU-4, (SEQ ID NO: 12), WR6 (SEQ ID NO: 13); WR12 (SEQ ID NO: 14); WR18 (SEQ ID NO: 15); and WR24 (SEQ ID NO: 16) attached to a membrane translocation domain. The membrane translocation domain may be a peptide transduction domain. In one embodiment, peptide transduction domain comprises the amino acid sequence RRQRRTSKLMKR (SEQ ID NO: 17). In another, embodiment, the antimicrobial peptide is one of WLBU-1 (SEQ ID NO: 8) and WLBU-2 (SEQ ID NO: 9). In one specific example, the compound has the amino acid sequence RRQR-RTSKLMKRRRWVRRVRRVWRVVRVVRRWVRR (SEQ ID NO: 18). Compositions comprising the compound also are provides, including compositions comprising any useful pharmaceutically acceptable excipient(s) or carrier(s).

A solid phase substrate comprising at least one peptide chosen from: WR6 (SEQ ID NO: 13); WR12 (SEQ ID NO: 14); WR18 (SEQ ID NO: 15); WR24 (SEQ ID NO: 16); and a compound comprising an antimicrobial peptide chosen from SA-5 (SEQ ID NO: 1); LSA-5 (SEQ ID NO: 2); WLSA-5 (SEQ ID NO: 3); LBU-1 (SEQ ID NO: 4); LBU-2 (SEQ ID NO: 5); LBU-3 (SEQ ID NO: 6); LBU-3.5 (SEQ ID NO: 7); LBU-4, (SEQ ID NO: 8); WLBU-1 (SEQ ID NO: 9); WLBU-2 (SEQ ID NO: 10); WLBU-3 (SEQ ID NO: 11); and WLBU-4, (SEQ ID NO: 12); WR6 (SEQ ID NO: 13); WR12 (SEQ ID NO: 14); WR18 (SEQ ID NO: 15); and WR24 (SEQ ID NO: 16), attached to a membrane translocation domain, such as any membrane translocation domain described herein. The solid phase substrate can be a prosthetic device, such as a prosthetic joint, or a catheter or cannula. In one embodiment, the peptide is chosen from one or more of WR6 (SEQ ID NO: 13); WR12 (SEQ ID NO: 14); WR18 (SEQ ID NO: 15); WR24 (SEQ ID NO: 16); and a compound comprising an antimicrobial peptide chosen from WR6 (SEQ ID NO: 13); WR12 (SEQ ID NO: 14); WR18 (SEQ ID NO: 15); and WR24 (SEQ ID NO: 16), attached to a membrane translocation domain.

In another non-limiting embodiment, an isolated and purified peptide-cargo complex is provided. The peptide-cargo complex comprises a cargo and a peptide chosen from WR6 (SEQ ID NO: 13); WR12 (SEQ ID NO: 14); WR18 (SEQ ID NO: 15); WR24 (SEQ ID NO: 16); and a compound comprising an antimicrobial peptide chosen from SA-5 (SEQ ID NO: 1); LSA-5 (SEQ ID NO: 2); WLSA-5 (SEQ ID NO: 3); LBU-1 (SEQ ID NO: 4); LBU-2 (SEQ ID NO: 5); LBU-3 (SEQ ID NO: 6); LBU-3.5 (SEQ ID NO: 7); LBU-4, (SEQ ID NO: 8); WLBU-1 (SEQ ID NO: 9); WLBU-2 (SEQ ID NO: 10); WLBU-3 (SEQ ID NO: 11); and WLBU-4, (SEQ ID NO: 12), WR6 (SEQ ID NO: 13); WR12 (SEQ ID NO: 14); WR18 (SEQ ID NO: 15); and WR24 (SEQ ID NO: 16), attached to a membrane translocation domain, such as any membrane translocation domain described herein. In one embodiment, the peptide has antimicrobial activity and the cargo increases the antimicrobial activity of the peptide. In another embodiment, the peptide is chosen from one of WR6 (SEQ ID NO: 13); WR12 (SEQ ID NO: 14); WR18 (SEQ ID NO: 15); and WR24 (SEQ ID NO: 16); and a compound comprising an antimicrobial peptide chosen from WR6 (SEQ ID NO: 13); WR12 (SEQ ID NO: 14); WR18 (SEQ ID NO: 15); and WR24 (SEQ ID NO: 16), attached to a membrane translocation domain.

BRIEF DESCRIPTION OF THE DRAWINGS

The present invention may be better understood with reference to the attached drawings of which—

FIG. 2 shows the sequences of the engineered LBU and WLBU peptides (SEQ ID NOS: 4-12).

FIG. 16 is a chart showing the $IC_{50}$ and toxicity values for LBU peptides.

FIG. 18 is a chart showing the $IC_{50}$ and toxicity values for WLBU peptides.

FIG. 20 is a chart showing the IC50 and toxicity values for WR peptides.

FIG. 22 illustrates how the experiment was performed with WLBU-2 (SEQ ID NO: 10) bound to Affigel. The columns to which the bacteria were applied are shown in the upper panel. The bacterial growth on appropriate bacteriologic medium is shown in the center panel. The fact that WLBU-2 was covalently bound and not able to diffuse across a dialysis membrane with a molecular mass cut off of 30,000 MW is shown in the graph of the lower panel.

FIG. 23 shows scanning electron microscopy (SEM) analysis of P. aeruginosa exposed to SCPC material that does not contain WLBU-2 (SEQ ID NO: 10) (a) or that contains WLBU-2 (b). What is clear from this analysis is that the presence of WLBU-2 in a bone-resorbable material is that the cationic peptide, WLBU-2, recruits bacteria such as P. aeruginosa to the surface. Upon binding our data indicate that these organisms beginning to spill beta-galactosidase into the media, an indicator of bacterial cell lysis.

FIG. 24 is a graph illustrating a dose-dependent decrease in infectious virus plaque formation for seasonal influenza virus.

DETAILED DESCRIPTION

Figure 1:
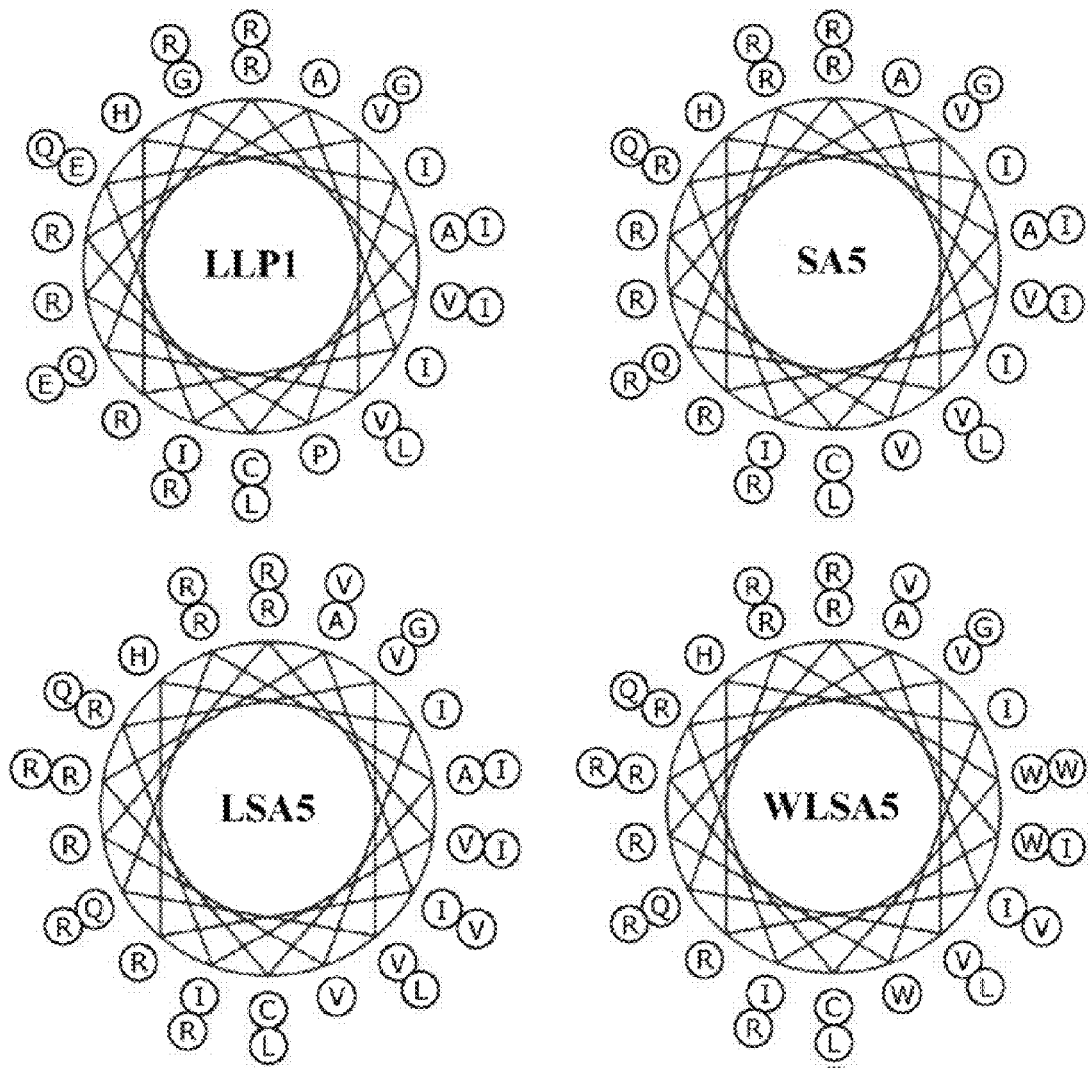
FIG. 1 shows the sequences of the engineered LLPs (eLLPs) SA-5 (SEQ ID NO: 1), LSA-5 (SEQ ID NO: 2), and WLSA-5 (SEQ ID NO: 3) relative to the parent LLP1 sequence (SEQ ID NO: 19).

Based on studies of lentiviral lytic peptide 1 (LLP1) of HIV-1 transmembrane glycoprotein gp41 and other host-derived peptides indicate that antimicrobial properties of membrane-active peptides it is apparent that their antimicrobial activity is markedly influenced by their cationic, hydrophobic, and amphipathic properties. Common themes, such as Arg composition of the cationic face of an amphipathic helix and the importance of maintaining a hydrophobic face have been deduced from these observations. These studies suggest that a peptide with these structural properties can be derived de novo using a limited subset of amino acids that are strategically positioned. Multimers of a six-residue lytic base unit (LBU) peptide composed only of Arg, Val, and Trp residues aligned to form idealized amphipathic helices were designed. Bacterial killing assays and circular dichroism analyses revealed a strong correlation between antibacterial activity, peptide length, and propensity to form a helix in solvent mimicking the environment of a membrane. All of these peptides demonstrated antimicrobial activity. The 24-residue WLBU-2 (SEQ ID NO: 10) peptide was active at physiologic NaCl concentrations against Staphylococcus aureus and mucoid and non-mucoid strains of Pseudomonas aeruginosa. Further, WLBU-2 (SEQ ID NO: 10) displayed the highest antibacterial selectivity of all peptides evaluated using a co-culture model of P. aeruginosa and primary human skin fibroblasts. These findings provide fundamental information toward the de novo design of an antimicrobial peptide useful for the management of infectious diseases (Deslouches et al, 2005).

As an extension of these findings, a murine model of P. aeruginosa was established. The intravenous administration of WLBU-2 (SEQ ID NO: 10) demonstrated protection against a lethal challenge of P. aeruginosa (Deslouches et al. 2007). These findings were very surprising since all evidence suggest that antimicrobial peptides would only be effective if topically administered.

Since reporting the antibacterial activity of the LLP1 (see Tencza et al., 1997, Antimicrobial Agents & Chemotherapy 41:2394-2398), a number of different LLP1 analogues have been prepared (see, e.g. U.S. Pat. No. 5,714,577 of Montelaro et al. and U.S. Pat. No. 5,945,507 of Montelaro et al. and Tencza et al., 1999, Journal of Antimicrobial Chemotherapy 44:33041) by manipulating the parent sequence to increase potency (i.e., increase their molar bacterial killing activity) and broaden the spectrum of activity against clinical isolates. This has been achieved by optimizing the hydrophilic and hydrophobic faces of the modeled α-helix. Three antimicrobial peptides are described herein, which are LLP1 peptide analogs, SA-5 (SEQ ID NO: 1), LSA-5 (SEQ ID NO: 2) and WLSA-5 (SEQ ID NO: 3) (see Table 1 above). In addition, described herein are antimicrobial peptides which are LLP1 analogs having modifications based on the following principles: (i) optimizing amphipathicity, (ii) substituting with Arg on the charged face and Val on the hydrophobic face, (iii) increasing peptide length, and (iv) periodically substituting Val with Trp (referred to collectively herein as LBU peptides, e.g. LBU-1 (SEQ ID NO: 4); LBU-2 (SEQ ID NO: 5); LBU-3 (SEQ ID NO: 6); LBU-3.5 (SEQ ID NO: 7); LBU-4 (SEQ ID NO: 8); WLBU-1 (SEQ ID NO: 9); WLBU-2 (SEQ ID NO: 10); WLBU-3 (SEQ ID NO: 11); and WLBU-4 (SEQ ID NO: 12), see Table 1). The compositions of SA-5 (SEQ ID NO: 1), LSA-5 (SEQ ID NO: 2), WLSA-5 (SEQ ID NO: 3), LBU-4 (SEQ ID NO: 8) and WLBU-4 (SEQ ID NO: 12) are described in FIGS. 1 and 2 with regard to their primary sequences when modeled as an α-helical structure and compared with the parent peptide LLP1.

The peptide designated SA-5 substitutes three arginine residues for a glycine (Gly) and two glutamic acid (Glu) residues that model on the hydrophilic face of the LLP1 parent sequence, and a proline (Pro) to valine (Val) substitution that models on the hydrophobic face of this sequence. The rationale underlying the generation of this peptide is to optimize the cationic, amphipathic character of the original LLP1 sequence.

The peptide designated LSA-5 contrasts previous reports describing the potency of truncated derivatives of LLP1 (see Tencza et al., 1999, Journal of Antimicrobial Chemotherapy 44:33041) by investigating the activity of LLP derivatives of increased length. LSA-5 extends the length of the modeled α-helix by one turn and preserves the amphipathic, Arg-rich cationic character.

Based on the structural studies of Hwang and Vogel (Biochemistry & Cell Biology 76:235-246 (1998)), Trp residues have been shown to intercalate optimally into bacterial membranes. However, the fact that Trp may intercalate into biologic membranes does not imply that specific peptides containing Trp will selectively disrupt bacterial membranes. The WLSA-5 (SEQ ID NO: 3) peptide was derived by replacing four residues on the hydrophobic face of LSA-5 (SEQ ID NO: 2) with Trp residues.

In addition, LLP analog peptides are described herein comprising modifications based on the following principles: (i) optimizing amphipathicity, (ii) substituting with Arg on the charged face and Val on the hydrophobic face, (iii) increasing peptide length, and (iv) periodically substituting Val with Trp. Peptides modified according to these principles are referred to herein as the Lytic Base Unit (LBU) peptides. For example, the peptides LBU-2 and LBU-3 were formulated as a polymer of Arg and Val residues designed to create maximal amphipathic α-helical character with a length of at least 24 residues.

Additional peptides described herein are Arg-Trp rich peptides having the following sequences: WR6: RRWWRR (SEQ ID: 13); WR12: RWWRWWRRWWRR (SEQ ID NO: 14); WR18: WRRWWRRWWRWWRRWWRR (SEQ ID NO: 15) and WR24: RRWWRRWRRWWRRWWRWWR-RWWRR (SEQ ID NO: 16). These peptides, referred to as eCAPs (engineered cationic antimicrobial peptides) are based on the LBU series of peptides, wherein all of the valines are replaced by tryptophans.

The antimicrobial activity of the peptides described herein is discussed below in the examples.

The activity of the antimicrobial peptides SA-5 (SEQ ID NO: 1), LSA-5 (SEQ ID NO: 2), WLSA-5 (SEQ ID NO: 3), LBU-1 (SEQ ID NO: 4); LBU-2 (SEQ ID NO: 5), LBU-3 (SEQ ID NO: 6), LBU-3.5 (SEQ ID NO: 7), LBU-4 (SEQ ID NO: 8), WLBU-1 (SEQ ID NO: 9), WLBU-2 (SEQ ID NO: 10), WLBU-3 (SEQ ID NO: 11) and WLBU-4 (SEQ ID NO: 12) against a range of bacteria including *Staphylococcus aureus*, methicillin-resistant *S. aureus*, and *Pseudomonas aeruginosa* is summarized in Table 3 below.

Table 3 indicates the MBCs of peptides expressed in millimolar (mM) concentrations. These results demonstrate the antimicrobial potency of these antimicrobial peptides. The activity of these peptides compares favorably with other antibacterial peptides which may have equal or decreased activity (as indicated by a higher minimum bactericidal concentration (MBC, see Example 2 below). Table 3 also indicates the MBCs of antimicrobial peptides described herein against different organisms and at different salt conditions.

tide" refers to an oligomer of at least two contiguous amino acids, linked together by a peptide bond. The term "kill" and like terms, refers to the ability of an antimicrobial peptide to inhibit or destroy growth of a cellular (e.g., self-replicating) microbe, such as, without limitation, a bacteria or fungus, for example, by reducing a number of colony-forming units of the cellular microbe in a bacteria culture or colony, or to inhibit growth rate of a colony or culture of cells. Likewise, with reference to virus particles or virions (e.g., non-self-replicating), the term "neutralize" refers to a reduction of infectivity of a single virion and to overall infectivity (e.g., a reduction in the number of infectious units (IU) or plaque-forming units (PFU)) of a sample of virus particles. Non-limiting examples of killing of bacteria or fungi, and neutralization of virions, and methods of testing for such killing or neutralization are provided in the Examples below.

The term "treatment" and like terms, in the context of the antimicrobial peptides described herein, refers to the action and ability of a peptide to reduce, remove, destroy, ameliorate, and/or stabilize an infection in a subject, such as a human or veterinary patient. "Prevention" and like terms in the context of the present disclosure refers to administration of a peptide to a subject, prior to or during exposure to a microbe with the goal of reducing or preventing infectivity of the microbe in the subject. Administration of a peptide during an incubation period, or suspected incubation period of a virus or other microbe (e.g., after possible exposure to HIV or rabies), is a preventative use of the peptides described herein. The ability and effective dosage and treatment regimen for a pep-

TABLE 3

| Peptide | *Psuedomonas aeruginosa* | | *Staphylococcus aureus* | | Methicillin Resistant *S. aureus* | |
|---|---|---|---|---|---|---|
| | 0 mM NaCl | 150 mM NaCl | 0 mM NaCl | 150 mM NaCl | 0 mM NaCl | 150 mM NaCl |
| LLP1 | 1000 | 1000 | 8000 | 16000 | 16000 | — |
| SA-5 | 1000 | 1000 | 1000 | — | — | — |
| LSA-5 | 800 | 800 | 1000 | 1000 | 150 | — |
| WLSA-5 | 1000 | 1000 | 1000 | 1000 | 150 | — |
| LBU-2 | 1500 | 800 | 1500 | >100,000 | — | — |
| LBU-3 | 1500 | 800 | 1500 | 1500 | — | — |
| LBU-3.5 | 400 | 400 | 1000 | 600 | 1500 | 200 |
| LBU-4 | 800 | 400 | 800 | 800 | — | — |
| WLBU-1 | 400 | 2500 | 30,000 | 10,000 | 50,000 | 50,000 |
| WLBU-2 | 200 | 100 | 1000 | 600 | 200 | 100 |
| WLBU-3 | 1500 | 800 | 3,000 | 600 | 400 | 100 |
| WLBU-4 | 1500 | 400 | 3,000 | 600 | 1500 | 200 |

The antimicrobial peptides described herein exhibit antimicrobial activity against diverse microorganisms, and are analogs of the LLP1 peptide corresponding to amino acids 828-856 of the HIV-1 viral isolate HXB2R Env TM. The peptides comprise Arg-rich sequences, which, when modeled for secondary structure, display high amphipathicity and hydrophobic moment. The peptides are highly inhibitory to microorganisms, but significantly less toxic to mammalian cells. As a result, these peptides can be characterized as selective antimicrobial agents. In addition, the peptides described herein include LLP1 peptide analogs comprising modifications based on the following principles: (i) optimizing amphipathicity, (ii) substituting Arg on the charged face and/or Val or Trp on the hydrophobic face, and (iii) increasing peptide length, collectively referred to herein as LBU peptides.

As used herein, the term "antimicrobial" refers to the ability of the antimicrobial peptides described herein to prevent, inhibit or destroy the growth of microbes such as bacteria, fungi, protozoa and viruses. As used herein, the term "peptide in the treatment or prevention of an infection typically is determined by studies of a statistically-relevant population of subjects, and is determined as compared to a placebo or other negative control.

Antimicrobial peptides described herein are structural and functional analogs of the parent peptide, LLP1, that exhibits selective toxicity for microorganisms. As used herein, the term "analog" refers to a peptide which contains substitutions, rearrangements, deletions, additions and/or chemical modifications in the amino acid sequence of parent peptide, and retains the structural and functional properties of the parent peptide. These also include the LBUs.

The antimicrobial peptides described herein lack significant primary sequence homology to known antimicrobial non-LLP peptides (e.g., magainins or the cathelicidins). The peptides are rich in positively charged (Arg) residues and are predicted to form an amphipathic α-helix. The amphipathic α-helix imparts a unique and potent antimicrobial activity to the antimicrobial peptides described herein. The structural properties defining certain antimicrobial peptides described herein include, inter alia, the ability to form three-dimensional amphipathic α-helical structures (Eisenberg and Wesson, 1990, *Biopolymers* 29:171-177). The amphipathic α-helical structure comprises residues arranged such that 3.6 amino acid residues complete one turn of the helix. Based on this arrangement, derived from well known protein folding constraints, an estimate of amphipathicity may be made by examination of the amino acid sequence.

In one embodiment, optimization of this "ideal" amphipathic α-helical motif is one of the principles used to generate the antimicrobial peptides described herein. In another embodiment, the substitution of Arg residues on the hydrophilic face and Trp or Val residues on the hydrophobic face is one of the principles used to generate the antimicrobial peptides described herein. The antimicrobial peptides described herein may further contain Ala, Gly, Ile, or Phe and other D- or L-amino acid residues that can be tolerated within a general amphipathic α-helical structure. These residues may impart or facilitate a structure, which enhances the potency and selectivity of a peptide in a manner that can only be determined empirically. Some antimicrobial peptides described herein contain one Cys which, by virtue of its capacity to form a disulfide bond, can confer increased potency to a peptide containing such a residue as a disulfide-linked dimeric peptide (e.g., bis-eLLP). The position of the Cys lies on the interface of the hydrophilic and hydrophobic faces of the amphipathic a-helical structure when modeled as such. The placement of such Cys residues would not be obvious to someone skilled in the art and must be determined empirically. This may be accomplished by a person of skill in the art without undue experimentation, e.g. by using a computer modeling of peptide structure. For example, Computer modeling programs such as "Helical Wheel" (Genetics Computer Group, Madison, Wis.) may be used to design the antimicrobial peptides described herein. In a further embodiment, the length of the antimicrobial peptides described herein may be increased to improve their antimicrobial activity.

The antimicrobial peptides described herein are unique in their functional properties. The unique structure of the antimicrobial peptides imparts high potency while maintaining selectivity for bacteria. The potency of the antimicrobial peptides compares very favorably to that of magainin or cathelicidin. Tehantimicrobial peptides rapidly kill both gram-positive and gram-negative bacteria, demonstrating a broad spectrum of activity including but not limited to, gram-positive bacteria such as *Listeria monocytogenes, Bacillus subtilis, Enterococcus faecalis* (including vancomycin-sensitive (VSEF) and vancomycin-resistant (VREF) strains), *Enterococcus faecium* (including vancomycin-sensitive (VSEF) and vancomycin-resistant (VREF) strains), *Staphylococcus aureus* (including methicillin-sensitive (MSSA) and methicillin-resistant (MRSA) strains), *Staphylococcus epidermidis* (including methicillin-sensitive (MSSE) and methicillin-resistant (MRSE) strains), *Staphylococcus salivarius, Corynebacterium minutissium, Corynebacterium pseudodiphtheriae, Corynebacterium stratium, Corynebacterium* group G1, *Corynebacterium* group G2, *Streptococcus pneumonia* (including penicillin-resistant (PSRP) strains), *Streptococcus mitis* and *Streptococcus sanguis*; Gram-negative bacteria including *Escherichia coli, Klebsiella pneumoniae, Pseudomonas aeruginosa, Burkholderia cepacia, Serratia marcescens, Haemophilus influenzae, Moraxella* sp., *Neisseria meningitidis, Neisseria gonorrhoeae, Salmonella typhimurium, Actinomyces* spp., *Porphyromonas* spp., *Prevotella melaminogenicus, Helicobacter pylori, Helicobacter felis*, and *Campylobacter jejuni*. Functional properties also include selective antimicrobial activity with minimal toxicity for mammalian cells. Therefore, based on the teachings and guidance herein, one skilled in the art can readily design antimicrobial peptides that have a desired potency and selectivity.

Analogs of particular antimicrobial peptides and/or other cytolytic peptides are within the scope of the present invention. The analogs retain the structural and functional properties described herein. In another embodiment of the antimicrobial peptides described herein, D-amino acids may be used in place of L-amino acids and may provide increased metabolic stability, since peptides containing D-amino acids are resistant to mammalian proteases, which generally cleave peptides composed of L-amino acids. For example, cecropin analogs containing D-amino acids exhibit antibacterial activity (Merrifield et al., Antimicrobial Peptides, Ciba Foundation Symposium, Wiley, Chichester, 5-26, 1994). Peptide analogs that are longer than the LLP1 parent peptide are described herein. These peptides may be more potent than the LLP1 parent sequence when compared on a molar basis, and demonstrate a broader spectrum of activity. As discussed above, the inclusion of a Cys residue in an antimicrobial peptide is useful in facilitating the formation of intramolecular or intermolecular disulfide bonds that can stabilize a dimeric peptide and improves antimicrobial potency against certain microbial pathogens such as *S. aureus*.

The antimicrobial peptides described herein may be highly active under high salt conditions and in biologic fluids (see Example 4 and FIGS. 3-6). The ability of the peptides to maintain activity in physiological NaCl concentrations allows the peptides to exhibit antimicrobial activity within physiologic fluids of vertebrate hosts.

Peptides described herein can be synthesized by classic lipid phase or solid phase peptide synthesis methods, including Fmoc and t-Boc chemistries may be utilized. In one embodiment, Merrifield solid phase synthesis techniques are used, using manual or automated procedures known to those skilled in the art, e.g., as described by Miller et al. (*AIDS Research & Human Retroviruses* 7:511-519 (1991), using an Advanced Chemtech model 200 (Advanced Chemtech, Louisville, Ky.), or using a Millipore 9050+ (Millipore, Bedford, Mass.) automated synthesizer with Fmoc synthesis protocols (see Fontenot et al., 1991, *Peptide Research* 4:19-25), or other available instrumentation. Synthetic peptides prepared by any method can be purified by, for example, gel filtration chromatography and reverse-phase column/HPLC.

Figure 27:
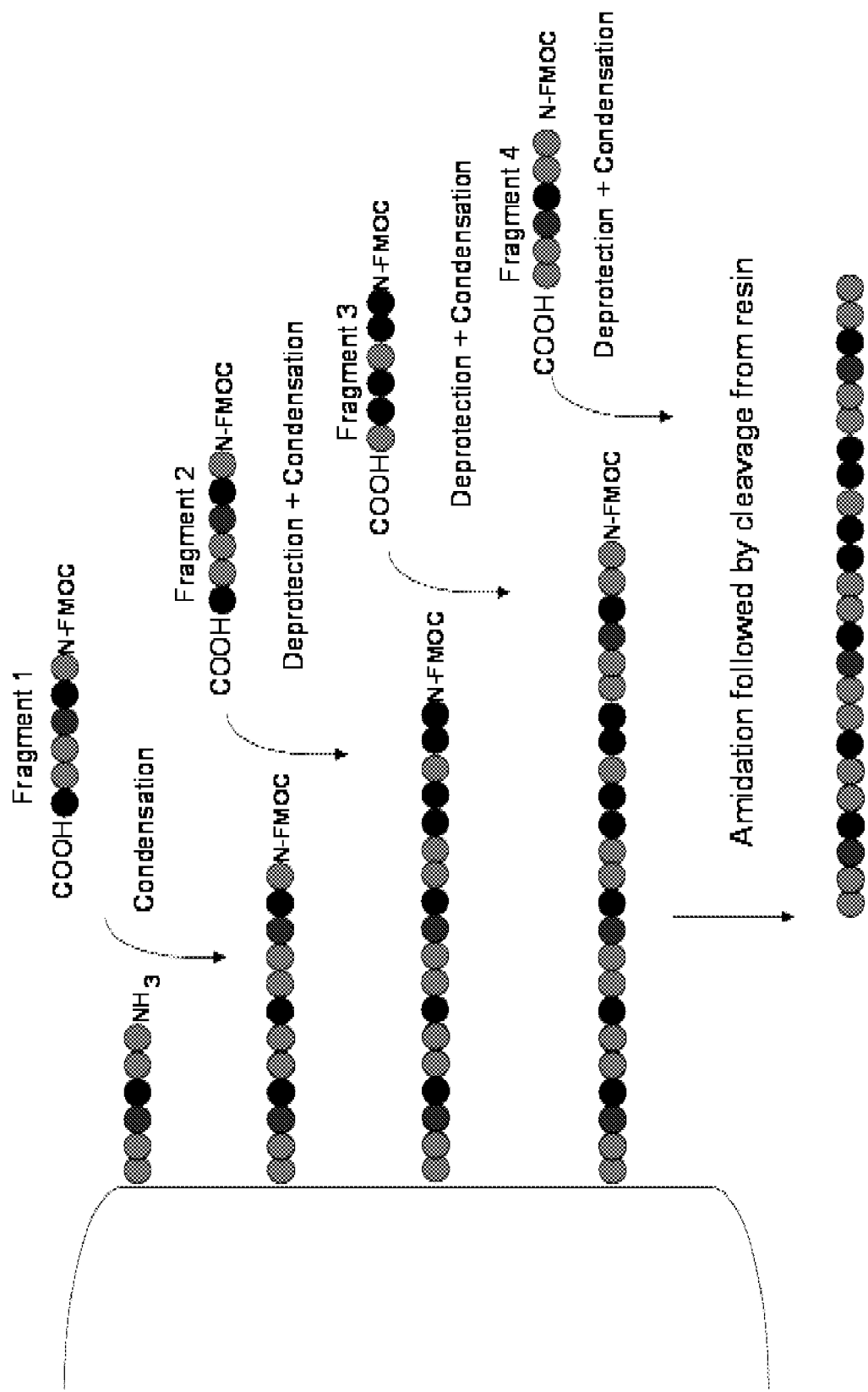
FIG. 27 is a schematic illustration of one non-limiting method of making WLBU-2 (SEQ ID NO: 10) using fragment condensation. The concept is that fragments 1-4 can be added sequentially in four steps where it would take 24 steps if the peptide was made using single-residue step-wise synthesis.

In another embodiment, fragment condensation methods are utilized to concatenate smaller peptide fragments. A number of the peptides described herein include two or more repeats of the same subunit. Solid phase synthesis methods may be utilized to produce the peptides, but that is costly as compared to the production of smaller peptides and later condensing them to form the concatenated peptides. Other chemical ligation methods may be used to concatenate the subunits. In one embodiment of a fragment condensation method, soluble peptide fragments bearing a free carboxyl group and no other competing functional groups can be attached to a deprotected free amino group of a nascent resin-bound peptide fragment using condensation chemistry. This concept is illustrated in FIG. 27 and is essentially described in Chang W C et al., Eds. *Fmoc Solid Phase Peptide Synthesis: A Practical Approach*, Oxford University Press (2000), USA. Peptides may also be prepared by standard recombinant DNA technology using techniques well known to those skilled in the art for nucleotide-based peptide design (See, e.g., Sambrook et al., Molecular Cloning: A Laboratory Manual, 2nd edition (Cold Spring Harbor Press, Cold Spring Harbor, N.Y.;

Ausubel et al., Current Protocols in Molecular Biology, John Wiley and Sons, New York, 1995). Site-directed mutagenesis or oligonucleotide synthesis, for example, may be used to prepare peptide analogs from parent peptides.

In one embodiment, the antimicrobial peptides are attached (i.e., covalently) to a membrane translocation element, such as a peptide transduction domain (PTD). PTDs have previously been shown to be able translocate various macromolecules inside a variety of cells (Mi, Z., Mai, J., Lu, X., and Robbins, P. D. Characterization of a class of cationic peptides able to facilitate efficient protein transduction in vitro and in vivo, Mol Ther. 2: 339-47, 2000; Shen, H., Mai, J. C., Qiu, L., Cao, S., Robbins, P. D., and Cheng, T. Evaluation of peptide-mediated transduction in human CD34+ cells, Hum Gene Ther. 15: 415-9, 2004; Dietz, G. P. and Bahr, M. Delivery of bioactive molecules into the cell: the Trojan horse approach, Mol Cell Neurosci. 27: 85-131, 2004; Ziegler, A., Nervi, P., Durrenberger, M., and Seelig, J. The cationic cell-penetrating peptide CPP(TAT) derived from the HIV-1 protein TAT is rapidly transported into living fibroblasts: optical, biophysical, and metabolic evidence, Biochemistry. 44: 138-48, 2005; Guelen, L., Paterson, H., Gaken, J., Meyers, M., Farzaneh, F., and Tavassoli, M. TAT-apoptin is efficiently delivered and induces apoptosis in cancer cells, Oncogene. 23: 1153-65, 2004; Ribeiro, M. M., Klein, D., Pileggi, A., Molano, R. D., Fraker, C., Ricordi, C., Inverardi, L., and Pastori, R. L. Heme oxygenase-1 fused to a TAT peptide transduces and protects pancreatic beta-cells, Biochem Biophys Res Commun. 305: 876-81, 2003; Wheeler, D. S., Dunsmore, K. E., and Wong, H. R. Intracellular delivery of HSP70 using HIV-1 Tat protein transduction domain, Biochem Biophys Res Commun. 301: 54-9, 2003; Caron, N.J., Torrente, Y., Camirand, G., Bujold, M., Chapdelaine, P., Leriche, K., Bresolin, N., and Tremblay, J. P. Intracellular delivery of a Tat-eGFP fusion protein into muscle cells, Mol Ther. 3: 310-8, 2001; and Morris, M. C., Depollier, J., Mery, J., Heitz, F., and Divita, G. A peptide carrier for the delivery of biologically active proteins into mammalian cells, Nat. Biotechnol. 19: 1173-6, 2001). It is therefore believed that attachment of a membrane translocation element, such as a PTD, to an antimicrobial peptide will enhance the activity of the antimicrobial peptide.

As used herein, a "membrane translocation element" is a compound, composition, complex or molecule that can be conjugated or otherwise attached, covalently, or otherwise, to a second compound and that, when contacted with a cell, has the ability to cause the translocation of the second compound across a cell membrane and into the cell. In one particular embodiment, the membrane translocation element is a "peptide transduction domain" or "PTD" and is, in its broadest sense, a peptide fragment that, when attached to a polypeptide, such as a protein or enzyme, facilitates internalization of the polypeptide by a mammalian cell. The mechanism by which membrane translocation is thought to occur is, without any intent to be bound by this theory, a temperature-independent, non-endocytotic mechanism that is thought to involve membrane destabilization. Well-known PTDs include HIV tat and *Drosophila* antennapedia PTDs. Synthetic tat PTD analogs have been developed (Ho et al., (2001) Cancer Research 61:474-477; Mai, et al. (2002), Efficiency of Protein Transduction is Cell Type-dependent and is enhanced by Dextran Sulfate, J. Biol. Chem. 277(33):30208-218; and Shen, H., et al. Hum. Gene Ther. 15:415-419). Poly-arginine tracts, for example and without limitation 4-12 Arg residues, poly-lysine tracts, for example and without limitation 2-12 Lysine residues, and 5-11 residue "polyRQ" tracts (RR (QRR)1-3), as described in Mai, et al. (2002) J. Biol. Chem. 277(33):30208-218, also have been shown to be useful as PTDs. An arginine- and lysine-rich tract, specifically, a tract comprising a majority of both arginine and lysine also can serve as a PTD. A non-limiting example of a useful PTD is: RRQRRTSKLMKR (SEQ ID NO: 17). Thus, an example of a PTD-Antimicrobial conjugate is RRQRRTSKLMKR-X (SEQ ID NO: 17), where X is an antimicrobial peptide as described herein, including: SA-5 (SEQ ID NO: 1); LSA-5 (SEQ ID NO: 2); WLSA-5 (SEQ ID NO: 3); LBU-1 (SEQ ID NO: 4); LBU-2 (SEQ ID NO: 5); LBU-3 (SEQ ID NO: 6); LBU-3.5 (SEQ ID NO: 7); LBU-4 (SEQ ID NO: 8); WLBU-1 (SEQ ID NO: 9); WLBU-2 (SEQ ID NO: 10); WLBU-3 (SEQ ID NO: 11); WLBU-4, (SEQ ID NO: 12); WR6 (SEQ ID NO: 13); WR12 (SEQ ID NO: 14); WR18 (SEQ ID NO: 15); and WR24 (SEQ ID NO: 16). As such, assuming X is attached to the PTD by a peptide bond, a peptide comprising the PTD described above and WLBU-2 would have the amino acid sequence: RRQRRTSKLMKR-RRWVR RVRRV WRVV RVVRR WVRR (SEQ ID NO: 18), in which the dash indicates the peptide bond junction between the PTD and WLBU-2.

In one non-limiting embodiment, an antimicrobial peptide, such as any antimicrobial polypeptide described herein, is complexed with a PTD by covalent attachment. A typical covalent attachment between the PTD and antimicrobial peptides would be, without limitation, a common peptide bond, though other covalent attachment methods certainly would be suitable, so long as the PTD has the desired effect of facilitating cell membrane translocation of the antimicrobial peptide, and therefore loading of the targeting cell. In one embodiment, the PTD is attached to the antimicrobial peptide by a di-glycine spacer (Mai, et al. (2002) J. Biol. Chem. 277(33):30208-218). Other cross-linking methods may be used to attach the PTD and antimicrobial peptide. A large number of protein conjugation chemistries also are available commercially (see generally, Cross-Linking reagents, Technical Handbook, 2005, Pierce Biotechnology, Inc.). Many bi-functional or poly-functional reagents, both homo- and hetero-functional (such as those described in the catalog of the Pierce Chemical Co., Rockford, Ill.), may be employed as a linker group. Coupling may be affected, for example, through amino groups, carboxyl groups, sulfhydryl groups or oxidized carbohydrate residues.

The PTD-antimicrobial peptide complex may be prepared by widely-known polypeptide synthesis processes or by a suitable recombinant genetic construct for recombinant production of the PTD-antimicrobial peptide complex, which may be prepared and delivered to a host cell for production of the desired protein. Suitable host cells for recombinant production of the desired protein include bacterial, yeast, insect and mammalian cells as are broadly known. Recombinant protein may be produced in batch culture, or in continuous culture in a bioreactor.

In one embodiment, a nucleic acid containing an open reading frame (ORF) encoding an antimicrobial peptide is attached, in-frame, with a nucleic acid containing a sequence encoding a PTD to produce an ORF encoding a functional PTD-antimicrobial peptide. Methods for attaching (ligating) a PTD-encoding nucleic acid to an antimicrobial peptide-encoding nucleic acid are known in the art, if not a matter of simple design choice of a person of skill in the field of molecular biology. Vectors containing expression cassettes are broadly available for expression of genes in various host cells, such as *E. coli, S. cerevisiae*, insect and mammalian cells, such as Chinese Hamster Ovary (CHO) cells.

By "expression" it is meant the overall flow of information from a gene (without limitation, a functional genetic unit for producing a gene product, typically encoded on DNA or RNA, for some viruses, and comprising a transcriptional promoter, and other cis-acting elements, such as response elements and/or enhancers, an expressed sequence that typically encodes a protein (open-reading frame or ORF) or functional/structural RNA, and a polyadenylation sequence), to produce a gene product (typically a protein, optionally post-translationally modified or a functional/structural RNA). By "expression of genes under transcriptional control of," or alternately "subject to control by," a designated sequence, it is meant gene expression from a gene containing the designated sequence operably linked (functionally attached, typically in cis) to the gene. The designated sequence may be all or part of the transcriptional elements (without limitation, promoters, enhancers and response elements), and may wholly or partially regulate and/or affect transcription of a gene. A "gene for expression of" a stated gene product is a gene capable of expressing that stated gene product when placed in a suitable environment—that is, for example, when transformed, transfected of transduced into a cell, and subjected to suitable conditions for expression. In the case of a constitutive promoter "suitable conditions" means that the gene typically need only be introduced into a host cell. In the case of an inducible promoter, "suitable conditions" means when an amount of the respective inducer is administered to the expression system (e.g., cell) effective to cause expression of the gene.

As indicated above, an antimicrobial peptide-PTD polypeptide may be prepared by standard protein synthesis chemistries. The antimicrobial peptide-PTD polypeptide also may be prepared by fragment condensation in which a PTD protein and one or more lytic base units are attached by condensation. In this manner a variety of different antimicrobial peptide-PTD polypeptides may be easily manufactured from basic building blocks. Likewise, the cost and time required for base-by-base polypeptide synthesis is avoided by concatenation of pre-manufactured subunits.

The amino acid sequences of the peptides can be confirmed and identified by amino acid composition analysis as well as manual and automated Edman degradation and determination of each amino acid, HPLC analysis, or mass spectrometry. The N-terminal amino acid of the peptides may contain a free amino group or be acetylated, and the C-terminal amino acid of the peptide may be amidated, lipidated or comprise a free carboxyl group. Other modifications of the peptide termini known to those skilled in the art are within the scope of the invention.

The criticality of particular amino acid residues in a peptide may be tested by altering or replacing the residue of interest. For example, the requirement for a Cys residue, which can be involved in the formation of intramolecular or intermolecular disulfide bonds, can be tested by mutagenesis of the Cys to another amino acid, for example, tyrosine, which cannot form such a bond. A Cys can be chemically altered so as to prevent the formation of a disulfide bond by, for example, reduction and carboxyamidation, in which an amide group is added to the sulfur atom of the cysteine (Creighton, T. E., ed., Protein Structure: A Practical Approach, IRL Press, Oxford, 1989). Conversely, a Cys residue in a peptide may be maintained in an oxidized state (that is, in the form of a disulfide bond) in order to assess whether such bonds are involved in the antimicrobial activity of a peptide. Such oxidation may be performed by, for example, an air-oxidation procedure (Ellman, G. L., *Arch. Biochem.* 82: 70-77, 1959), or by DMSO oxidation (Tam et al., J. Am. Chem. Soc. 113: 6657-6662, 1991). Similarly, Trp residues can be substituted on the hydrophobic face (e.g. the WLSA-5 peptide (SEQ ID NO: 3)).

Computer modeling is useful to design the antimicrobial peptides described herein based on their preferred structural properties. A standard method known in the art for prediction of amphipathic helical structure from a linear sequence is the Eisenberg algorithm (Eisenberg et al., Biopolymers 27: 171-177, 1990) and is useful for modeling the antimicrobial peptides described herein. Peptide sequences are analyzed for predicted secondary structure, hydrophobic moment, and amphipathicity using programs available to the skilled artisan (e.g. may be obtained from the internet). These programs which generally use algorithms that are predictive for secondary structure (Chou et al., *Adv. Enz.* 47: 45-146, 1978; Gamier et al., *J. Mol. Biol.* 120: 97, 1978) or hydrophobic moment (Eisenberg et al., *Proc. Natl. Acad. Sci. U.S.A.* 81:140-144, 1984) may be used.

Peptide concentration may be quantified using a standard ninhydrin colorimetric assay (see Example 1 below). A standard curve using a Leu standard is generated by reading the spectrophotometric absorbence at 570 nm of increasing volumes of the leucine stock combined with the commercially available (Dupont) ninhydrin reagents on a spectrophotometer. The readings of peptide samples are compared to the leucine standard curve to quantitate the amount of peptide in each sample. Alternatively, if the peptide contains Trp in its sequence, peptide concentration can be determined by UV spectroscopy using a molar extinction coefficient at 280 nm=5500 $Lmol^{-1}cm^{-1}$).

The effect of the antimicrobial peptides described herein on the viability of prokaryotic and eukaryotic cells may be assayed by any method that determines survival after treatment or exposure to the peptides. For screening purposes, standard bacterial broth dilution assays are used and can be compared with red blood cell lysis assays (see Tencza et al., 1999, *Journal of Antimicrobial Chemotherapy* 44:33-41). However, ultimately this selective toxicity comparison should be performed when both prokaryotic and eukaryotic cells are exposed to peptide under identical conditions. In addition, the effect of the antimicrobial peptides on the viability of other pathogens, including yeast, mycoplasma and viruses, may also be tested.

The antibacterial properties of the antimicrobial peptides described herein may be determined, e.g., from a bacterial lysis assay (Example 1), as well as by other methods, including, inter alia, growth inhibition assays (Blondelie et al., *Biochemistry* 31:12688, 1992), fluorescence-based bacterial viability assays (e.g., Molecular Probes BacLight), flow cytometry analyses (Arroyo et al., *J. Virol.* 69: 4095-4102, 1995), and other standard assays known to those skilled in the art.

Determination of the antifungal properties of the antimicrobial peptides described herein may be performed by techniques well known to those skilled in the art (Selitrennikoff, C., Screening for Antifungal Drugs, in Biotechnology of Filamentous Fungi, Finkelstein et al., eds., Butterworth-Heinemann, Boston, 1992, see also Example 10, below. Determination of the antiviral properties of the antimicrobial peptides described herein may be performed by techniques well known to those skilled in the art, for example by the ability of a peptide to inhibit viral plaque formation in standard, art recognized, in vitro assays (e.g., Wild et al., *Proc. Natl. Acad. Sci. USA* 89: 10537-10541, 1992, see also Examples 5 and 8 below).

The assays for growth inhibition of a microbial target can be used to derive a minimum bactericidal concentration (MBC) value for the peptide, i.e., the concentration of peptide required to kill 99.9% (3-log decrease) of the microbial sample being tested. This value is well known to those in the art as representative of the effectiveness of a particular antimicrobial agent (e.g., an antibiotic) against a particular organism or group of organisms. In assays to detect the MBC of a peptide, growth inhibition of a bacterial population also can be measured with reference to the number of colony forming units (cfu) after exposure to a peptide relative to a control experiment without a peptide.

Another parameter useful in identifying and measuring the effectiveness of the antimicrobial peptides described herein is the determination of the kinetics of the antimicrobial activity of a peptide. Such a determination can be made by performing any of the assays described herein and determining antimicrobial activity as a function of time. In a preferred embodiment, the peptides display kinetics that result in efficient killing of a microorganism.

The antimicrobial peptides described herein display selective toxicity to target microorganisms and minimal toxicity to mammalian cells. Determining the toxicity of the peptides described herein on mammalian cells may be performed using tissue culture assays. For mammalian cells, such assay methods include, inter alia, trypan blue exclusion or MTT assays (see Moore et al., 1994, *Peptide Research* 7:265-269). Where a specific cell type may release a specific metabolite upon changes in membrane permeability, that specific metabolite may be assayed, e.g., the release of hemoglobin upon the lysis of red blood cells (see Srinivas et al., 1992, *Journal of Biological Chemistry* 267:7121-7127). In addition, the disruption of the trans epithelial resistance (Rte) of a cell monolayer that have formed tight junctions can be monitored (see FIG. 9). The antimicrobial peptides described herein are preferably tested against primary cells, e.g., using human bronchial epithelial (HBE) cells in polarized culture, or other primary cell cultures routinely used by those skilled in the art. Permanently transformed cell lines may also be used, e.g., Jurkat cells may also be used to demonstrate this proof of concept.

In determining the therapeutic potential of an antimicrobial peptide, a lower MBC for bacterial, fungal, protozoal, or viral samples relative to that observed for mammalian cells defines the therapeutic window and reflects the selective antimicrobial toxicity of the agent. Characterization of the antimicrobial activity of the antimicrobial peptides described herein can be performed using any microorganism that can be cultured and assayed, as above, including bacteria, fungi, protozoa or viruses.

Antibacterial assays for the antimicrobial peptides described herein can be performed to determine the bacterial killing activity toward both gram-positive and gram-negative microorganisms. *E. coli* and *P. aeruginosa* are examples of gram-negative organisms. *S. aureus* may be used as a model of a gram-positive microorganism, and this is a significant clinical target since most strains are refractive to most systemic antibiotic treatments. Methicillin-resistant *S. aureus* may be used as an antibiotic-resistant model organism. *E. faecalis* can be assayed, and in particular, the vancomycin-resistant isolates found in clinical settings, e.g. hospitals. *S. marcescens* is a source of ophthalmic and other topical infections, and can be readily assayed. The peptides may be used in the treatment of external ear infections (otitis externa), or in the treatment of sexually transmitted diseases such as those caused by *Neisseria gonorrhoeae*. Other bacterial pathogens, often found extracellularly on mucosal surfaces, which may be targets for the antimicrobial peptides described herein include, but are not limited to, *Streptococcus pneumonia*, *Streptococcus pyogenes*, Group B Streptococci, *Gardnerella vaginalis*, *Klebsiella pneumoniae*, *Acinetobacter* spp., *Haemophilus aegyptius*, *Haemophilus influenzae*, *S. epidermis*, *Propionibacterium acnes*, and oral pathogens such as *Actinomyces* spp., *Porphyromonas* spp., and *Prevotella melaminogenicus*. Other microbial pathogens may also be targets for these peptides and these microbial pathogens, and the infections that they cause, are known to those skilled in the art.

*Mycoplasma* spp. belong to the class Mollicutes, eubacteria that appear to have evolved regressibly by genome reduction from gram-positive ancestors. Unlike classic bacteria, they have no cell wall but instead are bounded by a membrane, and may be susceptible to certain antimicrobial peptides described herein. Antimycoplasma assays may be performed to test the antimycoplasma activity of the antimicrobial peptides described herein. *Mycoplasma* human pathogens include *Mycoplasma pneumoniae* (a respiratory pathogen), *Mycoplasma hominis* (a urogenital pathogen) and *Ureaplasma urealyticum* (a urogenital pathogen). The antimicrobial peptides described herein may be used to treat diseases related to mycoplasma infection. In addition, mycoplasma contamination is a frequent problem in culturing cells in vitro and is very difficult to effectively eliminate. Therefore, the antimicrobial peptides described herein may be useful in selectively eliminating mycoplasma contamination in tissue culture.

Certain fungi also are susceptible to the antimicrobial peptides described herein, including members of the medically important *Candida* and *Cryptococcus* genera. The membranes of fungi contain ergosterol, which is not found in human cells. This differentiation may be exploited in therapeutic applications so as to design antimicrobial peptides, which selectively inhibit fungi, yet do not interfere with human or mammalian membrane function. Precedent for a mechanism of selective antifungal membrane targeting is found, for example, in the use of the antifungal agent, amphotericin B, which binds ergosterol and forms pores in the membrane (Goodman et al., The Pharmacological Basis of Therapeutics, Macmillan Publishing, New York, 1985). All fungi can be considered as potential targets of these peptides, including, but not limited to, dermatophytes, yeasts, dimorphic fungi, and filamentous molds. Specific fungal pathogens which may be targets for the antimicrobial peptides described herein, but are not limited to, *Microsporum*, *Epidermophyton*, *Candida*, *Cryptococcus*, and *Trichophyton* genera, *Sporothrix schenkii* and *Aspergillus fumigatus*, as well as other fungal pathogens known to those skilled in the art.

Both DNA and RNA viruses are potential targets of the antimicrobial peptides described herein. In a particular embodiment, an enveloped virus may be susceptible to the antiviral effect of the peptides due to their ability to target and disrupt membrane structures. While all viruses are potential targets, the enveloped viruses, such as poxvirus, herpesvirus, rhabdovirus, hepadnavirus, baculovirus, orthomyxovirus, paramyxovirus, retrovirus, togavirus, bunyavirus and flavivirus, for example and without limitation, may be particularly susceptible to the antimicrobial peptides described herein. In one embodiment, the virus is a lentivirus, such as HIV-1; a herpes virus, such as HSV; or an orthomyxovirus, such as an influenza virus. In one embodiment, the virus is HIV-1. The spread of this virus on a mucosal surface might be manipulated by the topical administration of an antimicrobial peptide described herein, such as a synthetic peptide that is active against HIV-1 and other sexually transmitted disease pathogens. See Example 5 below. In another embodiment, the virus is an orthomyxovirus, for example an influenza virus, which is shown in Example 8, below, as being neutralized by an antimicrobial peptide as described herein in both a hemagglutination assay and by infectivity in mice.

Further, elucidation of the mechanism of the peptides and their biochemical targets may come from the use of isogenic mutants of bacteria, fungi, mycoplasma and viruses that are altered in cytoplasmic and/or outer wall membrane content. Antimicrobial peptides may be specifically tested against these mutants to identify specific designs that are optimally inhibitory against particular membrane constituents.

The peptides described herein may be useful for inhibiting or treating a particular microbial infection, such as, but not limited to, cystic fibrosis lung infection (see Example 3 below), joint sepsis (see Example 4 below), ocular infections, periodontal disease, STDs, otitis extema, cutaneous infections, burn infections, vaginal infections, Candidiasis, and diabetic foot ulcers.

Furthermore, the antimicrobial peptides described herein may be useful to inhibit microbial colonization. For example, the peptides may be delivered prophylactically or and expressed by eukaryotic cells in vivo, via transfection using viral vectors. The continued expression of the peptides in the cells and secretion into their environment may interfere with colonization of microbes and prevent microbial infection. This may be particularly useful to prevent infections associated with cystic fibrosis by delivering the antimicrobial peptides to airway epithelial cells. The peptides may inhibit colonization of bacteria involved in cystic fibrosis. Cells expressing the peptides may be able to continuously combat the colonization of a range of pathogenic microbes.

In the treatment of cystic fibrosis or other airway diseases (e.g., infectious diseases or conditions), an antimicrobial peptide described herein may be administered by aerosol in an amount and in a dosage regimen effective to prevent and/or treat a microbial infection, such as an infection by a bacterial, fungal or viral agent. In one embodiment, the dosage form comprises one or more antimicrobial peptides as described herein in hypotonic saline, which is commonly used to loosen sputum in cystic fibrosis patients. In the treatment of cystic fibrosis, a combination dosage form comprising the peptides along with another therapeutic agent for the treatment of cystic fibrosis also may be utilized. Other active agents that may be combined with the peptide include, without limitation, deoxyribonuclease (DNAse, such as dornase alfa (e.g., Pulmozyme), a human DNAse), N-acetylcysteine, albuterol and ipratropium bromide. The peptides or combination dosage forms typically can be packaged as a dosage form in any useful aerosolizing/nebulizing device as are available. The peptides or combination dosage forms may be liquid or powdered solid, for instance, lyophilized. A large number of suitable aerosolization devices are known in the pharmaceutical arts and are appropriate for airway delivery of the antimicrobial peptides alone or in combination with one or more additional active agents.

The evaluation of an antimicrobial peptide for inhibiting or treating a particular microbial infection may also involve the use of animal models of infection that are acknowledged by those skilled in the art to be relevant to such infections in a human or other mammal. Example 3 below describes a cell culture model of cystic fibrosis lung infection in which the selective toxicity of peptides may be tested. Example 4 below describes an animal model of joint sepsis that can be used to evaluate antimicrobial peptides.

Advantages of the use of the antimicrobial peptides described herein as antibiotics include the likelihood that it may be more difficult for a microorganism to develop a mechanism of resistance against an antibiotic that targets a membrane structure. The fact that other microbial pathogens have never been exposed to these agents (in contrast to conventional antibiotics) is an additional advantage. In view of the above noted properties of the antimicrobial peptides described herein, it is contemplated that they may be used in treating an infectious process in a host caused by a microorganism.

Systemic administration of the antimicrobial peptides described herein may induce an immunogenic response in a host. Therefore, techniques known in the art, such as waxing with polyethylene glycol, may be employed to reduce the immunogenicity of the peptides when administered systemically.

In the context of delivery of the peptides described herein to prevent or treat an infection, an "effective amount" of a given therapeutic agent, compound, etc., is an amount effective to achieve a desired prophylactic or therapeutic goal in a patient. In the context of a prevention or treatment of an infection by an infectious agent, such as a bacterial, fungal or viral agent, this means that either infection is prevented and/or ameliorated by the agent as compared to a negative control (without the peptide). The status of any disease or condition may be monitored by any suitable method known to those in the medical arts, including, without limitation, those methods described herein.

Also provided herein are surfaces to which one or more antimicrobial peptides described herein are attached. The surface may be any surface (e.g., substrate) to which a peptide can be attached, including: plastics (polymeric compositions); ceramics or other inorganic composites, including artificial bone or dental substitutes; metals; glass; fabrics and threads (e.g., wovens, non wovens, threads, sutures, etc.), or combinations of materials, such as polymer-coated metals. By surface, it is meant any site on the material to which a peptide can be attached, including outer surfaces, such as visible surfaces, and inner surfaces, such as the interior surfaces of pores, interstices or matrices. The peptide can be attached directly to the surface or through a linking group that can be any useful group. The peptides comprise an N-terminal amine as well as a C-terminal carboxyl group. Both of these groups are considered to be "active groups" in that they can be used to link to another compound, such as a polymer or linker. Other non-limiting examples of active groups include OH, SH, CN, epoxide, as well as a myriad of other groups that can be used to link chemical compounds. As indicated above, the peptides may be linked directly to the substrate if the substrate has amine- or carboxyl-reactive groups, such as amidoesters and N-hydroxysuccinimide esters for the amine group and carbodiimides for the carboxyl group. More typically, the peptide is linked to a surface by a linker. A large number of linkers are commercially available (see e.g., CROSSLINKING REAGENTS: Technical Handbook, # 1601361 (March 2006), Pierce Biotechnology, Inc. (Thermo Scientific)). Polymeric compounds, including copolymers, may be used as linkers, for example, by polymerizing monomers on a surface by any useful chemistry, including condensation, radical polymerization, etc.

Surfaces may be derivatized with the peptide by any useful method. The following are merely exemplary. Glass can be linked to a peptide by first coating the glass with an siloxane (e.g., siloxane (silicone, comprising an active group pendant from the $(Si-O)_n$ siloxane backbone, including, without limitation organosiloxanes, carboxysiloxanes, carboxyglycolestersiloxanes, and aminosiloxanes) and subsequently attaching the peptide(s) via a suitable linker. Alternately, glass having a halide group, such as resulting from treatment with or incorporation of a silicon halide, such as silicon bromide, can be derivatized by a radical polymerization method, such as atom transfer radical polymerization (ATRP), to provide a linker and active groups to which the peptide can be attached. Metals may be coated with a suitable coating composition, for instance one or more (co)polymers, that comprises active groups to which a peptide or linker can be attached. Ceramics and other inorganic compounds can be derivatized with a peptide, for example, by the immersion method described in the example below, or by coating the material with a composition that provides active groups.

Any polypeptide (peptide) described herein which exhibits antimicrobial activity (see, for example, those listed in Example 4, Table 3) is expected to retain its antimicrobial activity on conjugation with a surface (e.g., solid phase substrate). Therefore, the antimicrobial peptides described herein are useful as coatings on: implanted devices, such as prostheses, e.g. prosthetic joints and limbs. The peptides may also be useful as coatings on artificial organs and matrices therefor, as well as intraocular lenses.

The antimicrobial peptides described herein may have a single amino group and a free sulfhydryl group. These functional groups allow for specific attachment to a derivatized surface. For example, N-hydroxysuccinimide (NHS) chemistry can be used to attach an appropriately derivatized surface to the N-terminal amino group of the peptide. Alternatively, a surface derivatized with free carboxyl groups could be cross-linked to the free sulfhydryl group on the peptide Cys residue using m-maleimidobenzyl-N-hydroxy-succinimide ester (MBS, Pierce Chemical, Rockford, Ill.). Other methods to couple peptides to derivatized surfaces are known to those skilled in the art.

The antimicrobial peptides also may be absorbed or adsorbed onto or into a material. For example, a hydrogel, such as an intraocular implant may comprise one or more antimicrobial peptide described herein in order to prevent infection. The antimicrobial peptides may be absorbed into or onto a bandage, and optionally dried or lyophilized. Tissue engineering matrices, such as natural matrices prepared from collagen and/or other extracellular matrix component may be treated with the antimicrobial peptides prior to implantation or seeding with cells. Other examples of items that would benefit from having an antimicrobial surface or content are or would be recognized by one of skill in the art, including without limitation: bandages; sutures; staples; medical devices to come in contact with a subject or a cell, tissue, bodily fluid, biopsy or organ of a subject; items for handling and treatment of bodily fluids ex vivo or in vitro, such as blood, serum or plasma containers, filters, flasks, tubing, bottles, tubes, tissue culture dishes and plates, centrifuge tubes, pipettes and disposable tips thereof, chromatography columns and chromatography media, such as agarose or polymeric beads etc. and as described elsewhere in this disclosure; clothing articles and safety articles, such as protective suits, uniforms, gloves, goggles and protective items such as breathing masks; and disposable or non-disposable eating utensils, including nipples or other valves for use in baby bottles or sip-cups and food service items (e.g., silverware, glassware dishes, bowls, etc.), which would be especially useful for serving immunocompromised subjects.

In addition, a peptide-cargo complex is provided herein, wherein the peptides described herein may be attached to a cargo to allow for the delivery of the cargo into a target microorganism. The cargo may comprise a factor having anti-microbial activity and may improve the potency and/or increase the antimicrobial activity of the antimicrobial peptides described herein. For example, the antimicrobial peptides described herein may be cross-linked to antibacterial enzymes such as lysozyme or antibiotics, such as penicillin, to increase their potency. Other methods for attaching the antimicrobial peptides described herein to cargo are well known in the art.

Methods are provided for eliminating an infectious process by administering the antimicrobial peptides described herein to a patient for a time and under conditions to promote healing. In a particular aspect, the high potency and rapid bactericidal activity of these peptides make them attractive candidates for use in preventive therapies, such as sterilization of wounds prior to suture, as well as the sterilization of instruments prior to their use in surgical or other invasive procedures. Their microbial specificity renders the antimicrobial peptides described herein particularly useful in inhibiting unwanted microbial growth in tissue culture, especially those used for production of recombinant proteins or vectors for use in gene therapy. In another embodiment, the peptides may be used in combination formulations with one or more other drugs to facilitate delivery of a drug into a host cell or microorganism (e.g., see Example 4, FIG. 12).

Physiologic compositions are provided containing one or more of the antimicrobial peptides as the active ingredient which may be administered to a host in a therapeutically effective amount, an amount of the peptide (or combinations of peptides) sufficient to minimize or eliminate the target microorganism from a cell culture, or host individual.

The physiological compositions contain a therapeutically effective dosage of at least one of the antimicrobial peptides described herein, together with a pharmaceutically acceptable carrier. Methods also are provided for treating a microbial infection in a host using the antimicrobial peptides and compositions described herein. Such treatment comprises the administration of a physiological composition in a therapeutically effective amount to an individual in need of such treatment. The compositions may be administered parenterally by intramuscular or intravenous routes but also would be useful when administered by aerosolization, subcutaneous, oral, topical and intranasal administration. Preferably, physiologic compositions containing the peptides described herein are applied topically for the elimination of surface infections caused by microorganisms. When used in a topical pharmaceutical composition, the peptide active ingredient can be used at a concentration of 0.001 to 20% (w/v) of the composition.

When applied topically, the peptide compositions may be combined with other ingredients, such as carriers and/or adjuvants. The peptides may also be covalently attached to a protein carrier, such as albumin, or to a prosthetic implant so as to minimize diffusion of the peptides. There are no limitations on the nature of such other ingredients, except that they must be pharmaceutically acceptable, efficacious for the intended administration and cannot degrade the active ingredients of the compositions. When a composition comprising an antimicrobial peptide described herein is applied to a site of topical infection, it may act as an irritant (which would stimulate influx of scavenger cells). The peptide compositions can also be in the form of ointments or suspensions, preferably in combination with purified collagen. The peptide compositions also may be impregnated into transdermal patches, plasters and bandages, preferably in a liquid or semi-liquid form.

The antimicrobial peptides described herein may also be systematically administered for promoting the healing of an infectious process. When applied systemically, the peptide compositions may be formulated as liquids, pills, tablets, lozenges or the like, for enteral administration, or in liquid form for parenteral injection. The peptides (or peptide-protein conjugates) may be combined with other ingredients such as carriers and/or adjuvants known to those skilled in the art. There are no limitations on the nature of such other ingredients, except that they must be physiologically acceptable, efficacious for their intended administration and cannot degrade the active ingredients of the compositions. The physiologic forms suitable for injection include sterile aqueous solutions or dispersions and sterile powders for the extemporaneous preparation of sterile injectable solutions or dispersions. In all cases the ultimate solution form must be sterile and fluid. Typical carriers known in the art include a solvent or dispersion medium containing, for example, water buffered aqueous solutions (i.e., biocompatible buffers), ethanol, polyol such as glycerol, propylene glycol, polyethylene glycol, suitable mixtures thereof, surfactants or vegetable oils. Sterilization can be accomplished by an art-recognized technique, including but not limited to, filtration or addition of antibacterial or antifungal agents, for example, paraben, chlorobutanol, phenol, sorbic acid or thimerosal. Further, isotonic agents such as sugars, for example, may be incorporated in the subject compositions. Production of sterile injectable solutions containing the subject peptides is accomplished by incorporating these compounds in the required amount in the appropriate solvent with various ingredients enumerated above, as required, followed by sterilization, preferably filter sterilization.

When the antimicrobial peptides described herein are administered orally, the physiologic compositions thereof containing an effective dosage of the peptide may also contain an inert diluent, an assimilable, edible carrier and the like, be in hard or soft shell gelatin capsules, be compressed into tablets, or may be in an elixir, suspension, syrup, or the like. The subject peptides are thus compounded for convenient and effective administration in pharmaceutically effective amounts with a suitable pharmaceutically acceptable carrier in a therapeutically effective dosage.

The precise effective amount of peptides to be used in the methods described herein to control infection can be determined without undue experimentation by those skilled in the art who understand the nature of the activity of antibiotics and the nature of an infectious process. The amount of an antibiotic peptide (such as the antimicrobial peptides described herein) that must be utilized can vary with the magnitude of the infection and the microorganism to be treated. The amount of an antimicrobial peptide described herein per unit volume of combined medication for administration may also be determined without undue experimentation by those skilled in the art. However, it can generally be stated that the peptides should preferably be present in an amount of at least about 1.0 nanogram per milliliter of combined composition, more preferably in an amount up to about 1.0 milligram per milliliter. Systemic dosages also depend on the age, weight and conditions of the patient and on the administration route. For example, a suitable dosage for the administration to adult humans can range from about 0.01 to about 100 mg per kilogram body weight. The preferred dosage can range from about 0.5 to about 5.0 mg per kilogram body weight. As used herein, a physiologically acceptable carrier includes any and all solvents, dispersion media, coatings, and the like. The use of such media and agents are well known in the art.

Because the antimicrobial peptide compositions described herein are designed to eliminate an ongoing infectious process, a continual application or periodic reapplication of the compositions may be indicated and preferred. Unless otherwise indicated, conventional techniques of synthetic organic chemistry, protein chemistry, molecular biology, microbiology, recombinant DNA technology, and pharmacology, which are within the skill of the art, may be used in practicing any embodiment of the methods, compositions and compounds described herein. Such techniques are explained fully in the literature (See, e.g., Scopes, R. K. Protein Purification: Principles and Practices, 2nd edition, Springer-Verlag, 1987; Methods in Enzymology, S. Colwick and N. Kaplan, editors, Academic Press; Sambrook et al., Molecular Cloning: A Laboratory Manual, 2nd edition, Cold Spring Harbor Press, Cold Spring Harbor, N.Y.; Ausubel et al., Current Protocols in Molecular Biology, John Wiley and Sons, New York, 1995; Remington's Pharmaceutical Sciences, 17th ed., Mack Publishing Co., Easton, Pa., 1985).

The following examples further illustrate the invention, but are not meant to limit the same.

EXAMPLES

Example 1

Design and Synthesis of eLLPS

Design of eLLPs. Using the principles described above, peptide sequences were designed for synthesis based on altering the residues of the LLP1 parent sequence to create an Arg-rich hydrophilic face and a more idealized hydrophobic face of a predicted amphipathic α-helical structure. In one case, WLSA-5 (SEQ ID NO: 3), Trp residues were included to increase potency and spectrum of activity (FIG. 1). For LBU-2 (SEQ ID NO: 5) and LBU-3 (SEQ ID NO: 6), an idealized amphipathic α-helical structure consisting of Arg residues and Val residues on the hydrophilic and hydrophobic faces, respectively, were designed and are described in FIG. 2.

Peptide Synthesis. Peptides were synthesized as described previously (see Miller, Jaynes and Montelaro, *AIDS Research & Human Retroviruses* 7:511-519 and Fontenot et al., *Peptide Research* 4:19-25) using either an Advanced Chemtech model 200 (Advanced Chemtech, Louisville, Ky.) or a Millipore 9050+ (Millipore, Bedford, Mass.) automated peptide synthesizer with Fmoc synthesis protocols. After cleavage and deprotection, synthetic peptides were characterized and purified by reverse-phase HPLC on Vydac C18 or C4 columns (The Separations Group, Hesperia, Calif.). The identity of each peptide was confirmed by mass spectrometry (University of Pittsburgh Protein & Peptide Core Facility).

Peptide Quantitation. Peptide concentrations were determined by quantitative ninhydrin assay. Briefly, to samples containing 5-60 nmol peptide, Ninhydrin Reagents A, B, and C prepared as described by Sarin et al., (*Analytical Biochemistry* 117:147-157) were added. A leucine standard solution, calibrated by routine amino acid composition analysis, consisting of 0-60 nmol leucine were prepared in parallel generate a standard curve. The purple color formed upon incubation at 100° C. for 10 m was quantitated by dilution in 1:1 isopropanol/water, transferred to triplicate wells of a 96-well plate, and measurement of the $Abs_{570}$ on a microwell plate reader (Dynatech, Chantilly, Va.). The concentration of peptide was determined by a comparison to the standard curve and corrected for by the number of free amino groups that were associated with each peptide.

Example 2

Evaluation of Peptides Using In Vitro Bacterial Lysis Assays

Test Samples. The peptides used for this study are described and prepared as indicated above. The panel of bacterial isolates used for these experiments included both gram-positive and gram-negative clinical isolates. A given bacterial isolate was prepared as described below and exposed to a given antimicrobial peptide as described below.

Bacterial lysis assay. Bacterial lysis assays were conducted in a manner similar to that described previously (Lehrer, R. I., M. E. Selsted, D. Szklarek, and F. J. 1983. Infect. Immun. 42: 10-4, 1983; Miller, M. A., R. F. Garry, J. M. Jaynes, and R. C. Montelaro, AIDS Res Hum Retroviruses 7:511-519, 1991). Bacterial suspensions were cultured in Luria-Bertani Broth to mid-log growth phase and washed by two cycles of centrifugation and suspension in 10 mM phosphate buffer. The $Abs_{600}$ of the suspension was adjusted with 10 mM phosphate buffer such that, upon dilution, $5$-$10 \times 10^5$ cfu/mL would be treated in the assay. Bacteria were incubated for 1 h with two-fold dilutions of peptides (100 µM to 100 nM) in 96-well plates using 10 mM phosphate buffer, pH 7.2, as a diluent. Ten-fold dilutions of bacteria were performed to 1:1 000; a 100 µl aliquot from each condition was spread on the surface of tryptic soy agar plates (Difco, Detroit, Mich.) which were incubated overnight. Colonies of surviving bacteria (cfu, colony-forming units) were counted and compared to untreated controls to determine the amount of peptide-induced killing under each condition. Log killing is defined as the log of the ratio of cfu present before and after treatment with peptide. The minimal bactericidal concentration, MBC, is the peptide concentration at which 99.9% (three log) killing is achieved (Pearson et al., Antimicrob. Agents Chemother. 18: 699-708, 1980).

Figure 3:
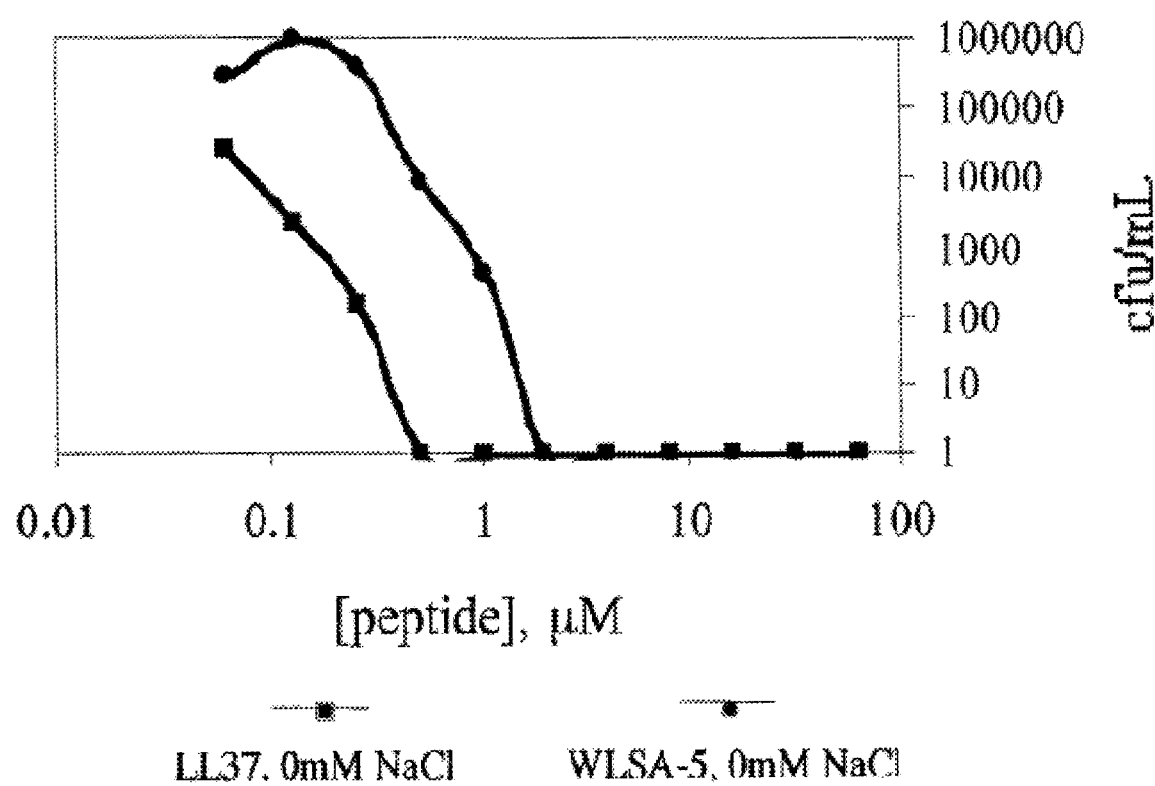
FIG. 3 shows the activity of the peptide WLSA-5 (SEQ ID NO: 3) in comparison with LL37 against P. aeruginosa in the standard broth dilution assay employing phosphate buffer (low salt conditions).
Figure 4:
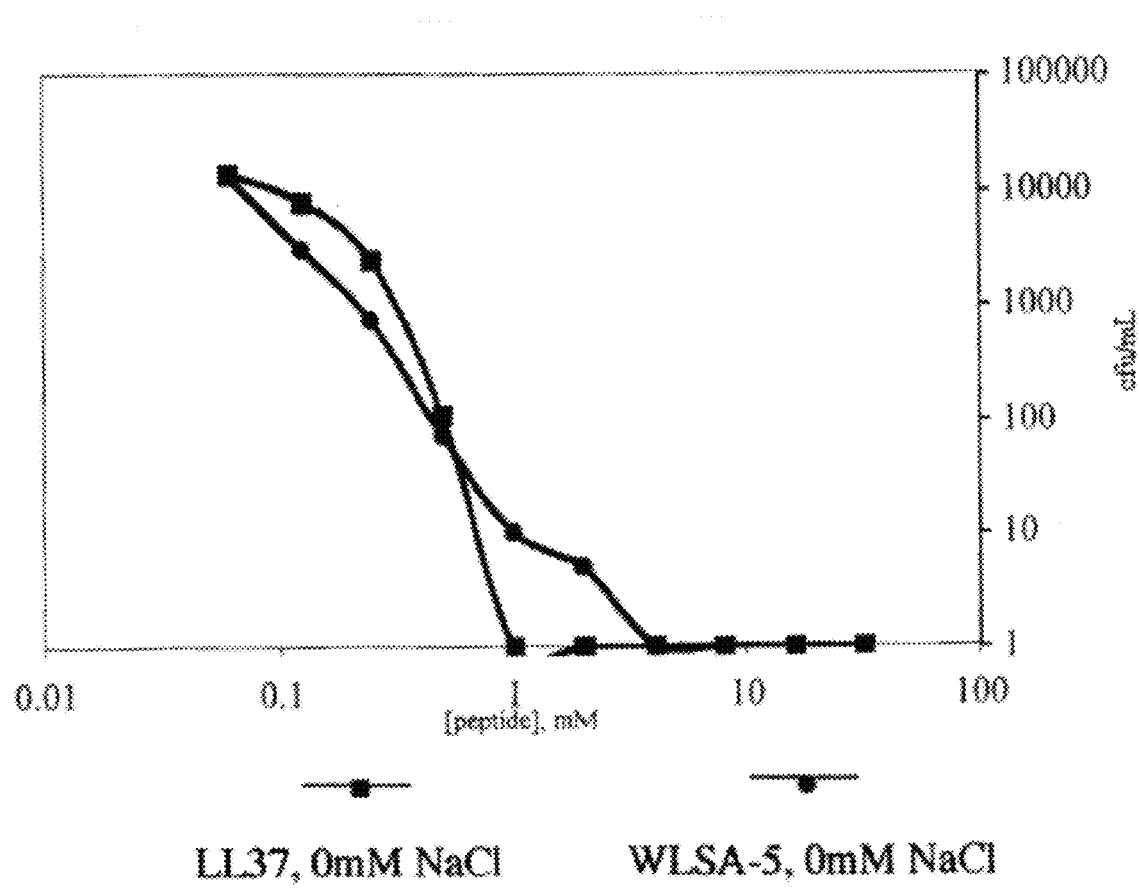
FIG. 4 demonstrates the activity of the peptide WLSA-5 (SEQ ID NO: 3) in comparison with LL37 against S. aureus in the standard broth dilution assay employing phosphate buffer (low salt conditions).

Results. Representative gram positive (*S. aureus*) and gram negative (*P. aeruginosa*) clinical isolates were used as the index bacteria to survey the peptides described herein. Killing curves of LL37 and WLSA-5 (SEQ ID NO: 3) for *S. aureus* and *P. aeruginosa* are shown in FIGS. 3 and 4. These results were reflective of the other peptides described herein. This analysis demonstrated that the antimicrobial peptides described herein were as effective as killing the index bacteria as the host derived antimicrobial peptide, LL37.

Figure 5:
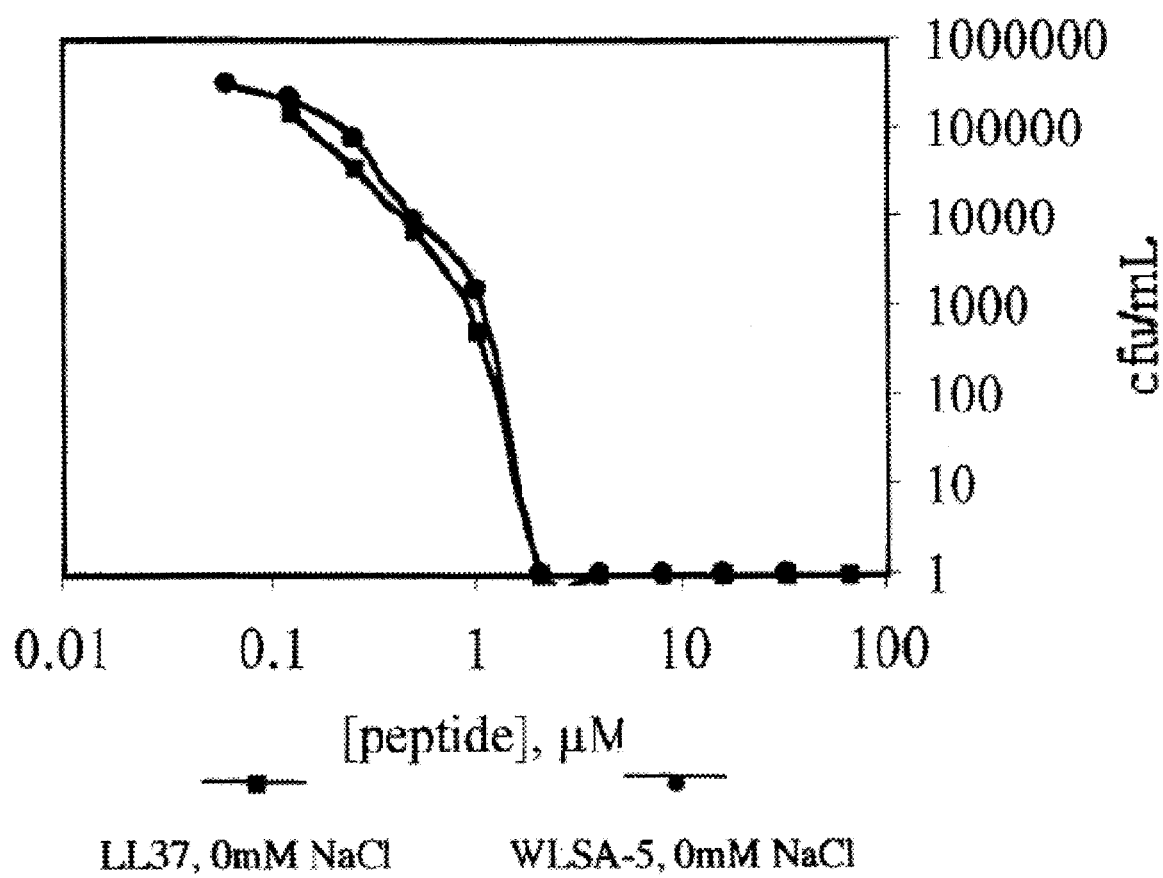
FIG. 5 shows the activity of the peptide WLSA-5 (SEQ ID NO: 3) in comparison with LL37 against P. aeruginosa in the standard broth dilution assay employing phosphate buffer containing 150 mM NaCl (physiologic salt conditions).
Figure 6:
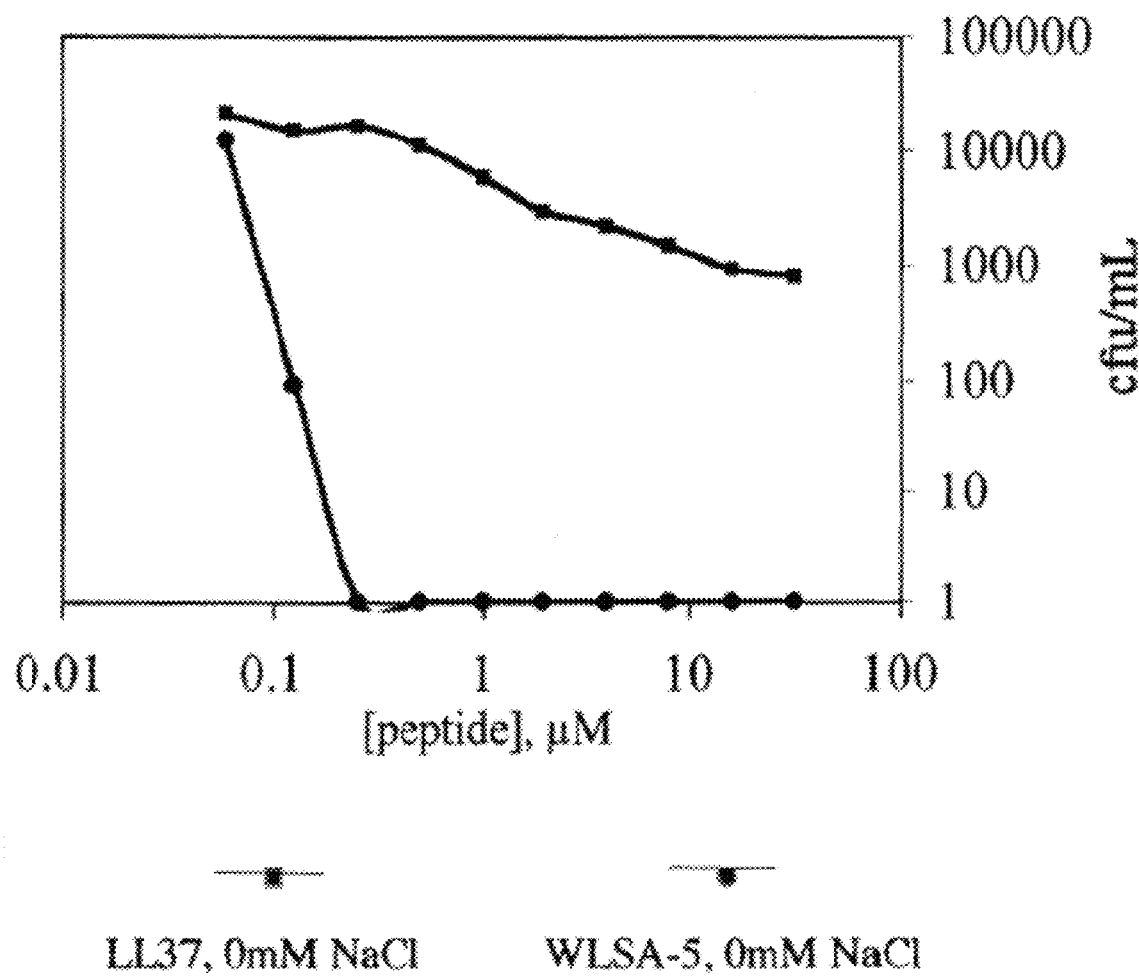
FIG. 6 shows the activity of the peptide WLSA-5 (SEQ ID NO: 3) in comparison with LL37 against S. aureus in the standard broth dilution assay employing phosphate buffer containing physiologic NaCl.

A limitation of many host-derived antimicrobial peptides is their decreased activity at physiologic (150 mM) NaCl concentration. See Friedrich et al., *Antimicrobial Agents and Chemotherapy* 43:1542-1548. The peptides WLSA-5 (SEQ ID NO: 3) and LL37 were tested against the two index strains at physiologic NaCl. The results of these experiments are shown in FIGS. 5 and 6. The results of these experiments demonstrated that WLSA-5 (SEQ ID NO: 3) was not influenced by NaCl in the same way as LL37 when *S. aureus* was used as the test bacterium. *P. aeruginosa* killing was not affected by NaCl inclusion for either peptide. These analyses suggest that the antimicrobial peptides described herein are not as sensitive to the presence of ions as host derived antimicrobial peptides. The activity of antimicrobial peptides described herein were compared to an expanded list of clinical bacterial isolates. These are summarized in Table 2 by comparing their MBCs in phosphate buffer alone (low salt) and phosphate buffer containing 150 mM NaCl (physiologic conditions). Inspection of this table would lead one skilled in the art to conclude that the activity of antimicrobial peptides described herein compare favorably to the host derived antimicrobial peptides as it relates to the spectrum and potency of antimicrobial activity.

Example 3

Cystic Fibrosis Cell Culture Model of Selective Toxicity

Preparation of bacterial cells. *Burkholderia cepacia* and *P. aeruginosa* isolates were obtained from clinical microbiology laboratories and assayed using the broth dilution method as described in Example 2.

Preparation of Eukaryotic Cells. Differentiated Primary Cell Cultures of Human Bronchial Epithelial (HBE) cells (CF and non-CF) on an air-liquid interface were prepared in antibiotic free media. See Zabner, J. et al., 1996, *J. Virol.* 70:6994-7003. These filters were incubated with *P. aeruginosa* followed by washing to remove non-adherent bacteria. Individual filters were next exposed to peptide at increasing concentrations. In order to release viable bacteria, trypsin/EDTA was added and these preparations were plated on standard bacteriologic media to quantify bacterial survival. Similarly prepared cells were monitored for peptide toxicity by measuring transepithelial resistance. The advantage of this model is that it can measure the selective toxicity of peptide for bacterium versus host cells under identical conditions.

Results. LLP-1 and its derivatives, SA-5 (SEQ ID NO: 1), LSA-5 (SEQ ID NO: 2) and WLSA-5 (SEQ ID NO: 3) were tested for their bactericidal activity against pathogens typically associated with CF airway disease, namely, *S. aureus, P. aeruginosa*, and *B. cepacia*. Low (10 mM Phosphate buffer (PB)) and physiologic salt (10 mM PB containing 150 mM NaCl) concentrations were used as variable conditions under which peptide activity was tested using the standard broth dilution assay described in Example 2. Kill curves similar to those demonstrated in FIGS. 3-6 were generated and MBC values determined as described above. The MBC values for *S. aureus* and *P. aeruginosa* are summarized in Table 2. Of the peptides tested, WLSA-5 (SEQ ID NO: 3) maintained its activity in low and physiologic salt conditions against these two index strains.

Figure 7:
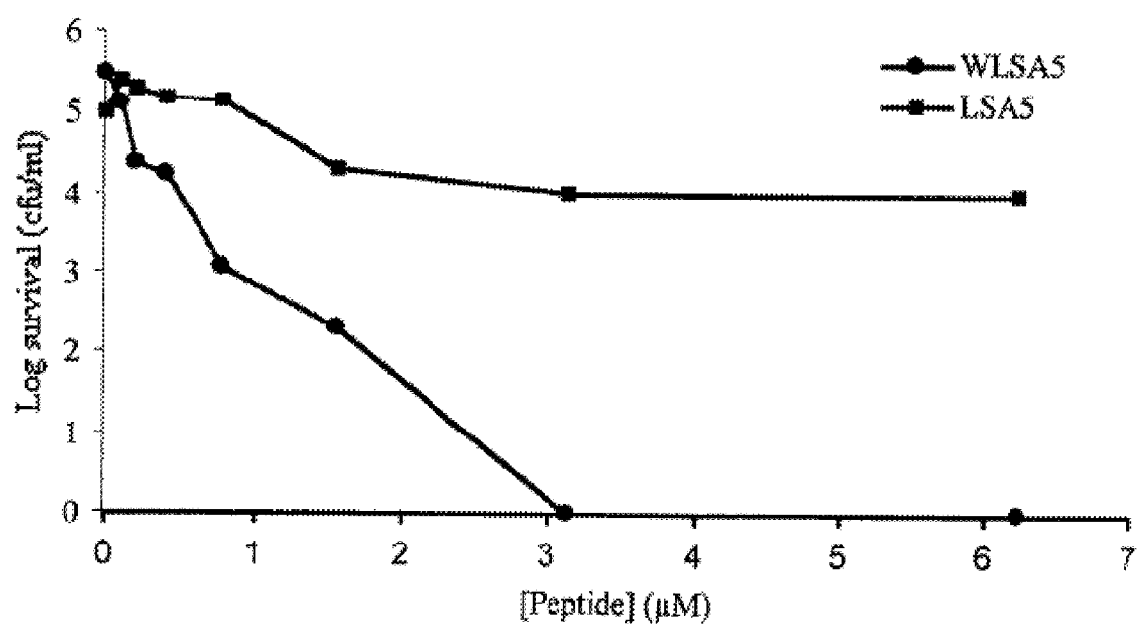
FIG. 7 demonstrates in a standard broth dilution model that WLSA-5 (SEQ ID NO: 3) is more active than LSA-5 (SEQ ID NO: 2) against Burkholderia cepacia, a notoriously antibiotic resistant bacterium associated advanced cystic fibrosis lung infection.
Figure 8:
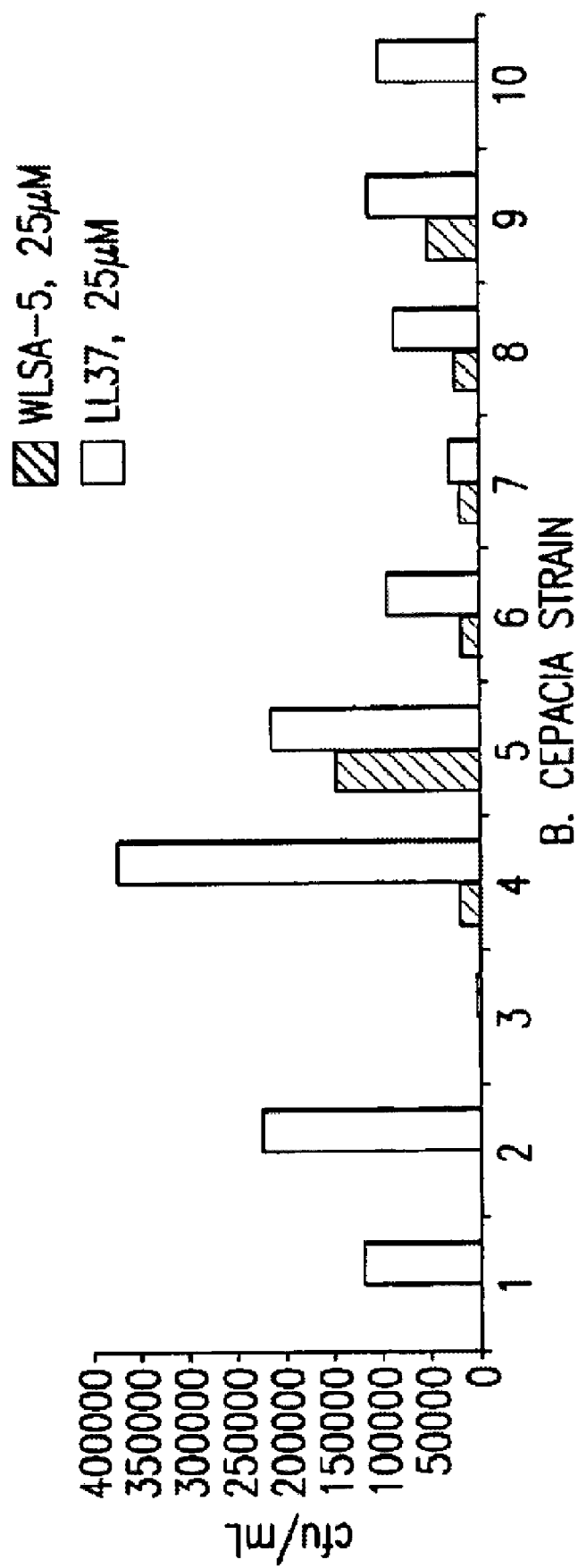
FIG. 8 compares the ability of 25 µM WLSA-5 (SEQ ID NO: 3) or LL37 to kill multiple genomovars of B. cepacia. In this experiment, a standard inoculum of each organism was exposed to a single concentration (25 µM) of WLSA-5 and LL37 and the reduction in colony forming units determined.

WLSA-5 (SEQ ID NO: 3) was tested and compared with LSA-5 (SEW ID NO: 2) for activity against *B. cepacia*, an important bacterial pathogen associated with CF airway disease. As shown in FIG. 7, WLSA-5 (SEQ ID NO: 3) was significantly more active than LSA-5 (SEQ ID NO: 2) against *B. cepacia*. It has been generally reported that this organism is resistant to the activity of most antimicrobial peptides so the finding that WLSA-5 (SEQ ID NO: 3) demonstrated significant in vitro activity. To test whether this activity was specific for the clinical isolate of *B. cepacia* tested in FIG. 7 or generally applicable to diverse *B. cepacia* isolates, a survey study was designed. For this study a collection of well-characterized *B. cepacia* genomovars were obtained and tested for susceptibility to killing by 25 µM WLSA-5 (SEQ ID NO: 3). This was compared to the host antimicrobial peptide, LL37, at the identical concentration. The data shown in FIG. 8, is represented as the number of organisms surviving after treatment under these conditions. The results demonstrated that WLSA-5 (SEQ ID NO: 3) was equal to or better than LL-37 at killing all bacterial strains within this collection. This finding suggests that WLSA-5 (SEQ ID NO: 3) may be effective when administered in a CF setting where *B. cepacia* is the principal etiologic agent precipitating lung disease in CF patients.

Figure 9:
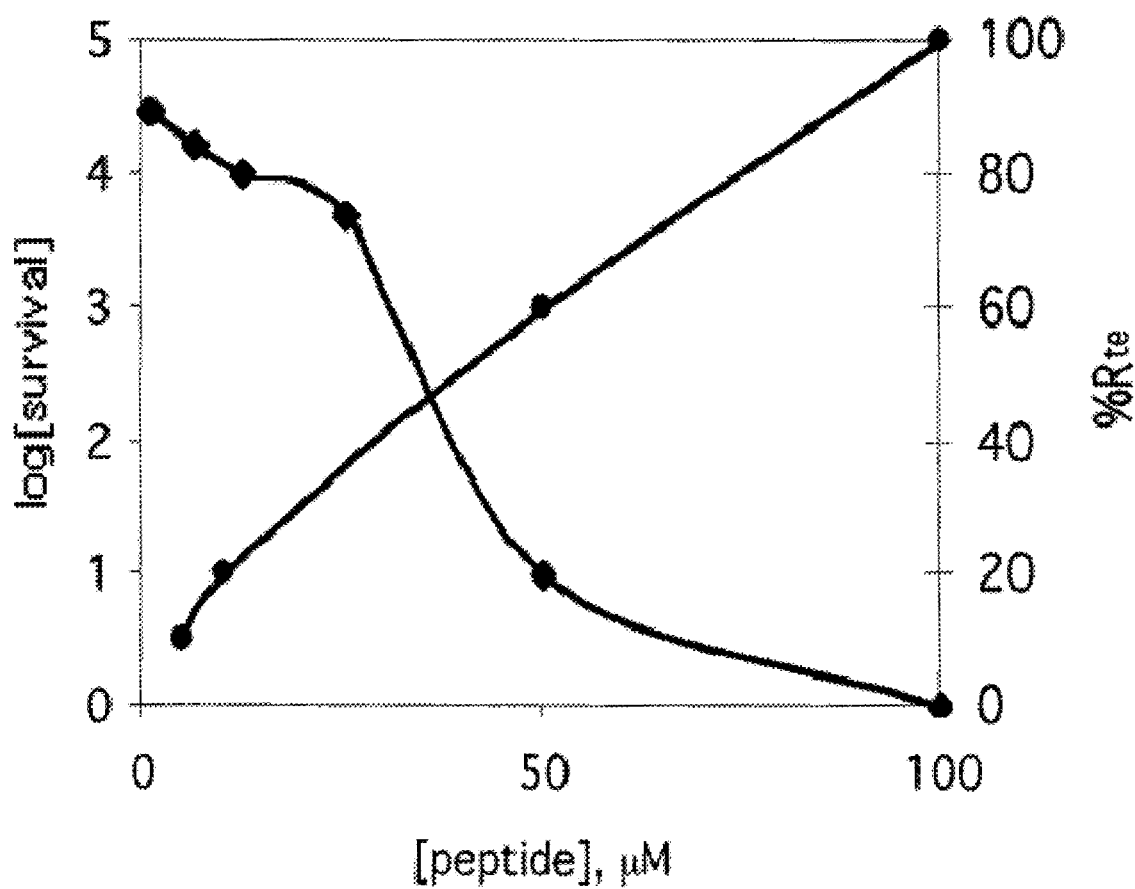
FIG. 9 shows the antibacterial activity of WLSA-5 (SEQ ID NO: 3) against Pseudomonas aeruginosa attached to differentiated human bronchial epithelial cells in comparison with LL37, the host derived antimicrobial peptide found in the airway surface fluid. This data demonstrates that WLSA-5 is active in this model of cystic fibrosis lung infection. The circles measure % Rte (% change in transepithelial resistance). The squared measure the surviving bacteria.

Based on above in vitro findings, WLSA-5 (SEQ ID NO: 3) was tested in a scenario that more accurately assessed its selective toxicity. For this assay, a cell culture model of bacterial adherence was established that utilized differentiated primary human airway epithelial cells. These cells were exposed to a standard inoculum of *P. aeruginosa* and bacteria and epithelial cells in co-culture were treated with different concentrations of test peptide. The ability of peptide to kill bacteria is monitored as a function of viable bacteria associated with the epithelial cells after peptide exposure. In order to assess epithelial cell toxicity, measurements of transepithelial resistance were performed. Differentiated airway epithelial cells in culture form tight junctions that are refractory to electrical current unless the monolayer is compromised by an event such as epithelial cell damage. Thus, measurement of transepithelial resistance can be used as a sensitive measure of peptide toxicity. FIG. 9 depicts the results of an experiment in which increasing concentrations of WLSA-5 (SEQ ID NO: 3) were added to bound *P. aeruginosa* and epithelial cells in co-culture. A decrease in bacterial viability and increase in trans epithelial resistance (Rte) was demonstrated as a function of peptide concentration. A decrease in bacterial counts by two orders of magnitude resulted in a change in transepithelial resistance of less than 50%. Furthermore, the effect of WLSA-5 (SEQ ID NO: 3) on trans-epithelial resistance was transient and not significantly different from LL-37. These data suggest that WLSA-5 (SEQ ID NO: 3) demonstrates selective bacterial toxicity in a CF setting.

Example 4

Rabbit Joint Model of Septic Arthritis

Figure 10:
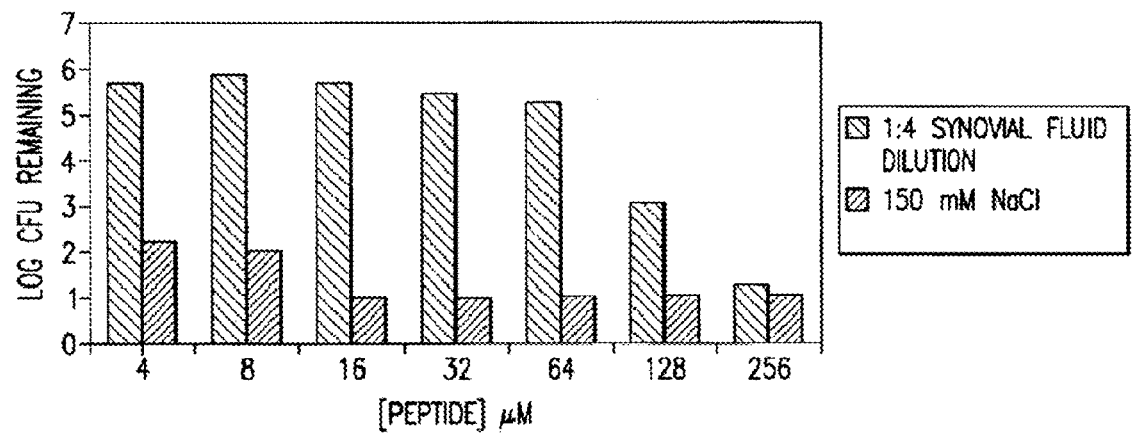
FIG. 10 is a bar graph comparing the bactericidal activity of LSA-5 (SEQ ID NO: 2) against S. aureus in a 1:4 dilution of human synovial fluid (light bars) and compares it with killing in phosphate buffer containing physiologic NaCl. The data suggests that components of synovial fluid limit the activity of the peptide, but that it is still active at 128 µM.
Figure 11:
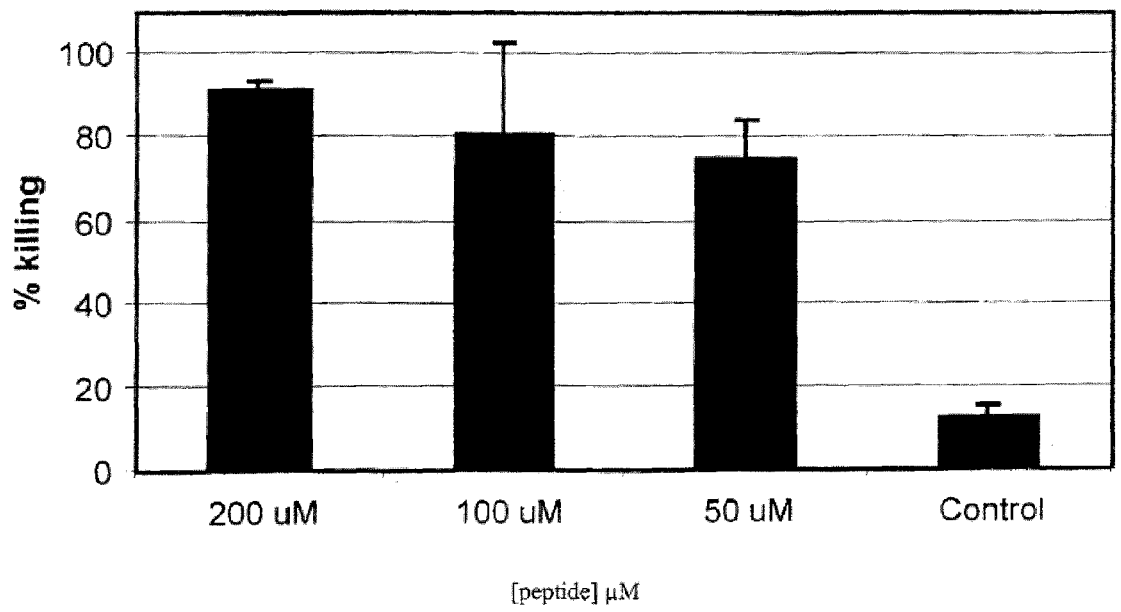
FIG. 11 demonstrates that, in the rabbit joint sepsis model, administration of LSA-5 (SEQ ID NO: 2) at 50, 100 and 200 µM significantly increases bacterial killing.

We have demonstrated that LSA-5 (SEQ ID NO: 2) is highly active against *S. aureus* (Table 2) and *S. epidermidis* in vitro, two common causes of joint infections, and can function in the presence of biologic fluids such as that derived from the joint synovium (FIG. 10), although the presence of synovial fluid clearly impairs the activity of LSA-5 (SEQ ID NO: 2). We have extended these findings to a septic arthritis animal model. In this study joint sepsis was induced by inoculating one knee of a 2.5 Kg New Zealand white rabbit with $1\times10^5$ colony forming units of a clinical *S. aureus* isolate, a strain resistant to penicillin but sensitive to methicillin, cephalosporins, and clindamycin. Using this model, symptoms of septic arthritis (e.g., degradation of the synovium) were monitored and the ability of antimicrobial agents to limit the degeneration of the joint post-infection can be assessed. In this application the bacterial infection is allowed to establish for 1 h. At this point the joint was accessed and increasing concentrations of LSA-5 (SEQ ID NO: 2) (0, 50, 100, and 200 µM) in phosphate buffer (PB) was administered intraarticularly. The concentration of bacteria associated with joint fluid was established at time 0 and 1 h post LSA-5 (SEQ ID NO: 2) instillation by plating dilutions of the synovial fluid on LB agar. The results of this experiment demonstrated a dose-dependent decrease in colony forming units compared to the non-peptide treated joint when examined after 1 h (FIG. 11).

Figure 12:
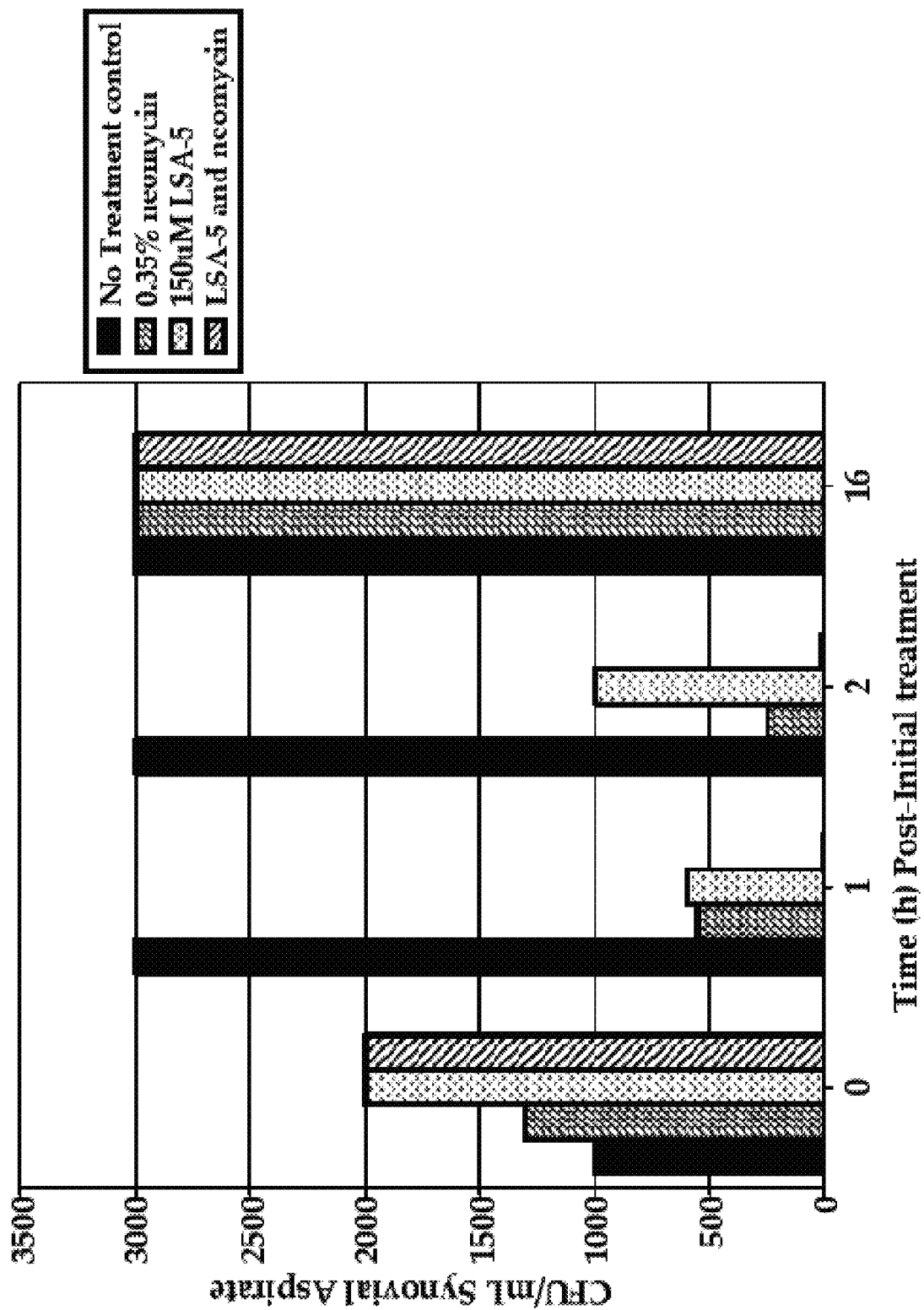
FIG. 12 illustrates that in the rabbit joint sepsis model, LSA-5 (SEQ ID NO: 2) is functional and nearly as effective as a standard concentration of neomycin at reducing the bacterial load within the joint. When used in combination with neomycin, a maximal decrease in bacterial load was observed.

In order to demonstrate that successive doses of LSA-5 (SEQ ID NO: 2) can be efficacious for limiting bacterial load in this rabbit model, administration of two peptide treatments of 150 µM LSA-5 (SEQ ID NO: 2) at times 0 and 1 h was evaluated. Measurement of the bacterial load 1 h post-treatment demonstrated a significant decrease in the peptide treated joints when compared to joints treated with phosphate buffer in the absence of peptide. This was compared with multiple injections of a standard 0.35% neomycin or a combination of neomycin and LSA-5 (SEQ ID NO: 2). Administration of each of these formulations was performed intraarticularly at time 0, 1, and 2 h. The results of this experiment demonstrated that when compared to groups treated with LSA-5 (SEQ ID NO: 2) or neomycin alone, substantially fewer bacteria were recovered from the joint treated with the of LSA-5/neomycin combination (FIG. 12). Furthermore, in all of these animal experiments no adverse toxicity was observed when peptide was administered alone. These data mimic chronic infection associated with septic arthritis and suggest that topical treatment can be initially effective.

One potentially important application for the antimicrobial peptides described herein as it relates to septic arthritis is their activity when bound to a solid phase substrate such as a prosthetic joint. To address this, the amino terminal group of LSA-5 (SEQ ID NO: 2) was covalently attached to an Affigel™ 15 (BioRad, Hercules, Calif.) resin. This permeable solid support was placed in a small column and exposed to 1 mL suspension of a $\times 10^6$ bacteria/mL. The solution was allowed to pass by gravity through the column and the eluant collected and quantitated for the number of viable bacteria. As a negative control, an identical column was prepared except that a non-antimicrobial peptides was attached in place of LSA-5 (SEQ ID NO: 2). The results are summarized in Table 3 below and demonstrate that either a suspension of *P. aeruginosa* or *S. aureus* were completely sterilized by exposure to the column. In contrast, no reduction in viable bacteria was observed after exposure to the non-antimicrobial peptide control column. Furthermore, the same LSA-5 (SEQ ID NO: 2) column could be repeatedly exposed to bacterial suspensions and it maintained activity for up to 6 passages. These data suggest the possibility that prosthetic joints could be coated with the antimicrobial peptides described herein to inhibit the nucleation of biofilm formation observed in joint replacement surgery which leads to septic arthritis.

TABLE 3

| | Input Bacteria | | | |
|---|---|---|---|---|
| | P. aeruginosa | | S. aureus | |
| Peptide | LSA-5 | Control | LSA-5 | Control |
| Bacterial count prior to column exposure | $1 \times 10^6$ | $1 \times 10^6$ | $1 \times 10^6$ | $1 \times 10^6$ |
| Bacterial count from eluant | 0 | $1 \times 10^6$ | 0 | $1 \times 10^6$ |

Example 5

Suppression of Hiv-1 Infectivity

Based on the observation that the peptides described herein were active against certain eukaryotic cell membranes (e.g., demonstrated to lyse erythrocytes) it was reasoned that certain antimicrobial peptides described herein may be active in suppressing the infectivity HIV-1. Proof for this concept was obtained by studying the ability of an LLPI peptide, LSA-5 (SEQ ID NO: 2) to inhibit the infectivity of HIV-1 similar to that previously shown for cationic host-derived antimicrobial peptides (Wachinger, M., et al. (1998) *Journal of General Virology* 79:731-40; Wachinger, M., T. Saermark and V. Erfle (1992) *FEBS Letters* 309:235-41; Robinson, W. E., Jr., B. McDougall, D. Tran and M. E. Selsted (1998) *Journal of Leukocyte Biology* 63:94-100; Yasin, B. et al. (2000) *European Journal of Clinical Microbiology & Infectious Diseases* 19:187-94).

In this example human peripheral blood monocytes (PB-MCs) were obtained from healthy volunteers and maintained in culture at a concentration of $1\times10^5$ viable cells per mL of medium. These cells were stimulated by the addition of phytohemagglutinin (PHA). To this a standardized titer of purified HIV-1 (strain IIIB) virions was added to PBMCs to generate a p24 antigen signal of 14,000 pg/mL five days post exposure to virus.

In order to test whether the LLP peptide, LSA-5 (SEQ ID NO: 2) was able to suppress HIV-1 activity, LSA-5 at concentrations ranging between 0.1 and 100 µM were incubated with the standard virus titer determined as above for 30 min. Virions surviving peptide exposure were isolated by ultracentrifugation at 100,000×g for 60 min. Viral pellets were used to infect PHA stimulated PBMCs prepared as described above. Five days post infection the level of p24 antigen was determined and compared to a non-peptide treated control. The data was expressed as the ratio of p24 antigen associated with peptide-treated vs. non-peptide treated HIV-1 infected cells to obtain a value referred to as percent suppression.

Figure 13:
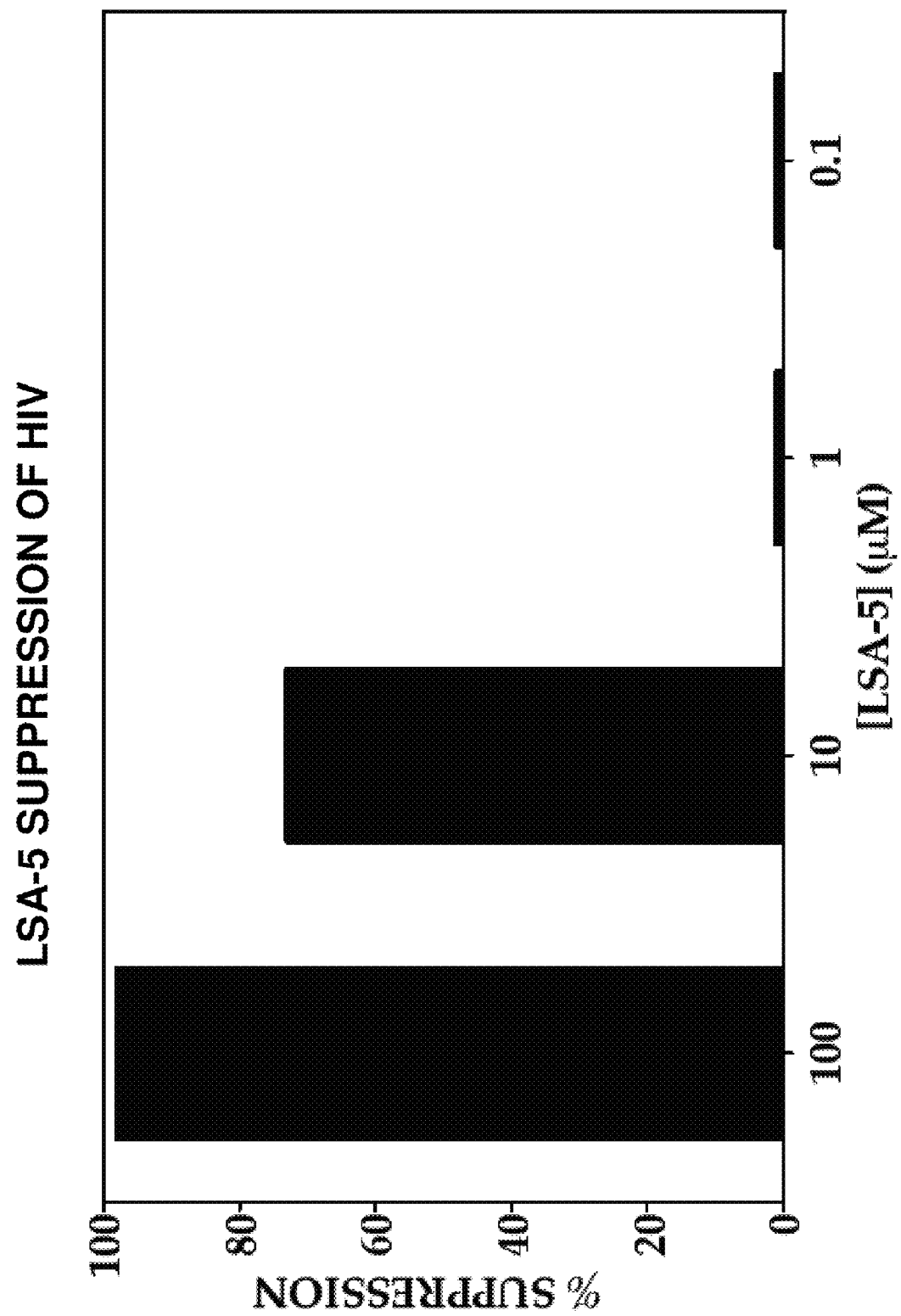
FIG. 13 shows a bar graph which illustrates that an exemplary embodiment of the peptides described herein, LSA-5 (SEQ ID NO: 2), has anti-HIV-1 activity.

As shown in FIG. 13, LSA-5-treated virions alone at 100 µM reduced HIV-1 infectivity by nearly 100%. At 10 µM, HIV-1 infectivity was reduced by 75%. At 1 and 0.1 µM there is a drop off this inhibitory activity of LSA-5. Experiments not described herein employing other peptides described by this invention demonstrate that those peptides observed to have a high hemolytic activity for red cells were more active on a molar basis against HIV-1 virions than those with low hemolytic activity. These data demonstrate that the LLP peptides of the present invention are active against enveloped viruses, and particularly, HIV-1, and can be engineered for increased potency in this setting.

Example 6

Antiviral Activity of eCAPS

The antibacterial activity of LLPs can be modulated by the length of the peptides, as well as their Arg and Trp content. The present example evaluates the anti HIV activity of LBU, WLBU and WR (eCAP) peptides.

Figure 14:
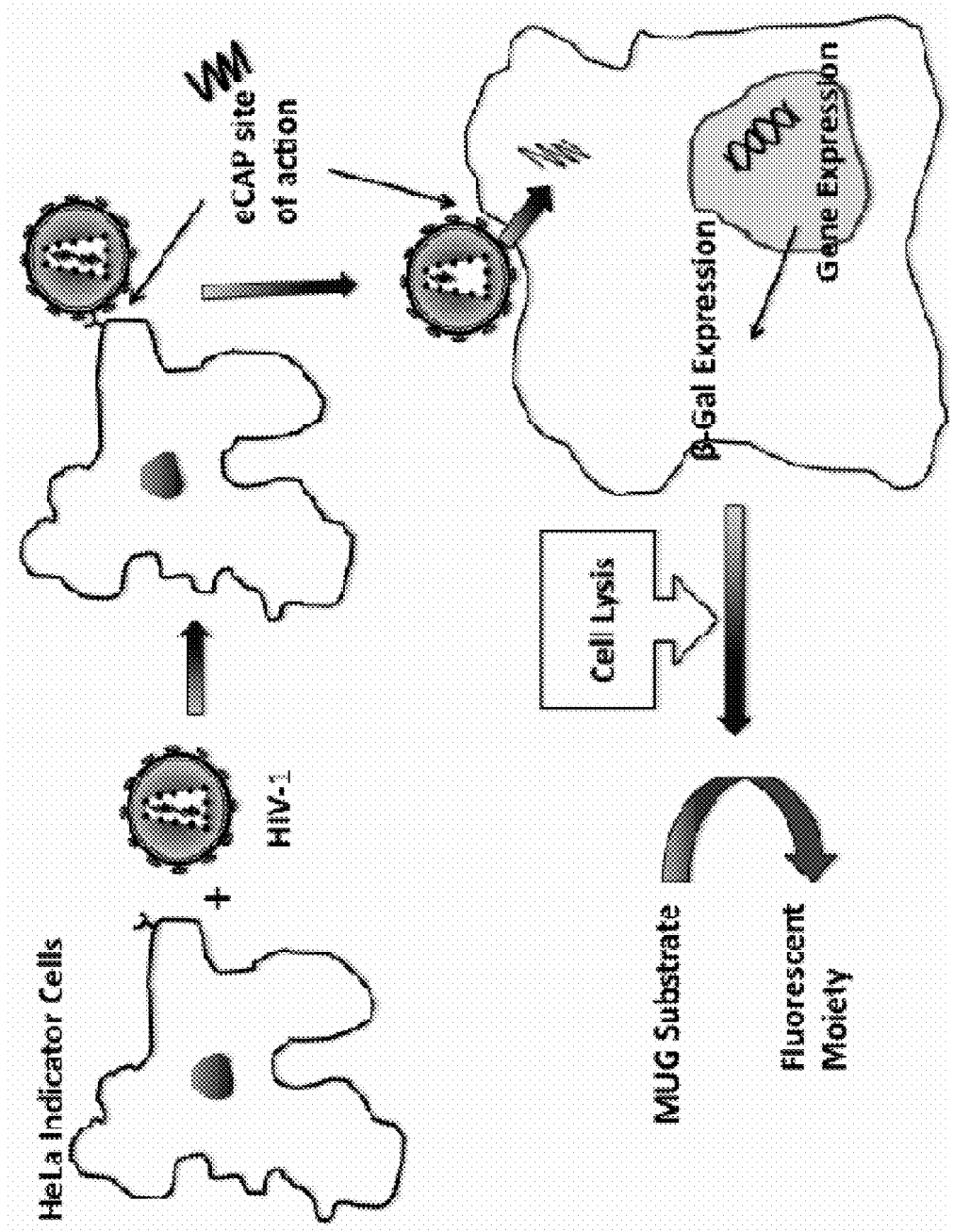
FIG. 14 is a description cartoon showing a cell-based assay for measuring the activity of various peptides described herein in reducing HIV-1 infectivity.
Figure 15:
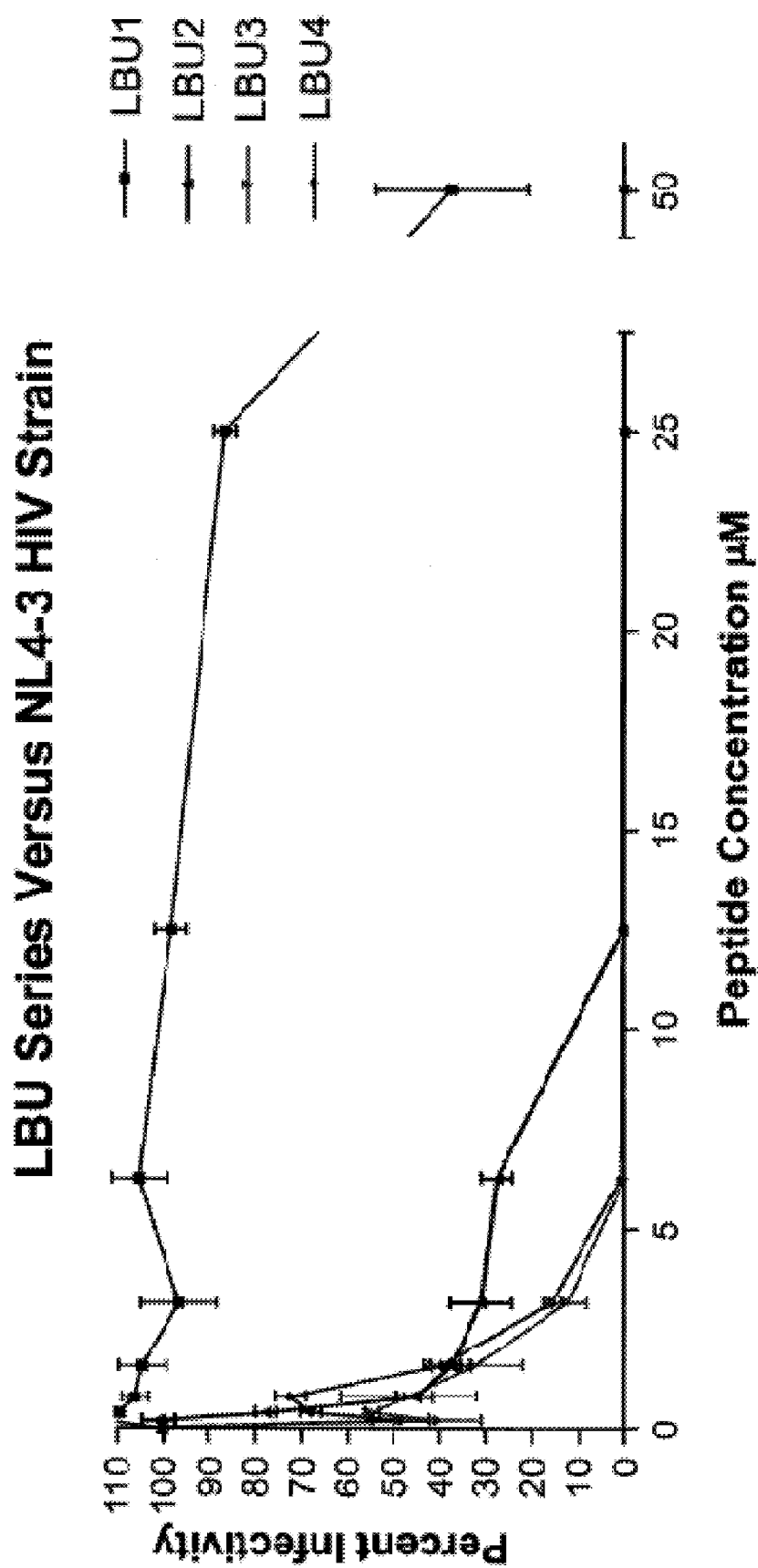
FIG. 15 is a graph showing the activity of LBU peptides in inhibiting HIV-1 infectivity of HeLa cells.

The assays were carried out to measure HIV infection of HeLa indicator cells in the presence of increasing concentrations of peptides. FIG. 14 provides a general scheme of the assay. Peptides were prepared in media at concentrations ranging from 0 to 50 µM. The HeLa cells were inoculated with HIV-1. After 2 days, the cells were lysed and β-galactosidase activity was measured as a function of HIV-1 infectivity. Measurements were compared to a positive control to determine $IC_{50}$ (the inhibitory concentration of peptide required to reduce viral infectivity of 50%).
Materials and Methods HeLa indicator cells were plated on a 96 well palate and allowed to adhere for 24 hours. Peptides were prepared in media in concentrations ranging from 0-50 µM. Media from each well was replaced by media continuing peptide. NL4.3 HIV-1 strain was inoculated into each well and plates were allowed to incubate for 48 hours at 37° C. The cells were lysed and 4-methylumbelliferyl-beth-D-glucuronide (MUG) was added as a substrate for β-galactosidase. The fluorescence generated was read in a fluorometer.
Results FIG. 15 graphically shows the results of inhibiting viral infectivity by the LBU series of peptides (LBU1, LBU2, LBU3 and LBU4 (SEQ ID NOS: 4, 5, 6 and 8, respectively). FIG. 16 presents a comparison of the $IC_{50}$ of each peptide to the concentration where visual toxicity is seen.

Figure 17:
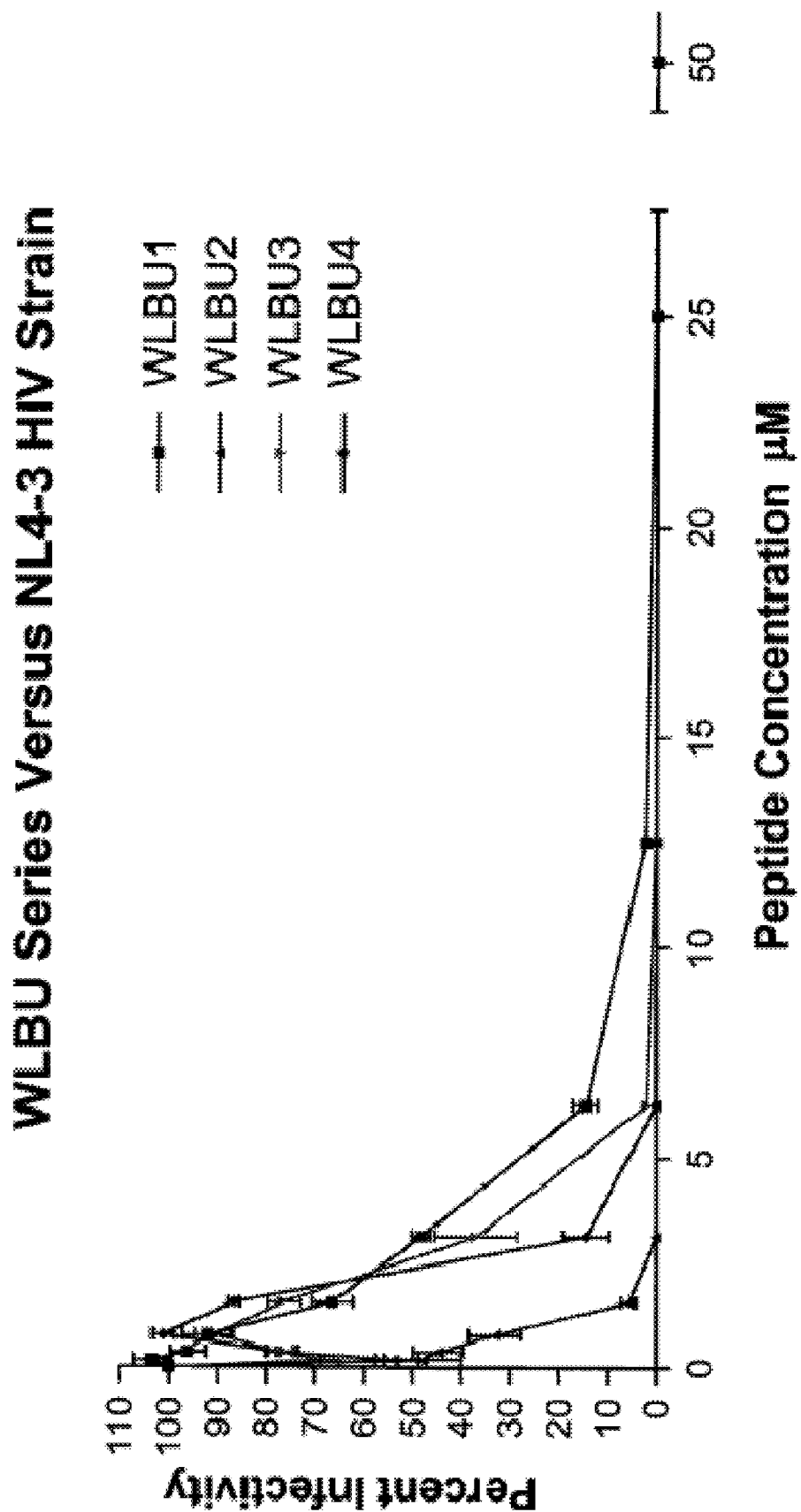
FIG. 17 is a graph showing the activity of WLBU peptides in inhibiting HIV-1 infectivity of HeLa cells.

FIGS. 17 and 18 show the $IC_{50}$ and toxicity levels for the WLBU peptides (WLBU 1, WLBU-2, WLBU3 and WLBU4 (SEQ ID NOS: 4, 5, 6 and 8, respectively)).

Figure 19:
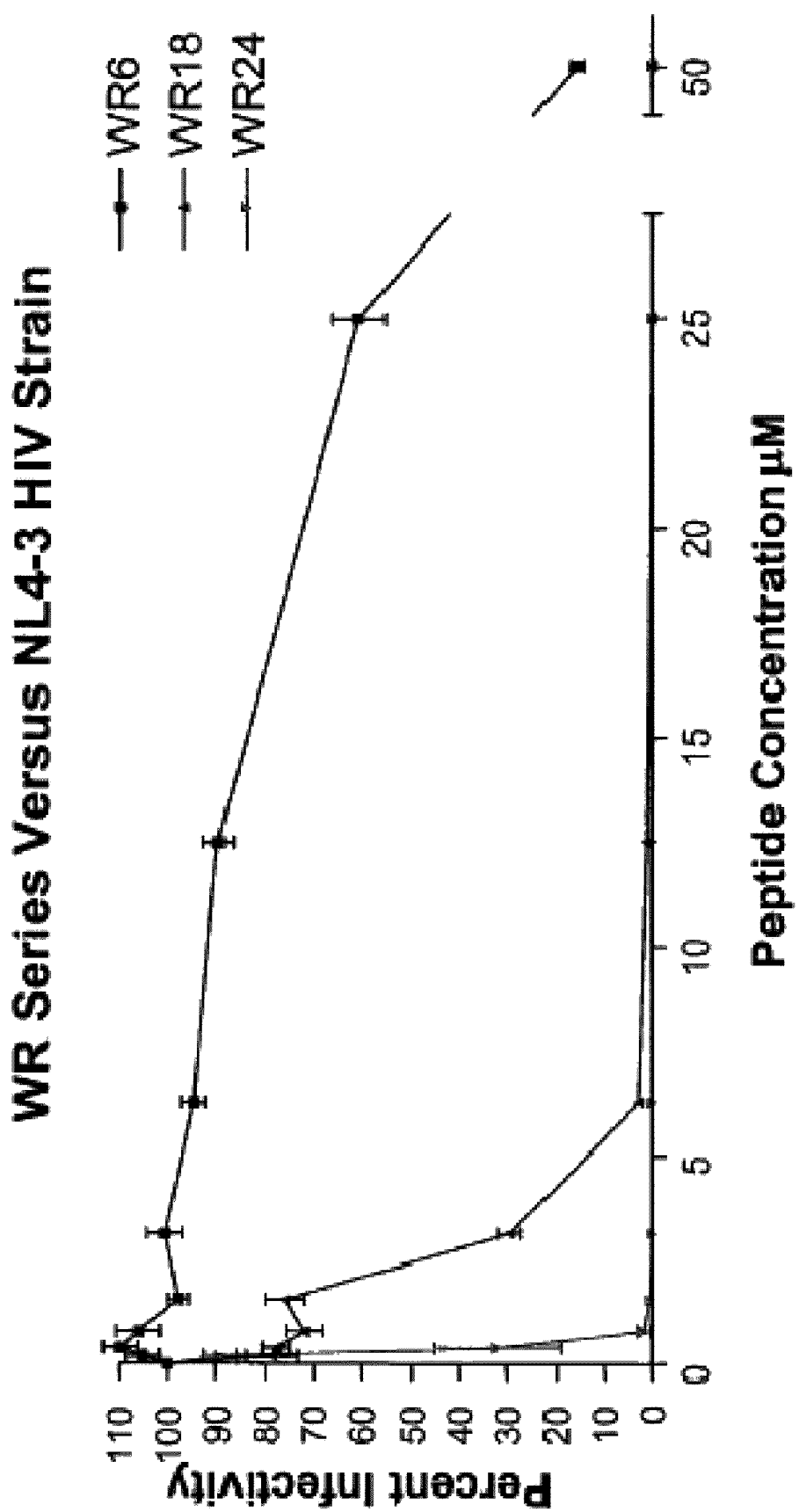
FIG. 19 is a graph showing the activity of WR peptides in inhibiting HIV-1 infectivity of HeLa cells.

FIGS. 19 and 20 show the $IC_{50}$ and toxicity levels for three of the WR peptides (WR6, WR18 and WR24 (SEQ ID NOS: 13, 15 and 16, respectively)). The WR peptides, having additional tryptophan residues, showed enhanced antiviral activity with increasing length.

Example 7

Figure 21:
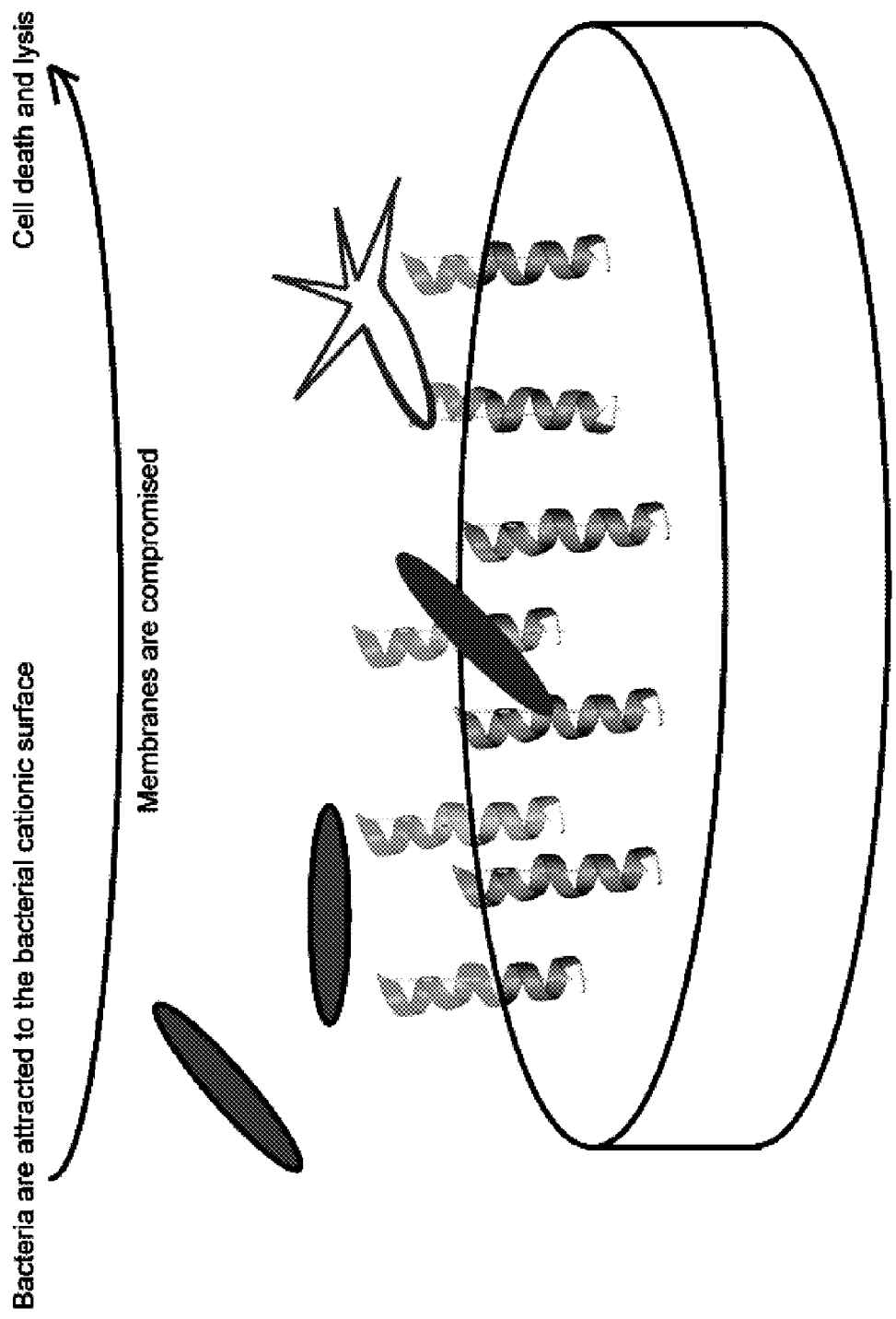
FIG. 21 is an illustration demonstrating peptide bound to a surface can act like a "pin popping a balloon". Coating surfaces with these peptides can be useful in controlling growth of bacteria or other microbes that form biofilms on surfaces.

Peptides as Potent Antimicrobials Tethered to a Solid Surface: Implications for Medical Devices Medical devices are an integral part of therapeutic management; as important of these tools are, they carry with them a significant risk of microbial infection. Bacterial attachment to an invasive medical device typically is established by a single, multiplying organism, leading to subsequent biofilm formation. To date preventative measures have not significantly impacted the reduction of infections. In this example, the bidirectional covalent coupling of an engineered cationic antimicrobial peptide, WLBU-2 (SEQ ID NO: 10), to various biological surfaces is accomplished (see, FIG. 21 for a schematic illustration of this process). These surfaces include (i) a carbohydrate-based gel matrix, (ii) a complex polymeric plastic bead, and (iii) a silica-calcium phosphate nanocomposite associated with bone reconstruction. WLBU-2-conjugated surfaces are shown to retain potent antimicrobial activity related to bacterial surface adhesion. This example provides proof of principle that covalently coating laboratory and bone-regenerating materials, as well as surfaces of any device that can be inserted, implanted, etc. in or on a subject (e.g., a patient), with the antimicrobial peptides described herein has the potential for decreasing infectious consequences. These findings have important consequences to the medical device and patient management component of our current health care technology.

The membrane-active properties of the antimicrobial peptides could lead to decreased adhesion and subsequent development of bacterial biofilm formation on medical devices. The implications of such surface-active antimicrobial activity would have a significant impact on the medical device industry. For example, any medical device that is introduced into a subject may benefit from this activity, including, without limitation: intravenous catheters, cannulae, dialysis ports, staples, sutures, artificial bone or dental implants, prosthetic joints, heart valves, stents, cardiac pacemakers and cerebrospinal fluid shunts, which have become essential to the medical field and in every case are at risk for infections. In each of these, nucleation with progression to biofilm formation on the medical device is considered the basis for systemic infection (von Eiff, C., Jansen, B., Kohnen, W. & Becker, K. Infections associated with medical devices: pathogenesis, management and prophylaxis. *Drugs* 65, 179-214 (2005) and Falagas, M. E., Fragoulis, K., Bliziotis, I. A. & Chatzinikolaou, I. Rifampicin-impregnated central venous catheters: a meta-analysis of randomized controlled trials. *J Antimicrob Chemother* 59, 359-369 (2007)). As a result, disrupting the potential nucleation on a device will disrupt the natural progression to disease.
Materials and Methods:

Preparation of bacteria. Luria broth (LB) was inoculated with a colony of *P. aeruginosa* (strain PA01) and incubated overnight at 37° C. with shaking. The next morning, 5 mL of the overnight culture was transferred into 20 mL of LB broth and incubated for another 2 hours at 37° C. with shaking. 10 mL of the second incubation culture was pelleted and suspended in 10 mL of phosphate buffered saline (PBS) at pH of 7.8. The $A_{600}$ of the suspended bacterial solution was read, and the solution was further diluted to a concentration with an $A_{600}$=0.001 in PBS. The *S. aureus* strain used in this study has been described previously publications (Deslouches, B. et al. De novo generation of cationic antimicrobial peptides: influence of length and tryptophan substitution on antimicrobial activity. *Antimicrob Agents Chemother* 49, 316-322 (2005)) and was prepared identically as described for the *P. aeruginosa* strain above.

WLBU-2 N terminal Coupled to Affigel beads. A calculated amount of WLBU-2 stock solution was added to 10 mL of Affigel resin (Affigel 10—NHS chemistry, 10 stands for a "10 carbon linker" that attaches to the free amino group on WLBU2 (SEQ ID NO: 10), Bio-Rad Laboratories) extracted from slurry to obtain a total concentration of 10 μM in the suspension. A sample of the WLBU-2 (SEQ ID NO: 10) stock was separated for later comparison. The manufacturing protocol was followed under aqueous conditions at room temperature for 2 h. A sample of the supernatant was separated and used for analysis of WLBU-2 (SEQ ID NO: 10) coupling. After successful attachment of WLBU-2 (SEQ ID NO: 10) to Affigel beads (Affigel-WLBU-2 beads), a 3 cm column was generated. The column was washed with PBS prior to running a PA01 bacterial suspension prepared as described previously. The resulting suspension was plated, incubated overnight at 37° C. and cfu determined.

Analysis of WLBU-2 (SEQ ID NO: 10) coupled to Affigel beads. The extent of coupling of WLBU-2 to the Affigel beads was monitored by reverse phase HPLC analysis of the reaction media both before and after conjugation. The analysis was performed using a Waters Alliance 2695 chromatography system and a Waters 2487 Dual Absorbance Detector. Samples were injected onto a Phenomenex Gemini 5μ C-18 column (250×4.6 mm) and eluted with solvent A (0.1% TFA in $H_2O$) and solvent B (0.08% TFA in acetonitrile) at a flow rate of 1 mL/min. Peak detection at 220 nm was followed by data acquisition and integration using a Waters Empower software package. The amino acid composition of the agarose beads generated a high degree of background noise as described by Palate et al (Palace, G. P., Fitzpatrick, R., Tran, K. V., Phoebe, C. H., Jr. & Norton, K. Determination of amino acids in diverse polymeric matrices using HPLC, with emphasis on agars and agaroses. *Biochim Biophys Acta* 1472, 509-518 (1999)). To estimate the substitution rate, the HPLC peaks of the samples obtained pre and post coupling were compared.

WLBU-2 (SEQ ID NO: 10) C terminal Coupled to Tentagel beads. WLBU-2 Tentagel beads were synthesized on an Applied Biosystems 433A peptide synthesizer using standard FMOC chemistry and 0.25 mM FastMoc cycles. Chain elongation was in stepwise fashion on TentaGel S $NH_2$ resin (Peptides International) using FMOC protected amino acid derivatives (Peptides International) containing side-chain protecting groups. Removal of the side chain protecting groups was accomplished using standard TFA (TFA:Triisopropylsilane:$H_2O$) cleavage conditions. This involved treatment of the fully side chain protected peptide resins with cleavage reagents at a concentration of 20 ml/gm for 4 h at room temperature. The WLBU-2 TentaGel beads were then filtered through a Buchner funnel, washed with neat TFA and dried under vacuum. The dried beads were suspended in N,N dimethylformamide (DMF), initially washed with DMF followed by Dichloromethane and allowed to air dry.

Analysis of carboxy terminal WLBU-2 (SEQ ID NO: 10) coupled to Tentagel beads. After completion of hydrolysis of WLBU-2 Tentagel beads, the samples were completely dried under vacuum. Samples were suspended in 60% acetonitrile/ 0.1% TFA in $H_2O$ and sonicated for 20 minutes. The supernatant was dried under vacuum and suspended in 20 mM HCl, followed by derivitization with 6-aminoquinolyl-N-hydroxysuccinimidyl carbamate) using Waters AccQ•Tag analysis kit. Samples were analyzed by chromatography using standard gradient conditions. Fluorescence detection at an excitation wavelength of 250 nm was used to acquire integration peaks.

Binding of WLBU-2 (SEQ ID NO: 10) to Silica-Calcium Phosphate Nanocomposite. Resorbable porous bioactive SCPC with the chemical composition was prepared by heating at 850° C. (This process is essentially as described in El-Ghannam, A, K Ahmed, and M Omran, Nanoporous Delivery System to Treat Osteomyelitis and Regenerate Bone: Gentamicin Release Kinetics and Bactericidal Effect, *J Biomed Mater Res B Appl Biomater* 2005 May; 73(2):277-84). Appropriate ratios of dicalcium phosphate and silicon components were placed in polyethylene bottles and mixed on a roller mixer for 24 h. The batch was moistened with 0.1 NaOH and placed in a Teflon mold. The samples were left to dry at room temperatures and then thermally treated (Thermolyne 30400, Barnstead International, Dubuque, Iowa) at 850° C. for 1 h. The heating temperature was selected based on the differential thermal analysis results previously reported (El-Ghannam, A. & Omran, M. Nanoporous Delivery System to Treat Osteomyelitis and Regenerate Bone: Gentamicin Release Kinetics and Bactericidal Effect. *Journal of Biomedical Materials Research. Part B, Applied Biomaterials* 73, 277-284 (2005)). The SCPC ceramic was ground, sifted and immersed in simulated body fluid (bovine serum) at 37° C. for 16 h. After immersion the samples were dried and the surface chemistry and morphology were analyzed by Fourier transform infrared spectroscopy (FTIR) and Scanning Electron Microscope-Energy Dispersive X-Ray (SEM-EDX) analyses, respectively. The SCPC particles were loaded with WLBU-2 using immersion method (e.g., as described in El-Ghannam, et al. *Journal of Biomedical Materials Research. Part B, Applied Biomaterials* 73, 277-284 (2005)) and dried.

Peptide Leaching. To evaluate potential leaching of the peptide being responsible for the antimicrobial activity of the bound CAP, a Transwell protein migration system was used. Bacteria was prepared as above to achieve an $A_{600}$=0.001 in PBS. Ten milligrams of Tentagel beads as well as Tentagel-WLBU-2 beads were weighed individually. Triplicate wells in a 96 well plate were set up by adding 600 μL of the bacterial solution for all of the following groups. The first group had bacterial suspension added to the lower compartment and Tentagel-WLBU-2 coated beads added to the upper compartment of the insert. The second group had bacterial suspension added to the lower compartment and Tentagel beads placed in the upper compartment of the insert. The third group had Tentagel beads to which bacterial suspension was added. The fourth group had Tentagel-WLBU-2 coated beads to which bacterial suspension was added. Initially, the plate was rested in a 37° C. room, but it was there was no difference between the four groups. A simple agitation was incorporated to the protocol and the described results were obtained. The plate was agitated in a 37° C. room and each group was subsequently plated to count cfu after overnight incubation in a 37° C. room. To assess the effect of agitation a control group consisting of PA01 suspension alone was used as baseline for bacterial growth.

Results and Discussion

Activity of bound WLBU-2 (SEQ ID NO: 10) to a carbohydrate-based gel matrix through the free amino group: Affigel, a carbohydrate-based gel matrix, was used to couple WLBU-2 through the primary amino group on the N-terminus. The conjugation rate to the slurry Affigel resin was determined to be 98.9% of available WLBU-2 by HPLC and the calculated concentration of bound peptide was estimated to be 20 μg/mL of resin. In order to test the antimicrobial properties retained by WLBU-2 attached to surfaces, *Psuedomonas aeruginosa* strain PA01 was filtered through an Affigel column without significant effect on the subsequent growth of PA01. The identical inoculum was filtered through an Affigel-WLBU-2 column and very few colonies survived after an overnight incubation (FIG. 22). The Affigel-WLBU-2 column remained effective in two additional tests with identical results. However, with additional testing a ten-fold higher bacterial survival was seen, indicating that the binding by the Affigel-WLBU-2 column were saturated. The activity of the Affigel-WLBU-2 column was reestablished with a simple methanol wash (data not shown).

Activity of WLBU-2 (SEQ ID NO: 10) bound to a complex polymer plastic bead through the carboxyl terminus. Attempting to demonstrate tethering of a peptide through either end, WLBU-2 was synthetically built on a polymeric plastic bead via the free carboxyl group. Analysis of the Tentagel beads indicated that the substitution rate was 390 mg/g resin. As depicted in FIG. 22, the WLBU-2 coated beads were able to kill the PA01 strain. The comparison group with Tentagel beads alone revealed no difference in the survival of *P. aeruginosa* when compared to a control group.

To determine that bacterial killing was not simply a result of WLBU-2 leeching a Transwell permeable support system was used. Tentagel-WLBU-2 beads placed in the upper compartment did not affect the growth of PA01 in the lower compartment when compared to a control group (FIG. 22). Tentagel beads in suspension with PA01 did not have an affect on the growth of PA01, while the Tentagel-WLBU-2 beads were able to sterilize the PA01 suspension. These data demonstrate that it is the physical interaction between the coupled WLBU-2 and PA01 that needed for the antimicrobial property. It also demonstrates that the antimicrobial properties are not attributable to uncoupled WLBU-2.

Activity of WLBU-2 (SEQ ID NO: 10) bound to a complex of silica-calcium phosphate nanocomposite associated with bone reconstruction. A novel resorbable bioactive porous silica-calcium phosphate nanocomposite (SCPC) that has the ability to stimulate bone regeneration and graft material resorption in vivo has been proposed (El-Ghannam, A. et al., *Journal of Biomedical Materials Research. Part B, Applied Biomaterials* 73, 277-284 (2005)). WLBU-2's antimicrobial activity covalently incorporated in to SCPC was evaluated. Comparison of the SCPC versus SCPC-WLBU-2 composite material was performed by adding 1 mg of either of these preparations to a 11.5 mL Eppendorf tube containing $1 \times 10^6$ *P. aeruginosa* strain PA01 in 1 mL of PBS. When static incubation (i.e., no agitation) was applied to the SCPC-WLBU-2 minimal killing was achieved after 1 h (not shown). However, when agitation was included in the protocol, the bacterial suspension was completely sterilized (FIG. 23). This reinforces that contact between the coupled WLBU-2 and a bacterium is necessary for effective killing. Scanning electron microscopy (SEM) was used to visually assess these beads. Using the identical bacterial suspensions, it was surprising to see that no bacteria were attached to the surface of the SCPC (FIG. 22A). However, the SCPC-WLBU-2 material had bacteria associated to the surface even though bacterial growth was negative (FIG. 23). In data not shown, we determined that these bacteria were being lysed because β-galactosidase (an intracellular bacterial enzyme) was released into the buffer (see, Phadke, S. M. et al. Selective toxicity of engineered lentivirus lytic peptides in a CF airway cell model. *Peptides* 24, 1099-1107 (2003)). These data support our contention that the positively charged peptide recruits the bacteria to the surface of the bead, resulting in the lysis of the bacteria.

Devices such as prosthetic joints, prosthetic heart valves, stents, cardiac pacemakers, intravenous catheters (IVC) and cerebrospinal fluid shunts have become essential in the medical field. However, these medical devices are at risk for infection and impact the rate of nosocomial infections. Unlike IVC infections, most foreign body-related infections require surgical removal. It is estimated that the United States averages between 200,000 to 400,000 catheter-related infection (CRI) per year. In patients with long term need of intravenous access, systemic as well as antibiotic lock therapy may be implemented to salvage a catheter (von Eiff, C., Jansen, B., Kohnen, W. & Becker, K. Infections associated with medical devices: pathogenesis, management and prophylaxis. *Drugs* 65, 179-214 (2005)). Biofilm formation on biomedical surfaces is considered the basis for infection (von Eiff, C., et al., *Drugs* 65, 179-214 (2005) and Falagas, M. E., Fragoulis, K., Bliziotis, I. A. & Chatzinikolaou, I. Rifampicin-impregnated central venous catheters: a meta-analysis of randomized controlled trials. *J Antimicrob Chemother* 59, 359-369 (2007)). Initial bacterial adherence is considered essential for the formation of biofilm on catheter surfaces (von Eiff, C., et al., *Drugs* 65, 179-214 (2005) and Falagas, M. E., et al., *J Antimicrob Chemother* 59, 359-369 (2007)). CRIs can be difficult to treat in part due to higher minimal inhibitory concentration exhibited by pathogens in the biofilm (Cirioni, O. et al. Pretreatment of central venous catheters with the cathelicidin BMAP-28 enhances the efficacy of antistaphylococcal agents in the treatment of experimental catheter-related infection. *Peptides* 27, 2104-2110 (2006) and Burton, E. et al. Antibiofilm activity of GlmU enzyme inhibitors against catheter-associated uropathogens. *Antimicrob Agents Chemother* 50, 1835-1840 (2006)).

Reduction of biofilm formation can have a great impact in infection rates that stem from prosthetics and CRI. In the past strategies to reduce biofilm formation included silver impregnated catheters, however, leaching leaves these materials vulnerable to bacterial adherence. The concept of an antimicrobial peptide as a means to reduce or prevent biofilm formation is feasible. Here, it is shown that WLBU-2 can be permanently, covalently attached to various surfaces while retaining its previously demonstrated antimicrobial properties in vivo and in vitro against *P. aeruginosa*. Tethered peptides need direct contact with the bacteria in order to have effective killing. As can be seen in the SEM images (FIG. 23), the bacteria are attracted to the WLBU-2 bound to the nanocomposite. The lack of growth from samples obtained provides evidence of bacterial lysis. The implications from these experiments suggest that bound WLBU-2, as well as other antimicrobial peptides described herein, are now expected to be effective in the prevention of bacterial biofilm formation by reduction of bacterial survival post contact with WLBU-2 coupled material. These findings have implications for understanding the surface-active mechanism of WLBU-2 action and have translational health applications for antimicrobial coating of medical devices.

Example 8

Seasonal Influenza Virus

We have previous reported that these peptides are active against enveloped herpesviruses such as Herpes Simplex Viruses (HSV) (Isaacs, C. E. et al. Inactivation of herpes simplex virus clinical isolates by using a combination microbicide. *Antimicrob Agents Chemother* 50, 1063-1066 (2006)). The following represents data with respect to an orthomyxovirus—Seasonal Influenza Virus.

Figure 24:
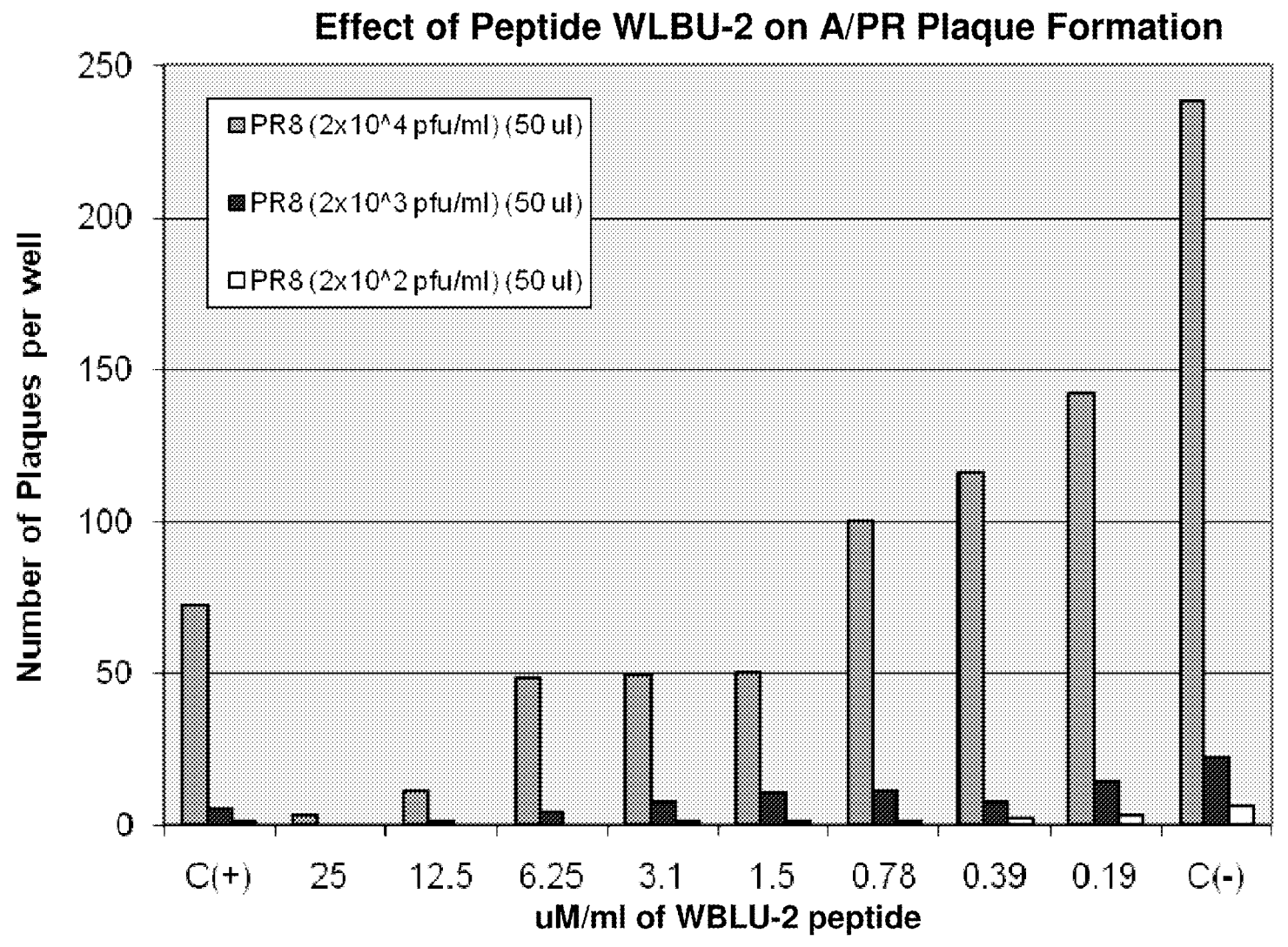

Seasonal Influenza virus: Eleven two-fold serial dilutions of WLBU-2 (SEQ ID NO: 10) (50 µM) were tested for hemagglutination inhibition (HAI) activity. The virus used for these studies was the seasonal isolate identified as Indonesia H5N1. As a positive control, mouse sera previously tested for HAI (HAI 1:1280) and as a negative control, phosphate buffered saline was used. Virus (25 µL HA=1:8) was incubated for 20 min with host cells under all conditions. The results demonstrate a dose-dependent decrease in infectious virus plaque formation (FIG. 24).

Figure 25:
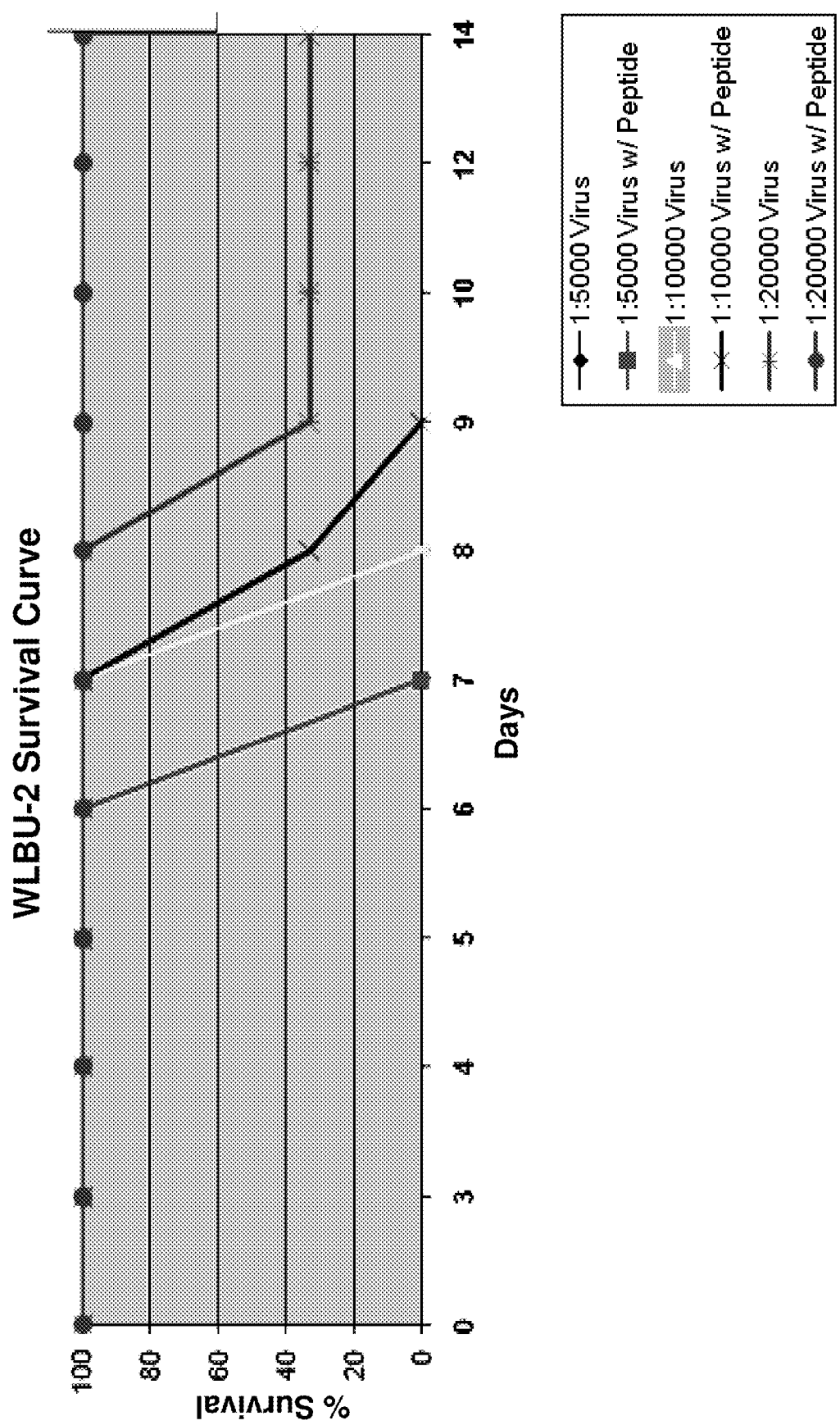
FIG. 25 is a graph showing the ability of WLBU-2 (SEQ ID NO: 10) to inactivate seasonal influenza virus in mice by intranasal administration of the peptide.

Similarly, we have evaluated the activity of seasonal influenza virus to cause disease in mice after exposure to our prototype peptide WLBU-2. For these experiments WLBU-2 was added to Indonesia H5N1 just prior to administering an intranasal dose of virus (FIG. 25). These data demonstrate the ability of peptide to inactivate the infectivity of virus.

Example 9

Bacillus anthracis

Figure 26:
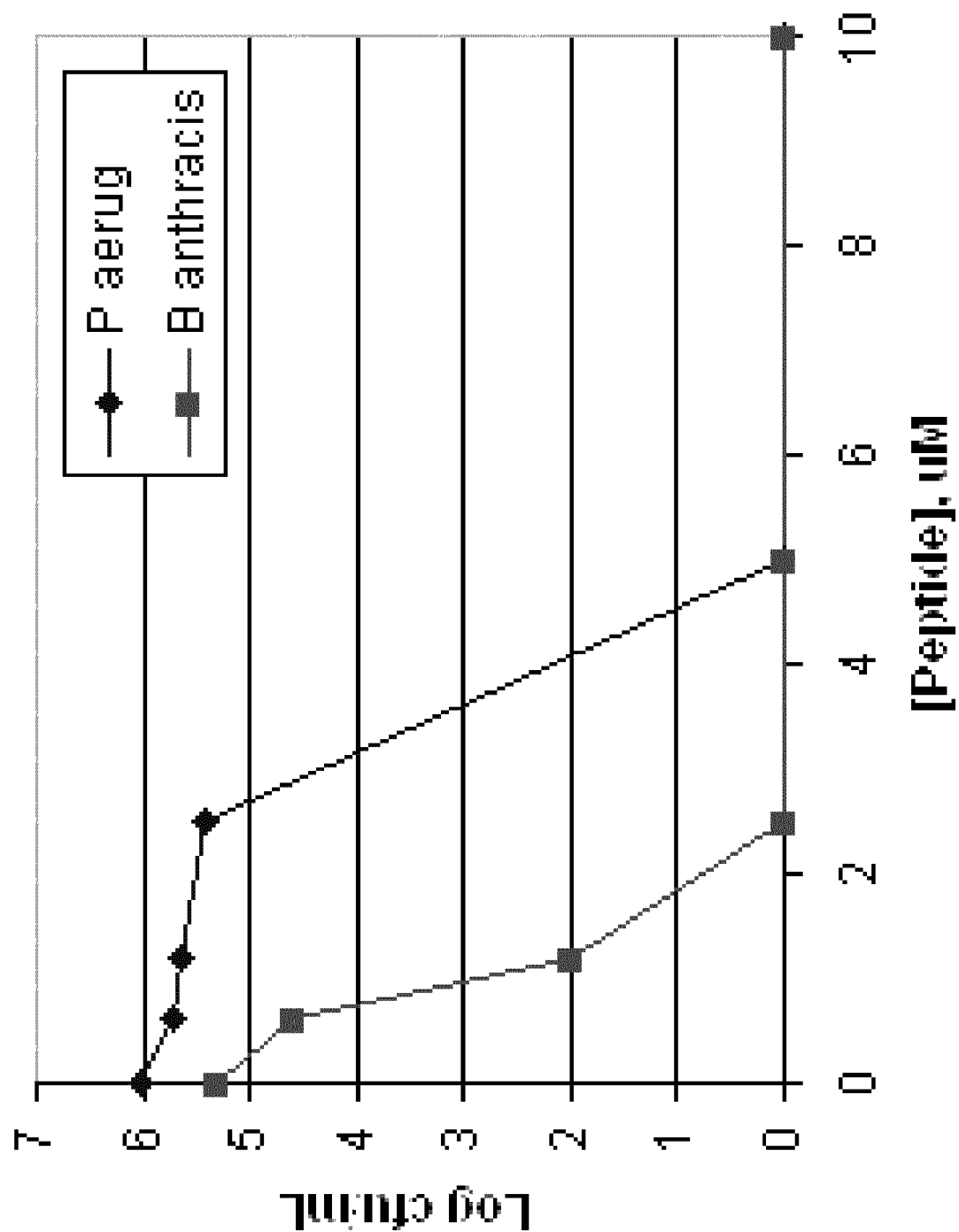
FIG. 26 is a graph showing the ability of WLBU-2 (SEQ ID NO: 10) to inhibit the vegetative form of B. anthracis.

Using the vaccine strain of *B. anthracis*, we have investigated the activity WLBU-2 (SEQ ID NO: 10) for its ability to inhibit the vegetative form of this organism (FIG. 26). These studies were performed analogous to the *P. aeruginosa* and *S. aureus* studies described above—growing bacteria to a specific cell density and then adding peptide to look for a decrease in viable counts. While the sporulating form of *B. anthracis* is clearly the susceptible form of *B. anthracis* and is clearly the target, the fact that we have been able to demonstrate that WLBU-2 is systemically active in a murine model against *P. aeruginosa* (Deslouches et al., Activity of the de novo engineered antimicrobial peptide WLBU-2 against *P. aeruginosa* in human serum and whole blood: implications for systemic applications, *Antimicrob Agents Chemother* 2005 August; 49(8):3208-16 and Deslouches, B. et al. De novo-derived cationic antimicrobial peptide activity in a murine model of *P. aeruginosa* bacteraemia. *J Antimicrob Chemother* 60, 669-672 (2007), and Example 4) suggest that the systemically circulating *B. anthracis* should be susceptible to WLBU-2 activity. These results illustrate that the peptides described herein could be used as a systemic prophylactic or therapeutic for mitigating against a biowarfare agent.

Example 10

Antifungal Activity

*Candida* spp. are major causes of sepsis. The objective was to investigate the antifungal activity of WLBU-2 (SEQ ID NO: 10) against diverse *Candida* spp: 11 *C. albicans* (4 flucoanzole-susceptible (S), 2 susceptible dose-dependent (S-DD), 4 resistant (R)), 4 *C. krusei* (all R), 4 *C. parapsilosis* (3S, 1R), 3 *C. tropicalis* (2S, 1S), 2 *C. galbrata* (1S, 1 S-DD, 1R), and 2 *C. lusitaniae* (S). Antifungal and fungicidal activities were assessed in vitro by MIC determinations and killing kinetics assays. During in vitro killing assays in RPMI 1640 at 37° C., WLBU-2 (6 µM) was fully fungicidal within 5 min against *C. albicans* reference strain SC5314, as well as all clinical *C. albicans* and *C. lusitaniae* and isolates. For both *C. krusei* and *C. tropicalis*, 75% of the isolates were completely killed by 3 µM of WUBL2. The remaining isolates were completely killed by 25 µM, but the minimum fungicidal concentrations (MFC, defined as >99.9% kill) were achieved at the concentrations ≦6 µM. We extended our assays to test 3 isolates of *Cryptococcocus neoformans* (2S, 1R) and 2 *Aspergillus fumigatus*. *C. neoformans* were completely killed by 3 µM, whereas the *A. fumigatus* isolates were resistant to 100 uM. The WLBU-2 is highly active against diverse *Candida* spp. and *C. neoformans* in vitro. Taken with the earlier data against *S. aureus* and *P. aeruginosa*, our findings indicate that WLBU-2 as well as, by inference, the other eCAPs described herein, have potent activity against numerous common causes of sepsis. As such, the eCAPs described herein are potentially useful in the treatment of sepsis or as empiric therapy of patients who might have sepsis. Once again, because the eCAPs have been shown to be active in vivo against gram positive and gram negative bacteria (Deslouches et al., Activity of the de novo engineered antimicrobial peptide WLBU-2 against *Pseudomonas aeruginosa* in human serum and whole blood: implications for systemic applications, *Antimicrob Agents Chemother* 2005 August; 49(8): 3208-16 and Deslouches, B. et al. De novo-derived cationic antimicrobial peptide activity in a murine model of *P. aeruginosa* bacteraemia. *J Antimicrob Chemother* 60, 669-672 (2007) and in Example 4, above), it is predicted that non-toxic doses of the peptides will be effective in prevention and treatment of *Candida* spp. (Candidiasis) and *Cryptococcus* infections in vivo.

Having described this invention above, it will be understood to those of ordinary skill in the art that the same can be performed within a wide and equivalent range of conditions, formulations and other parameters without affecting the scope of the invention or any embodiment thereof.

We claim:

1. An isolated and purified peptide having an amino acid sequence selected from the group consisting of:
RWWRWWRRWWRR (SEQ ID NO: 14);
WRRWWRRWWRWWRRWWRR (SEQ ID NO: 15); and
RRWWRRWRRWWRRWWRWWRRWWRR (SEQ ID NO: 16).

2. The peptide of claim 1, having the amino acid sequence: RWWRWWRRWWRR (SEQ ID NO: 14).

3. A composition comprising the peptide of claim 2 and a carrier.

4. The peptide of claim 1, having the amino acid sequence: WRRWWRRWWRWWRRWWRR (SEQ ID 15).

5. A composition comprising the peptide of claim 4 and a carrier.

6. The peptide of claim 1, having the amino acid sequence: RRWWRRWRRWWRRWWRWWRRWWRR (SEQ ID 16).

7. A composition comprising the peptide of claim 6 and a carrier.

8. A method of neutralizing an enveloped virus, comprising contacting the virus with one or more antimicrobial peptides chosen from WR12 (SEQ ID NO: 14); WR18 (SEQ ID NO: 15); and WR24 (SEQ ID NO: 16) in an amount effective to neutralize the enveloped virus.

9. The method of claim 8, in which the enveloped virus is chosen from one of poxvirus, herpesvirus, hepadnavirus, rhabdovirus, baculovirus, orthomyxovirus, paramyxovirus, retrovirus, togavirus, bunyavirus and flavivirus.

10. The method of claim 9, wherein the enveloped virus is a lentivirus.

11. The method of claim 10, wherein the lentivirus is a Human Immunodeficiency Virus.

12. The method of claim 11, wherein the Human Immunodeficiency Virus is HIV-1.

13. The method of claim 8, in which the antimicrobial peptide is administered to a subject in an amount effective to prevent or treat an enveloped virus infection, thereby preventing or treating an enveloped virus infection in the subject.

14. A method of neutralizing an orthomyxovirus, comprising contacting the virus with one or more antimicrobial peptides chosen from WR12 (SEQ ID NO: 14); WR18 (SEQ ID NO: 15); and WR24 (SEQ ID NO: 16) in an amount effective to neutralize the orthomyxovirus.

15. The method of claim 14, wherein the orthomyxovirus is an influenza virus.

16. The method of claim 14, in which the antimicrobial peptide is administered to a subject in an amount effective to prevent or treat an infection by an orthomyxovirus, thereby preventing or treating an infection by an orthomyxovirus.

17. A method of killing a *Bacillus anthracia* bacterium, vegetative form, comprising contacting the bacterium with one or more antimicrobial peptides chosen from WR12 (SEQ ID NO: 14); WR18 (SEQ ID NO: 15); and WR24 (SEQ ID NO: 16) in an amount effective to kill the bacterium.

18. The method of claim 17, in which the antimicrobial peptide is administered to a subject in an amount effective to prevent or treat a *B. anthracis* infection, thereby preventing or treating a *B. anthracis* infection.

19. A method of killing a fungus of the Genera *Candida* or *Cryptococcus*, comprising contacting the fungus with one or more antimicrobial peptides chosen from WR12 (SEQ ID NO: 14); WR18 (SEQ ID NO: 15); and WR24 (SEQ ID NO: 16) in an amount effective to kill the fungus.

20. The method of claim 19, in which the antimicrobial peptide is administered to a subject in an amount effective to prevent or treat a *Candida* or *Cryptococcus* infection, thereby preventing or treating a *Candida* or *Cryptococcus* infection.

21. The method of claim 20, in which the fungus is one or more of *C. albicans, C. krusei, C. parapsilosis, C. tropicalis, C. galbrata*, and *C. lusitaniae*.

22. An isolated and purified peptide-cargo complex comprising a cargo and a peptide chosen from WR12 (SEQ ID NO: 14); WR18 (SEQ ID NO: 15); and WR24 (SEQ ID NO: 16).

23. A solid phase substrate comprising at least one peptide chosen from: WR12 (SEQ ID NO: 14); WR18 (SEQ ID NO: 15); and WR24 (SEQ ID NO: 16).

24. The solid phase substrate of claim 23, wherein the solid phase substrate is a prosthetic device.

25. The solid phase substrate of claim 24, wherein the prosthetic device is a prosthetic joint.

26. The solid phase substrate of claim 23, wherein the solid phase substrate is a catheter.

* * * * *

UNITED STATES PATENT AND TRADEMARK OFFICE
CERTIFICATE OF CORRECTION

| | | |
|---|---|---|
| PATENT NO. | : 8,071,540 B2 | Page 1 of 1 |
| APPLICATION NO. | : 12/171806 | |
| DATED | : December 6, 2011 | |
| INVENTOR(S) | : Ronald C. Montelaro et al. | |

It is certified that error appears in the above-identified patent and that said Letters Patent is hereby corrected as shown below:

Column 46, Line 59, Claim 17, delete "anthracia" and insert -- anthracis --

Column 47, Line 12, Claim 21, delete "C. galbrata" and insert -- C. glabrata --

Signed and Sealed this
Twenty-ninth Day of May, 2012

David J. Kappos
*Director of the United States Patent and Trademark Office*

SEQUENCE LISTING

```
<160> NUMBER OF SEQ ID NOS: 19

<210> SEQ ID NO 1
<211> LENGTH: 28
<212> TYPE: PRT
<213> ORGANISM: Artificial Sequence
<220> FEATURE:
<223> OTHER INFORMATION: Antimicrobial peptide

<400> SEQUENCE: 1

Arg Val Ile Arg Val Val Gln Arg Ala Cys Arg Ala Ile Arg His Ile
1               5                   10                  15

Val Arg Arg Ile Arg Gln Gly Leu Arg Arg Ile Leu
            20                  25

<210> SEQ ID NO 2
<211> LENGTH: 31
<212> TYPE: PRT
<213> ORGANISM: Artificial Sequence
<220> FEATURE:
```

<223> OTHER INFORMATION: Antimicrobial Peptide

<400> SEQUENCE: 2

Arg Val Ile Arg Val Val Gln Arg Ala Cys Arg Ala Ile Arg His Ile
1               5                   10                  15

Val Arg Arg Ile Arg Gln Gly Leu Arg Arg Ile Leu Arg Val Val
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Antimicrobial peptide

<400> SEQUENCE: 3

Arg Trp Ile Arg Val Val Gln Arg Trp Cys Arg Ala Ile Arg His Ile
1               5                   10                  15

Trp Arg Arg Ile Arg Gln Gly Leu Arg Arg Trp Leu Arg Val Val
            20                  25                  30

<210> SEQ ID NO 4
<211> LENGTH: 12
<212> TYPE: PRT
<213> ORGANISM: Artificial Sequence
<220> FEATURE:
<223> OTHER INFORMATION: Antimicrobial peptide

<400> SEQUENCE: 4

Arg Val Val Arg Val Val Arg Arg Val Val Arg Arg
1               5                   10

<210> SEQ ID NO 5
<211> LENGTH: 24
<212> TYPE: PRT
<213> ORGANISM: Artificial Sequence
<220> FEATURE:
<223> OTHER INFORMATION: Antimicrobial peptide

<400> SEQUENCE: 5

Arg Arg Val Val Arg Arg Val Arg Arg Val Val Arg Arg Val Val Arg
1               5                   10                  15

Val Val Arg Arg Val Val Arg Arg
            20

<210> SEQ ID NO 6
<211> LENGTH: 36
<212> TYPE: PRT
<213> ORGANISM: Artificial Sequence
<220> FEATURE:
<223> OTHER INFORMATION: Antimicrobial peptide

<400> SEQUENCE: 6

Val Arg Arg Val Val Arg Arg Val Val Arg Val Val Arg Val Val
1               5                   10                  15

Arg Arg Val Arg Arg Val Val Arg Arg Val Val Arg Val Val Arg Arg
            20                  25                  30

Val Val Arg Arg
        35

<210> SEQ ID NO 7
<211> LENGTH: 42
<212> TYPE: PRT
<213> ORGANISM: Artificial Sequence
<220> FEATURE:

<223> OTHER INFORMATION: Antimicrobial peptide

<400> SEQUENCE: 7

Arg Arg Val Val Arg Val Arg Val Val Arg Val Arg Val Arg Val
1               5                   10                  15

Val Val Arg Val Val Arg Arg Val Arg Arg Val Val Arg Arg Val
                20                  25                  30

Val Arg Val Val Arg Arg Val Val Arg Arg
        35                  40

<210> SEQ ID NO 8
<211> LENGTH: 48
<212> TYPE: PRT
<213> ORGANISM: Artificial Sequence
<220> FEATURE:
<223> OTHER INFORMATION: Antimicrobial peptide

<400> SEQUENCE: 8

Arg Val Val Arg Val Val Arg Arg Val Val Arg Val Arg Arg Val
1               5                   10                  15

Val Arg Arg Val Val Arg Val Val Arg Arg Val Val Arg Val Arg
                20                  25                  30

Arg Val Val Arg Val Val Arg Val Val Arg Val Val Arg Val Arg
        35                  40                  45

<210> SEQ ID NO 9
<211> LENGTH: 12
<212> TYPE: PRT
<213> ORGANISM: Artificial Sequence
<220> FEATURE:
<223> OTHER INFORMATION: Antimicrobial peptide

<400> SEQUENCE: 9

Arg Val Val Arg Val Val Arg Arg Trp Val Arg Arg
1               5                   10

<210> SEQ ID NO 10
<211> LENGTH: 24
<212> TYPE: PRT
<213> ORGANISM: Artificial Sequence
<220> FEATURE:
<223> OTHER INFORMATION: Antimicrobial peptide

<400> SEQUENCE: 10

Arg Arg Trp Val Arg Arg Val Arg Arg Val Trp Arg Arg Val Val
1               5                   10                  15

Val Val Arg Arg Trp Val Arg Arg
                20

<210> SEQ ID NO 11
<211> LENGTH: 36
<212> TYPE: PRT
<213> ORGANISM: Artificial Sequence
<220> FEATURE:
<223> OTHER INFORMATION: Antimicrobial peptide

<400> SEQUENCE: 11

Val Arg Arg Val Trp Arg Arg Val Val Arg Val Val Arg Arg Trp Val
1               5                   10                  15

Arg Arg Val Arg Arg Val Trp Arg Arg Val Val Arg Val Val Arg Arg
                20                  25                  30

Trp Val Arg Arg
        35

<210> SEQ ID NO 12
<211> LENGTH: 48
<212> TYPE: PRT
<213> ORGANISM: Artificial Sequence
<220> FEATURE:
<223> OTHER INFORMATION: Antimicrobial peptide

<400> SEQUENCE: 12

```
Arg Val Val Arg Val Val Arg Arg Trp Val Arg Val Arg Arg Val
1               5                   10                  15

Trp Arg Arg Val Val Arg Val Val Arg Arg Trp Val Arg Arg Val Arg
                20                  25                  30

Arg Val Trp Arg Arg Val Val Arg Val Val Arg Arg Trp Arg Val Val
                35                  40                  45
```

<210> SEQ ID NO 13
<211> LENGTH: 6
<212> TYPE: PRT
<213> ORGANISM: Artificial Sequence
<220> FEATURE:
<223> OTHER INFORMATION: Antimicrobial peptide

<400> SEQUENCE: 13

```
Arg Arg Trp Trp Arg Arg
1               5
```

<210> SEQ ID NO 14
<211> LENGTH: 12
<212> TYPE: PRT
<213> ORGANISM: Artificial Sequence
<220> FEATURE:
<223> OTHER INFORMATION: Antimicrobial peptide

<400> SEQUENCE: 14

```
Arg Trp Trp Arg Trp Trp Arg Arg Trp Trp Arg Arg
1               5                   10
```

<210> SEQ ID NO 15
<211> LENGTH: 18
<212> TYPE: PRT
<213> ORGANISM: Artificial Sequence
<220> FEATURE:
<223> OTHER INFORMATION: Antimicrobial peptide

<400> SEQUENCE: 15

```
Trp Arg Arg Trp Trp Arg Arg Trp Trp Arg Trp Trp Arg Arg Trp Trp
1               5                   10                  15

Arg Arg
```

<210> SEQ ID NO 16
<211> LENGTH: 24
<212> TYPE: PRT
<213> ORGANISM: Artificial Sequence
<220> FEATURE:
<223> OTHER INFORMATION: Antimicrobial peptide

<400> SEQUENCE: 16

```
Arg Arg Trp Trp Arg Arg Trp Arg Arg Trp Trp Arg Arg Trp Trp Arg
1               5                   10                  15

Trp Trp Arg Arg Trp Trp Arg Arg
                20
```

<210> SEQ ID NO 17
<211> LENGTH: 12
<212> TYPE: PRT

```
<213> ORGANISM: Artificial Sequence
<220> FEATURE:
<223> OTHER INFORMATION: Peptide transduction domain

<400> SEQUENCE: 17

Arg Arg Gln Arg Arg Thr Ser Lys Leu Met Lys Arg
1               5                   10

<210> SEQ ID NO 18
<211> LENGTH: 35
<212> TYPE: PRT
<213> ORGANISM: Artificial Sequence
<220> FEATURE:
<223> OTHER INFORMATION: Antimicrobial peptide

<400> SEQUENCE: 18

Arg Arg Gln Arg Arg Thr Ser Lys Leu Met Lys Arg Arg Arg Trp Val
1               5                   10                  15

Arg Arg Val Arg Arg Val Trp Arg Val Val Arg Val Val Arg Arg Trp
            20                  25                  30

Val Arg Arg
        35

<210> SEQ ID NO 19
<211> LENGTH: 28
<212> TYPE: PRT
<213> ORGANISM: Human immunodeficiency virus type 1

<400> SEQUENCE: 19

Arg Val Ile Glu Val Val Gln Gly Ala Cys Arg Ala Ile Arg His Ile
1               5                   10                  15

Pro Arg Arg Ile Arg Gln Gly Leu Glu Arg Ile Leu
            20                  25
```